United States Patent
Wang et al.

(10) Patent No.: US 11,111,295 B2
(45) Date of Patent: Sep. 7, 2021

(54) ANTIBODY FOR ANTI-CLAUDIN 18A2 AND USE THEREOF

(71) Applicant: CAFA THERAPEUTICS LIMITED, Dublin (IE)

(72) Inventors: Peng Wang, Shanghai (CN); Hua Jiang, Shanghai (CN); Linlin Yang, Shanghai (CN); Zhimin Shi, Shanghai (CN); Huamao Wang, Shanghai (CN); Zonghai Li, Shanghai (CN)

(73) Assignee: CAFA THERAPEUTICS LIMITED, Dublin (IE)

( * ) Notice: Subject to any disclaimer, the term of this patent is extended or adjusted under 35 U.S.C. 154(b) by 126 days.

(21) Appl. No.: 16/316,331

(22) PCT Filed: Jul. 10, 2017

(86) PCT No.: PCT/CN2017/092381
§ 371 (c)(1),
(2) Date: Jan. 8, 2019

(87) PCT Pub. No.: WO2018/006882
PCT Pub. Date: Jan. 11, 2018

(65) Prior Publication Data
US 2019/0233511 A1    Aug. 1, 2019

(30) Foreign Application Priority Data

Jul. 8, 2016  (CN) .......................... 201610536449.9
Apr. 26, 2017  (WO) ................ PCT/CN2017/082024

(51) Int. Cl.
| | |
|---|---|
| *C07K 16/28* | (2006.01) |
| *A61P 35/00* | (2006.01) |
| *C07K 16/30* | (2006.01) |
| *C12N 15/85* | (2006.01) |
| *C12N 5/10* | (2006.01) |
| *A61K 39/395* | (2006.01) |
| *C07K 19/00* | (2006.01) |
| *A61K 47/68* | (2017.01) |
| *A61K 9/00* | (2006.01) |
| *A61K 31/282* | (2006.01) |
| *A61K 31/704* | (2006.01) |
| *A61K 31/7115* | (2006.01) |
| *A61K 35/17* | (2015.01) |

(52) U.S. Cl.
CPC ............ *C07K 16/28* (2013.01); *A61K 9/0019* (2013.01); *A61K 31/282* (2013.01); *A61K 31/704* (2013.01); *A61K 31/7115* (2013.01); *A61K 35/17* (2013.01); *A61K 39/395* (2013.01); *A61K 47/6803* (2017.08); *A61P 35/00* (2018.01); *C07K 16/30* (2013.01); *C07K 19/00* (2013.01); *C12N 5/10* (2013.01); *C12N 15/85* (2013.01)

(58) Field of Classification Search
CPC .. C07K 16/28; A61K 47/6803; A61K 9/0019; A61K 31/282; A61K 31/704; A61K 31/7115; A61K 35/17; C12N 15/85; A61P 35/00
See application file for complete search history.

(56) References Cited

U.S. PATENT DOCUMENTS

| | | | |
|---|---|---|---|
| 8,168,427 B2 | 5/2012 | Sahin et al. | |
| 9,212,228 B2 | 12/2015 | Sahin et al. | |
| 9,499,609 B2 | 11/2016 | Sahin et al. | |
| 9,512,232 B2 | 12/2016 | Sahin et al. | |
| 9,751,934 B2 | 9/2017 | Sahin et al. | |
| 10,017,564 B2 | 7/2018 | Sahin et al. | |
| 10,053,512 B2 | 8/2018 | Sahin et al. | |
| 10,137,195 B2 | 11/2018 | Sahin et al. | |
| 10,174,104 B2 | 1/2019 | Sahin et al. | |
| 10,314,890 B2 * | 6/2019 | Sahin ................... | C07K 16/28 |
| 2009/0169547 A1 | 7/2009 | Sahin | |
| 2012/0164160 A1 | 6/2012 | Sahin et al. | |
| 2012/0195830 A1 | 8/2012 | Sahin et al. | |
| 2015/0147763 A1 | 5/2015 | Sahin et al. | |
| 2015/0252103 A1 | 9/2015 | Sahin et al. | |
| 2015/0252104 A1 | 9/2015 | Sahin et al. | |
| 2016/0008465 A1 | 1/2016 | Sahin et al. | |
| 2016/0185860 A1 | 6/2016 | Sahin et al. | |
| 2016/0333109 A1 | 11/2016 | Sahin et al. | |
| 2018/0127489 A1 | 5/2018 | Sahin et al. | |
| 2018/0319891 A1 | 11/2018 | Sahin et al. | |
| 2020/0385448 A1 | 12/2020 | Sahin et al. | |

FOREIGN PATENT DOCUMENTS

| | | |
|---|---|---|
| CN | 101312989 A | 11/2008 |
| CN | 104321345 A | 1/2015 |
| WO | 2007059997 A1 | 5/2007 |
| WO | 2013167153 A1 | 11/2013 |
| WO | 2013167259 A1 | 11/2013 |
| WO | 2014146672 A1 | 9/2014 |

(Continued)

OTHER PUBLICATIONS

Malia et al., Proteins, 2016; 84:427-434. (Year: 2016).*

(Continued)

*Primary Examiner* — Brad Duffy
*Assistant Examiner* — Cheom-Gil Cheong
(74) *Attorney, Agent, or Firm* — Carl A. Morales; Kurtis M. Anderson; Dechert LLP

(57) ABSTRACT

Provided in the present invention is an antibody for anti-claudin 18A2 and an immune effector cell targeting claudin 18A2. Also provided are methods for inducing cell death and treating tumours.

29 Claims, 12 Drawing Sheets
Specification includes a Sequence Listing.

(56) References Cited

FOREIGN PATENT DOCUMENTS

| WO | 2014146778 A1 | 9/2014 |
|---|---|---|
| WO | 2016008405 A1 | 1/2016 |
| WO | 2017096163 A1 | 6/2017 |

OTHER PUBLICATIONS

Barthelemy et al., Journal of Biological Chemistry, 2008, 283:3639-3654. (Year: 2008).*
Beiboeretal., Journal of Molecular Biology, 2000, 296:833-849. (Year: 2000).*
Choi et al., 2011, Molecular BioSystems, 2011,7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Klamp et al., 2011 "Highly Specific Auto-Antibodies against Claudin-18 Isoform 2 Induced by a Chimeric HBcAg Virus-Like Particle Vaccine Kill Tumor Cells and Inhibit the Growth of Lung Metastases," Cancer Res 71(2):516-527.
Office Action in related Russian Application No. 2019101430/10(002310), dated Dec. 25, 2020 with English translation (11 pages).
Technical Report in related Chilean Application No. 201900061, dated Aug. 26, 2020 (22 pages).
Search Report in related Chilean Application No. 201900061, dated Aug. 26, 2020 (5 pages).
Extended European Search Report for related European Application No. 17823694.9, dated Jun. 29, 2020 (14 pages).
Sahin et al., 2008 "Claudin-18 splice variant 2 is a pan-cancer target suitable for therapeutic antibody development," Clin Cancer Res 14(23):7624-34.
Thorston et al., 2011 "Highly Specific Auto-Antibodies against Claudin-18 Isoform 2 Induced by a Chimeric HBcAg Virus-Like Particle Vaccine Kill Tumor Cells and Inhibit the Growth of Lung Metastases," Cancer Res 71(2):516-27.
International Preliminary Report on Patentability for PCT/CN2017/092381 dated Jan. 8, 2019 (6 pages).
International Search Report of the International Searching Authority for PCT/CN2017/092381 dated Oct. 12, 2017 (7 pages).
Written Opinion of the International Searching Authority for PCT/CN2017/092381 dated Oct. 12, 2017 (5 pages).

* cited by examiner

```
SP|P56856|CLD18_HUMAN    MSTTTCQVVAFLLSILGLAGCIAATGMDMWSTQDLYDNPVTSVFQYEGLWRSCVRQSSGF 60
SP|P56856-2|CLD18_HUMAN  MAVTACQGLGFVVSLIGIAGIIAATCMDQWSTQDLYNNPVTAVFNYQGLWRSCVRESSGF 60
                         *:.*:** :.*::*::*:** **** ** *******:****:**:*:*********:****

SP|P56856|CLD18_HUMAN    TECRPYFTILGLPAMLQAVRALMIVGIVLGAIGLLVSIFALKCIRIGSMEDSAKANMTLT 120
SP|P56856-2|CLD18_HUMAN  TECRGYFTLLGLPAMLQAVRALMIVGIVLGAIGLLVSIFALKCIRIGSMEDSAKANMTLT 120
                         **** ***:***************************************************

SP|P56856|CLD18_HUMAN    SGIMFIVSGLCAIAGVSVFANMLVTNFWMSTANMYTGMGGMVQTVQTRYTFGAALFVGWV 180
SP|P56856-2|CLD18_HUMAN  SGIMFIVSGLCAIAGVSVFANMLVTNFWMSTANMYTGMGGMVQTVQTRYTFGAALFVGWV 180
                         ************************************************************

SP|P56856|CLD18_HUMAN    AGGLTLIGGVMMCIACRGLAPEETNYKAVSYHASGHSVAYKPGGFKASTGFGSNTKNKKI 240
SP|P56856-2|CLD18_HUMAN  AGGLTLIGGVMMCIACRGLAPEETNYKAVSYHASGHSVAYKPGGFKASTGFGSNTKNKKI 240
                         ************************************************************

SP|P56856|CLD18_HUMAN    YDGGARTEDEVQSYPSKHDYV 261
SP|P56856-2|CLD18_HUMAN  YDGGARTEDEVQSYPSKHDYV 261
                         *********************
```

FIG. 1A (A) Heavy Chain

```
                       HCDR1                                          HCDR2
2B1(scFv-Fc)  QVQLQQSGAELARPGASVKMSCKASGYTFT S-YTMH WVKQR PGQGLEWI G YINPSSGYTNYNQKFKD KAT
3E12(scFv-Fc) QVQLQQSGPELVKPGALVKI SCKASGYTFT S-YDI N WVKQR PGQGLEWI G WIYPGDGSTKYNEKFKG KAT
4A11(scFv-Fc) QIQLVQSGPELKKPGETVKI SCKASGYTFT N-YGMN WVKQA PGKGLKWMG WINTNTGEPTYAEEFKG RFA
8E5(scFv-Fc)  DVQLQESGPDLVKPSQSLSLTCTVTGYSI T SGYNWH WIRQF PGNKMEWMG YIHY-TGSTNYNPSLRS RIS
                                                                  HCDR3
2B1(scFv-Fc)  LTADKSSSTAYMQLSSLTSEDSAVYYCAR --IYYGNSFAY WGQGTTVTVSS
3E12(scFv-Fc) LTADKSSSTAYMQLSSLTSENSAVYFCAR GGYRYDEAMDY WGQGTTVTVSS
4A11(scFv-Fc) FSLETSASTAYLQINNLKNEDTATYFCAR --FSYGNSFAY WGQGTTVTVSS
8E5(scFv-Fc)  ITRDTSKNQFFLQLNSVTTDDTATYYCTR --IYNGNSFPY WGQGTSVTVSS
```

(B) Light Chain

```
                                LCDR1                                 LCDR2
2B1  DIVMTQSPSSLTVTAGEKVTMSC KSSQSLLNSGNQKNYLT WYQQKPGQPPKLLI Y WASTRES GVPDRFTG
3E12 QIVLTQSPAIMSASPGEKVTMTC SASSSI S------YMH WYQQKPGTSPKRWI Y DTSKLAS GVPARFSG
4A11 DIVMTQSPSSLSVSAGEKVTMSC KSSQSLLNSGNQKNYLA WYQQKPGQPPKLLI Y GASTRES GVPDRFTG
8E5  DIVMTQSPSSLTVTPGEKVTMTC KSSQSLFNSGNQKNYLT WYQQRPGQPPKMLI Y WASTRES GVPDRFTG
                                       LCDR3
2B1  SGSGTDFTLTI SSVQAEDLAVYYC QNDYSYPLT FGAGTKLELK
3E12 SGSGTSYSLTI SSMEAEDAATYYC HQRSSYPYT FGGGTKLEIK
4A11 SGSGTDFTLTI SSVQAEDLAVYYC QNDHSYPLT FGAGTKLELK
8E5  SGSGTDFTLTI SSVQAEDLAVFYC QNAYSFPYT FGGGTKLEIK
```

FIG. 2

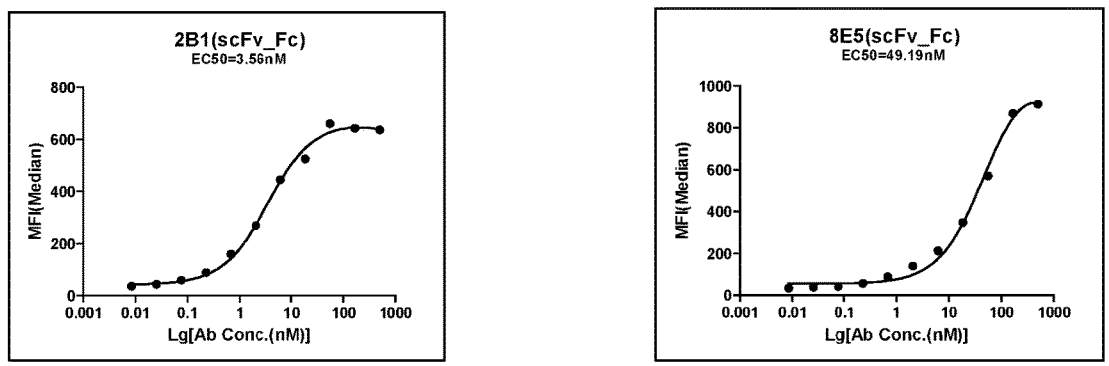

FIG. 3

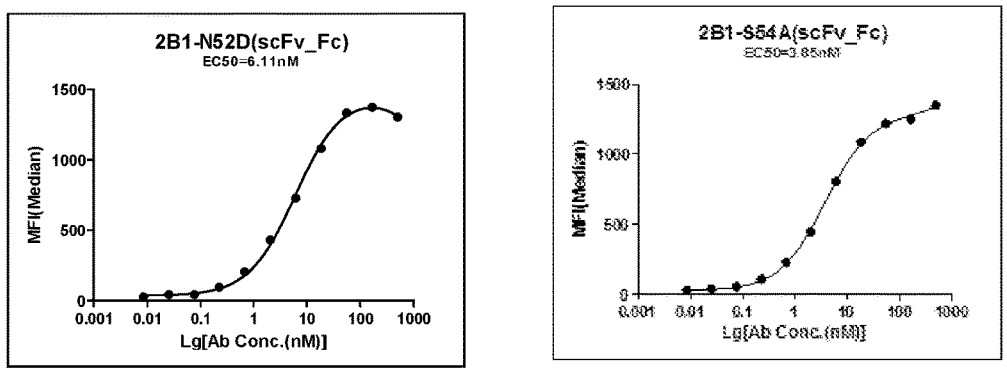

FIG. 4

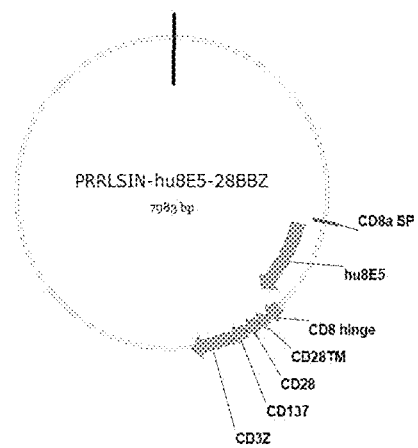
FIG. 18A
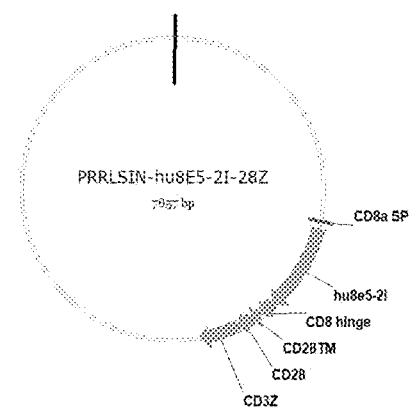
FIG. 18B
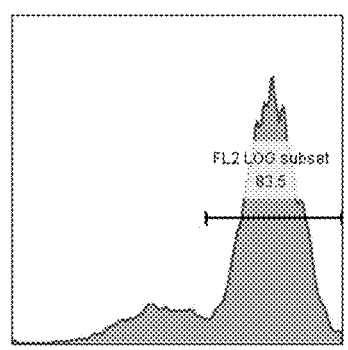 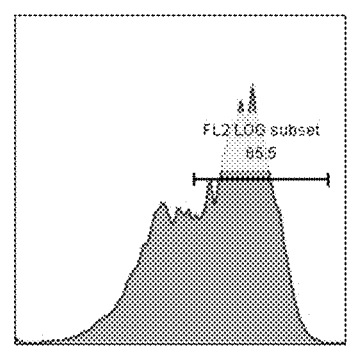
hu8E5-2I-28Z CAR-NK92          hu8E5-28BBZ CAR-NK92
FIG. 19

SEQUENCE LISTING

<160> NUMBER OF SEQ ID NOS: 94

<210> SEQ ID NO 1
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 1

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg

<210> SEQ ID NO 2
<211> LENGTH: 342

<212> TYPE: DNA
<213> ORGANISM: Artificial Sequence
<220> FEATURE:
<223> OTHER INFORMATION: synthetic polynucleotide

<400> SEQUENCE: 2

```
gacattgtga tgacacagtc tccatcctcc ctgactgtga cagcaggaga gaaggtcact    60
atgagctgca agtccagtca gagtctgtta aacagtggaa atcaaaagaa ctacttgacc   120
tggtaccagc agaaaccagg gcagcctcct aaactgttga tctactgggc atccactagg   180
gaatctgggg tccctgatcg cttcacaggc agtggatctg gaacagattt cactctcacc   240
atcagcagtg tgcaggctga agacctggca gtttattact gtcagaatga ttatagttat   300
ccgctcacgt tcggtgctgg gaccaagctg gagctgaaac gg                      342
```

<210> SEQ ID NO 3
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 3

```
Gln Val Gln Leu Gln Gln Ser Gly Ala Glu Leu Ala Arg Pro Gly Ala
1               5                   10                  15
Ser Val Lys Met Ser Cys Lys Ala Ser Gly Tyr Thr Phe Thr Ser Tyr
            20                  25                  30
Thr Met His Trp Val Lys Gln Arg Pro Gly Gln Gly Leu Glu Trp Ile
        35                  40                  45
Gly Tyr Ile Asn Pro Ser Ser Gly Tyr Thr Asn Tyr Asn Gln Lys Phe
    50                  55                  60
Lys Asp Lys Ala Thr Leu Thr Ala Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Ile Tyr Tyr Gly Asn Ser Phe Ala Tyr Trp Gly Gln Gly Thr
            100                 105                 110
Thr Val Thr Val Ser Ser
        115
```

<210> SEQ ID NO 4
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 4

```
caggtccagc tgcagcagtc tggggctgaa ctggcaagac ctggggcctc agtgaagatg    60
tcctgcaagg cttctggcta cacctttact agctacacga tgcactgggt aaaacagagg   120
cctggacagg gtctggaatg gattggatac attaatccta gcagtggtta ctactaattac  180
aatcagaagt tcaaggacaa ggccacattg actgcagaca atcctccag cacagcctac    240
atgcaactga gcagcctgac atctgaggac tctgcagtct attactgtgc aagaatctac   300
tatggtaact cgtttgctta ctggggccaa gggaccacgg tcaccgtctc ctca         354
```

<210> SEQ ID NO 5
<211> LENGTH: 107
<212> TYPE: PRT

```
<213> ORGANISM: Artificial Sequence
<220> FEATURE:
<223> OTHER INFORMATION: synthetic polypeptide

<400> SEQUENCE: 5

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Tyr Thr
                85                  90                  95

Phe Gly Gly Gly Thr Lys Leu Glu Ile Lys Arg
            100                 105

<210> SEQ ID NO 6
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 6
caaattgttc tcacccagtc tccagcaatc atgtctgcat ctccagggga gaaggtcacc      60
atgacctgca gtgccagctc aagtataagt tacatgcact ggtaccagca gaagccaggc     120
acctccccca aaagatggat ttatgacaca tccaaactgg cttctggagt ccctgctcgc     180
ttcagtggca gtgggtctgg gacctcttat tctctcacaa tcagcagcat ggaggctgaa     240
gatgctgcca cttattactg ccatcagcgg agtagttacc cgtacacgtt cggagggggg     300
accaagctgg aaataaaacg g                                               321

<210> SEQ ID NO 7
<211> LENGTH: 120
<212> TYPE: PRT
<213> ORGANISM: Artificial Sequence
<220> FEATURE:
<223> OTHER INFORMATION: synthetic polypeptide

<400> SEQUENCE: 7

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Gly Gly Tyr Arg Tyr Asp Glu Ala Met Asp Tyr Trp Gly Gln
            100                 105                 110
```

Gly Thr Thr Val Thr Val Ser Ser
        115                 120

<210> SEQ ID NO 8
<211> LENGTH: 360
<212> TYPE: DNA
<213> ORGANISM: Artificial Sequence
<220> FEATURE:
<223> OTHER INFORMATION: synthetic polynucleotide

<400> SEQUENCE: 8
caggttcagc tgcagcagtc tggacctgag ctggtgaagc ctggggcttt agtgaagata      60
tcctgcaagg cttctggtta caccttcaca agctacgata taaactgggt gaagcagagg     120
cctggacagg gacttgagtg gattggatgg atttatcctg agatggtag tactaagtac      180 aatgagaaat tcaagggcaa ggccacactg actgcagaca atcctccag cacagcctac      240 atgcagctca gcagcctgac ttctgagaac tctgcagtct atttctgtgc aagagggggc     300
tataggtacg acgaggctat ggactactgg ggtcaaggga ccacggtcac cgtctcctca     360

<210> SEQ ID NO 9
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 9

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Leu
            100                 105                 110

Lys Arg

<210> SEQ ID NO 10
<211> LENGTH: 342
<212> TYPE: DNA
<213> ORGANISM: Artificial Sequence
<220> FEATURE:
<223> OTHER INFORMATION: synthetic polynucleotide

<400> SEQUENCE: 10
gacattgtga tgacacagtc tccatcctcc ctgagtgtgt cagcaggaga gaaggtcact      60
atgagctgca agtccagtca gagtctgtta acagtggaa atcaaaagaa ctacttggcc     120
tggtaccagc agaaaccagg gcagcctcct aaactgttga tctacggggc atccactagg     180
gaatctgggg tccctgatcg cttcacaggc agtggatctg gaaccgattt cactcttacc     240
atcagcagtg tgcaggctga agacctggca gtttattact gtcagaatga tcatagttat     300
ccgctcacgt tcggtgctgg gaccaagctg gagctgaaac gg    342

<210> SEQ ID NO 11
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 11

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Phe Ser Tyr Gly Asn Ser Phe Ala Tyr Trp Gly Gln Gly Thr
            100                 105                 110

Thr Val Thr Val Ser Ser
        115

<210> SEQ ID NO 12
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 12
cagatccagt tggtgcagtc tggacctgag ctgaagaagc ctggagagac agtcaagatc    60
tcctgcaagg cttctgggta taccttcaca aactatggaa tgaactgggt gaagcaggct    120
ccaggaaagg gtttaaagtg gatgggctgg ataaacacca acactggaga gccaacatat    180
gctgaagagt tcaagggacg gtttgccttc tctttggaaa cctctgccag cactgcctat    240
ttgcagatca caacctcaa aaatgaggac acggctacat atttctgtgc tagattctct    300
tatggtaact cctttgctta ctggggccaa gggaccacgg tcaccgtctc ctca    354

<210> SEQ ID NO 13
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 13

Asp Ile Val Met Thr Gln Ser Pro Ser Ser Leu Thr Val Thr Pro Gly
1               5                   10                  15

Glu Lys Val Thr Met Thr Cys Lys Ser Ser Gln Ser Leu Phe Asn Ser
            20                  25                  30

Gly Asn Gln Lys Asn Tyr Leu Thr Trp Tyr Gln Gln Arg Pro Gly Gln
        35                  40                  45

Pro Pro Lys Met Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Phe Tyr Cys Gln Asn
                85                  90                  95

Ala Tyr Ser Phe Pro Tyr Thr Phe Gly Gly Gly Thr Lys Leu Glu Ile
            100                 105                 110

Lys Arg

<210> SEQ ID NO 14
<211> LENGTH: 342
<212> TYPE: DNA
<213> ORGANISM: Artificial Sequence
<220> FEATURE:
<223> OTHER INFORMATION: synthetic polynucleotide

<400> SEQUENCE: 14
gacattgtga tgacacagtc tccatcctcc ctgactgtga caccaggaga gaaggtcact     60
atgacctgca gtccagtca gagtttgttt aatagtggaa atcaaaagaa ctacttgacc    120
tggtaccaac agagacctgg ccagccccct aaaatgttga tctactgggc atccactagg    180
gaatctgggg tccctgatcg cttcacaggc agtggatctg gaacagattt cactctcacc    240
atcagcagtg tgcaggctga agacctggca gttttttact gtcagaatgc ttatagtttt    300
ccgtacacgt tcggagggg gaccaagctg gaaataaaac gg                       342

<210> SEQ ID NO 15
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 15

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Asn Trp His Trp Ile Arg Gln Phe Pro Gly Asn Lys Met Glu Trp
        35                  40                  45

Met Gly Tyr Ile His Tyr Thr Gly Ser Thr Asn Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Thr Asp Asp Thr Ala Thr Tyr Tyr Cys
                85                  90                  95

Thr Arg Ile Tyr Asn Gly Asn Ser Phe Pro Tyr Trp Gly Gln Gly Thr
            100                 105                 110

Ser Val Thr Val Ser Ser
        115

<210> SEQ ID NO 16
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 16
gatgtgcaac ttcaggagtc aggacctgac ctggtgaaac cttctcagtc actttcactc     60

```
acctgcactg tcactggcta ctccatcacc agtggttata actggcactg gatccggcag    120
tttccaggaa acaaaatgga atggatgggc tacatacact acactggtag cactaattac    180
aacccatctc tcagaagtcg aatctctatc actcgagaca catccaagaa ccagttcttc    240
ctgcagttga attctgtgac cactgatgac acagccacat attactgtac aagaatctac    300
aatggtaact cttttcctta ctggggccaa ggaacctcag tcaccgtctc ctca          354
```

<210> SEQ ID NO 17
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 17

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asp Pro Ser Ser Gly Tyr Thr Asn Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser
        115
```

<210> SEQ ID NO 18
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 18

```
caggtccagc tgcagcagtc tggggctgaa ctggcaagac ctggggcctc agtgaagatg     60
tcctgcaagg cttctggcta cacctttact agctacacga tgcactgggt aaaacagagg    120
cctggacagg gtctggaatg gattggatac attgacccta gcagtggtta tactaattac    180
aatcagaagt tcaaggacaa ggccacattg actgcagaca atcctccag cacagcctac     240 atgcaactga gcagcctgac atctgaggac tctgcagtct attactgtgc aagaatctac    300
tatggtaact cgtttgctta ctggggccaa gggaccacgg tcaccgtctc ctca          354
```

<210> SEQ ID NO 19
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 19

```
Gln Val Gln Leu Gln Gln Ser Gly Ala Glu Leu Ala Arg Pro Gly Ala
1               5                   10                  15
```

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ala Ser Gly Tyr Thr Asn Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ile Tyr Tyr Gly Asn Ser Phe Ala Tyr Trp Gly Gln Gly Thr
            100                 105                 110

Thr Val Thr Val Ser Ser
            115

<210> SEQ ID NO 20
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 20
caggtccagc tgcagcagtc tggggctgaa ctggcaagac ctggggcctc agtgaagatg      60
tcctgcaagg cttctggcta cacctttact agctacacga tgcactgggt aaaacagagg     120
cctggacagg gtctggaatg gattggatac attaatcctg ccagtggtta tactaattac     180
aatcagaagt tcaaggacaa ggccacattg actgcagaca atcctccag cacagcctac      240 atgcaactga gcagcctgac atctgaggac tctgcagtct attactgtgc aagaatctac     300
tatggtaact cgtttgctta ctggggccaa gggaccacgg tcaccgtctc ctca           354

<210> SEQ ID NO 21
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gly Gly Thr Lys Val Glu Ile
            100                 105                 110

Lys Arg

<210> SEQ ID NO 22

<211> LENGTH: 342
<212> TYPE: DNA
<213> ORGANISM: Artificial Sequence
<220> FEATURE:
<223> OTHER INFORMATION: synthetic polynucleotide

<400> SEQUENCE: 22

| | | |
|---|---|---:|
| gacatcgtga tgacccagag ccccgacagc ctggccgtga gcctgggcga gcgggccacc | | 60 |
| atcaactgca agagcagcca gagcctgctg aacagcggca accagaagaa ctacctgacc | | 120 |
| tggtaccagc agaagcccgg ccagccccccc aagctgctga tctactgggc cagcacccgg | | 180 |
| gagagcggcg tgcccgaccg gttcagcggc agcggcagcg gcaccgactt caccctgacc | | 240 |
| atcagcagcc tgcaggccga ggacgtggcc gtgtactact gccagaacga ctacagctac | | 300 |
| cccctgacct tcggcggcgg caccaaggtg gagatcaagc gg | | 342 |

<210> SEQ ID NO 23
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser
        115

<210> SEQ ID NO 24
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 24

| | | |
|---|---|---:|
| caggtgcagc tggtgcagag cggcgccgag gtgaagaagc ccggcgccag cgtgaaggtg | | 60 |
| agctgcaagg ccagcggcta caccttcacc agctacacca tgcactgggt gcggcaggcc | | 120 |
| cccggccagg gcctggagtg gatgggctac atcaaccccg ccagcggcta caccaactac | | 180 |
| aaccagaagt tcaaggaccg ggtgaccatg acccgggaca ccagcaccag caccgcctac | | 240 |
| atggagctga gcagcctgcg gagcgaggac accgccgtgt actactgcgc ccggatctac | | 300 |
| tacggcaaca gcttcgccta ctggggccag ggcaccctgg tgaccgtgag cagc | | 354 |

<210> SEQ ID NO 25
<211> LENGTH: 114

```
<212> TYPE: PRT
<213> ORGANISM: Artificial Sequence
<220> FEATURE:
<223> OTHER INFORMATION: synthetic polypeptide

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ser Phe Pro Tyr Thr Phe Gly Gly Gly Thr Lys Leu Glu Ile
            100                 105                 110

Lys Arg

<210> SEQ ID NO 26
<211> LENGTH: 342
<212> TYPE: DNA
<213> ORGANISM: Artificial Sequence
<220> FEATURE:
<223> OTHER INFORMATION: synthetic polynucleotide

<400> SEQUENCE: 26
gacatcgtga tgacccagag ccccgacagc ctggccgtga gcctgggcga gcgggccacc        60
atcaactgca agagcagcca gagcctgttc aacagcggca accagaagaa ctacctgacc       120
tggtaccagc agaagcccgg ccagcccccc aagctgctga tctactgggc cagcacccgg       180
gagagcggcg tgcccgaccg gttcagcggc agcggcagcg gcaccgactt caccctgacc       240
atcagcagcc tgcaggccga ggacgtggcc gtgtactact gccagaacgc ctacagcttc       300
ccctacacct tcggcggcgg caccaagctg gagatcaagc gg                          342

<210> SEQ ID NO 27
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

Ala Arg Ile Tyr Asn Gly Asn Ser Phe Pro Tyr Trp Gly Gln Gly Thr
            100                 105                 110

Thr Val Thr Val Ser Ser
        115

<210> SEQ ID NO 28
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 28
caggtgcagc tgcaggagag cggccccggc ctggtgaagc ccagccagac cctgagcctg      60
acctgcaccg tgagcggcgg cagcatcagc agcggctaca actggcactg gatccggcag     120
ccccccggca agggcctgga gtggatcggc tacatccact acaccggcag caccaactac     180
aaccccgccc tgcggagccg ggtgaccatc agcgtggaca ccagcaagaa ccagttcagc     240
ctgaagctga gcagcgtgac cgccgccgac accgccgtgt actactgcgc ccggatctac     300
aacggcaaca gcttccccta ctggggccag ggcaccaccg tgaccgtgag cagc           354

<210> SEQ ID NO 29
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 29

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser
        115

<210> SEQ ID NO 30
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 30
caggtgcagc tgcaggagag cggccccggc ctgatcaagc ccagccagac cctgagcctg      60
acctgcaccg tgagcggcgg cagcatcagc agcggctaca actggcactg gatccggcag     120
ccccccggca agggcctgga gtggatcggc tacatccact acaccggcag caccaactac     180

```
aaccccgccc tgcggagccg ggtgaccatc agcgtggaca ccagcaagaa ccagttcagc    240
ctgaagctga gcagcgtgac cgccgccgac accgccatct actactgcgc ccggatctac    300
aacggcaaca gcttccccta ctggggccag ggcaccaccg tgaccgtgag cagc          354
```

<210> SEQ ID NO 31
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 31

Ser Tyr Thr Met His
1               5

<210> SEQ ID NO 32
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 32

Tyr Ile Asn Pro Ser Ser Gly Tyr Thr Asn Tyr Asn Gln Lys Phe Lys
1               5                   10                  15

Asp

<210> SEQ ID NO 33
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 33

Ile Tyr Tyr Gly Asn Ser Phe Ala Tyr
1               5

<210> SEQ ID NO 34
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 34

Lys Ser Ser Gln Ser Leu Leu Asn Ser Gly Asn Gln Lys Asn Tyr Leu
1               5                   10                  15

Thr

<210> SEQ ID NO 35
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 35

Trp Ala Ser Thr Arg Glu Ser
1               5

<210> SEQ ID NO 36
<211> LENGTH: 9
<212> TYPE: PRT

```
<213> ORGANISM: Artificial Sequence
<220> FEATURE:
<223> OTHER INFORMATION: synthetic polypeptide

<400> SEQUENCE: 36

Gln Asn Asp Tyr Ser Tyr Pro Leu Thr
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 37

Ser Tyr Asp Ile Asn
1               5

<210> SEQ ID NO 38
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 38

Trp Ile Tyr Pro Gly Asp Gly Ser Thr Lys Tyr Asn Glu Lys Phe Lys
1               5                   10                  15

Gly

<210> SEQ ID NO 39
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 39

Gly Gly Tyr Arg Tyr Asp Glu Ala Met Asp Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 40

Ser Ala Ser Ser Ser Ile Ser Tyr Met His
1               5                   10

<210> SEQ ID NO 41
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 41

Asp Thr Ser Lys Leu Ala Ser
1               5

<210> SEQ ID NO 42
<211> LENGTH: 9
```

```
<212> TYPE: PRT
<213> ORGANISM: Artificial Sequence
<220> FEATURE:
<223> OTHER INFORMATION: synthetic polypeptide

<400> SEQUENCE: 42

His Gln Arg Ser Ser Tyr Pro Tyr Thr
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 43

Asn Tyr Gly Met Asn
1               5

<210> SEQ ID NO 44
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 44

Trp Ile Asn Thr Asn Thr Gly Glu Pro Thr Tyr Ala Glu Glu Phe Lys
1               5                   10                  15

Gly

<210> SEQ ID NO 45
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 45

Phe Ser Tyr Gly Asn Ser Phe Ala Tyr
1               5

<210> SEQ ID NO 46
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 46

Lys Ser Ser Gln Ser Leu Leu Asn Ser Gly Asn Gln Lys Asn Tyr Leu
1               5                   10                  15

Ala

<210> SEQ ID NO 47
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 47

Gly Ala Ser Thr Arg Glu Ser
1               5
```

```
<210> SEQ ID NO 48
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 48

Gln Asn Asp His Ser Tyr Pro Leu Thr
1               5

<210> SEQ ID NO 49
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 49

Ser Gly Tyr Asn Trp His
1               5

<210> SEQ ID NO 50
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 50

Tyr Ile His Tyr Thr Gly Ser Thr Asn Tyr Asn Pro Ser Leu Arg Ser
1               5                   10                  15

<210> SEQ ID NO 51
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 51

Ile Tyr Asn Gly Asn Ser Phe Pro Tyr
1               5

<210> SEQ ID NO 52
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 52

Lys Ser Ser Gln Ser Leu Phe Asn Ser Gly Asn Gln Lys Asn Tyr Leu
1               5                   10                  15

Thr

<210> SEQ ID NO 53
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 53

Trp Ala Ser Thr Arg Glu Ser
1               5
```

<210> SEQ ID NO 54
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 54

Gln Asn Ala Tyr Ser Phe Pro Tyr Thr
1               5

<210> SEQ ID NO 55
<211> LENGTH: 261
<212> TYPE: PRT
<213> ORGANISM: Homo sapiens

<400> SEQUENCE: 55

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
                20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
        50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 56
<211> LENGTH: 786
<212> TYPE: DNA
<213> ORGANISM: Homo sapiens

<400> SEQUENCE: 56

```
atggccgtga ctgcctgtca gggcttgggg ttcgtggttt cactgattgg gattgcgggc    60
atcattgctg ccacctgcat ggaccagtgg agcacccaag acttgtacaa caaccccgta   120
acagctgttt tcaactacca ggggctgtgg cgctcctgtg tccgagagag ctctggcttc   180
accgagtgcc ggggctactt caccctgctg gggctgccag ccatgctgca ggcagtgcga   240
gccctgatga tcgtaggcat cgtcctgggt gccattggcc tcctggtatc catctttgcc   300
ctgaaatgca tccgcattgg cagcatggag gactctgcca agccaacat gacactgacc    360
tccgggatca tgttcattgt ctcaggtctt tgtgcaattg ctggagtgtc tgtgtttgcc   420
aacatgctgg tgactaactt ctggatgtcc acagctaaca tgtacaccgg catgggtggg   480
atggtgcaga ctgttcagac caggtacaca tttggtgcgg ctctgttcgt gggctgggtc   540
gctggaggcc tcacactaat tgggggtgtg atgatgtgca tcgcctgccg gggcctggca   600
ccagaagaaa ccaactacaa agccgtttct tatcatgcct caggccacag tgttgcctac   660
aagcctggag gcttcaaggc cagcactggc tttgggtcca caccaaaaa caagaagata    720
tacgatggag gtgcccgcac agaggacgag gtacaatctt atccttccaa gcacgactat   780
gtgtaa                                                             786
```

<210> SEQ ID NO 57
<211> LENGTH: 261
<212> TYPE: PRT
<213> ORGANISM: Homo sapiens

<400> SEQUENCE: 57

```
Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220
```

Phe Lys Ala Ser Thr Gly Phe Gly Ser Asn Thr Lys Asn Lys Ile
225                 230                 235                 240

Tyr Asp Gly Gly Ala Arg Thr Glu Asp Glu Val Gln Ser Tyr Pro Ser
            245                 250                 255

Lys His Asp Tyr Val
            260

<210> SEQ ID NO 58
<211> LENGTH: 786
<212> TYPE: DNA
<213> ORGANISM: Homo sapiens

<400> SEQUENCE: 58
atgtccacca ccacatgcca agtggtggcg ttcctcctgt ccatcctggg gctggccggc      60
tgcatcgcgg ccaccgggat ggacatgtgg agcacccagg acctgtacga caaccccgtc     120
acctccgtgt tccagtacga agggctctgg aggagctgcg tgaggcagag ttcaggcttc     180
accgaatgca ggcctatttt caccatcctg ggacttccag ccatgctgca ggcagtgcga     240
gccctgatga tcgtaggcat cgtcctgggt gccattggcc tcctggtatc catctttgcc     300
ctgaaatgca tccgcattgg cagcatggag gactctgcca agccaacatg acactgacc     360 tccgggatca tgttcattgt ctcaggtctt tgtgcaattg ctggagtgtc tgtgtttgcc     420
aacatgctgg tgactaactt ctggatgtcc acagctaaca tgtacaccgg catgggtggg     480
atggtgcaga ctgttcagac caggtacaca tttggtgcgg ctctgttcgt gggctgggtc     540
gctggaggcc tcacactaat tggggtgtgt atgatgtgca tcgcctgccg gggcctggca     600
ccagaagaaa ccaactacaa agccgtttct tatcatgcct caggccacag tgttgcctac     660
aagcctggag gcttcaaggc cagcactggc tttgggtcca acaccaaaaa caagaagata     720
tacgatggag gtgcccgcac agaggacgag gtacaatctt atccttccaa gcacgactat     780
gtgtaa                                                                786

<210> SEQ ID NO 59
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 60
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 60
caggtgcagc tggtgcagag cggcgccgag gtgaagaagc ccggcgccag cgtgaaggtg      60
agctgcaagg ccagcggcta caccttcacc agctacacca tgcactgggt gcggcaggcc     120
cccggccagg gcctggagtg gatgggctac atcaaccccg ccagcggcta caccaactac     180
aaccagaagt tcaaggaccg ggtgaccatg acccgggaca ccagcaccag caccgcctac     240

```
atggagctga gcagcctgcg gagcgaggac accgccgtgt actactgcgc ccggatctac    300
tacggcaaca gcttcgccta ctggggccag ggcaccctgg tgaccgtgag cagcgctagc    360
accaaaggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttccggctg tcctacagtc ctcaggactc     540
tactccctca gcagcgtggt gaccgtgccc tccagcagct gggcaccca gacctacatc     600
tgcaacgtga atcacaagcc cagcaacacc aaggtggaca gaaagttga gcccaaatct     660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 61
<211> LENGTH: 220
<212> TYPE: PRT
<213> ORGANISM: Artificial Sequence
<220> FEATURE:
<223> OTHER INFORMATION: synthetic polypeptide

<400> SEQUENCE: 61

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
            165                 170                 175
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220
```

<210> SEQ ID NO 62
<211> LENGTH: 660
<212> TYPE: DNA
<213> ORGANISM: Artificial Sequence
<220> FEATURE:
<223> OTHER INFORMATION: synthetic polynucleotide

<400> SEQUENCE: 62

```
gacatcgtga tgacccagag ccccgacagc ctggccgtga gcctgggcga gcgggccacc    60
atcaactgca agagcagcca gagcctgctg aacagcggca accagaagaa ctacctgacc   120
tggtaccagc agaagcccgg ccagcccccc aagctgctga tctactgggc cagcacccgg   180
gagagcggcg tgcccgaccg gttcagcggc agcggcagcg gcaccgactt caccctgacc   240
atcagcagcc tgcaggccga ggacgtggcc gtgtactact gccagaacga ctacagctac   300
cccctgacct cggcggcgg caccaaggtg gagatcaagc ggacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc   600 gaagtcaccc atcagggcct gagctcgccc gtcacaaaga gcttcaacag gggagagtgt   660
```

<210> SEQ ID NO 63
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 63

```
Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 64
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 64

```
caggtgcagc tgcaggagag cggccccggc ctgatcaagc ccagccagac cctgagcctg      60
acctgcaccg tgagcggcgg cagcatcagc agcggctaca actggcactg gatccggcag     120
ccccccggca agggcctgga gtggatcggc tacatccact acaccggcag caccaactac     180
aaccccgccc tgcggagccg ggtgaccatc agcgtggaca ccagcaagaa ccagttcagc     240
ctgaagctga gcagcgtgac cgccgccgac accgccatct actactgcgc ccggatctac     300
aacggcaaca gcttccccta ctggggccag ggcaccaccg tgaccgtgag cagcgctagc     360
```

```
accaaaggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct tgggcaccca gacctacatc    600
tgcaacgtga atcacaagcc cagcaacacc aaggtggaca agaaagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca agccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 65
<211> LENGTH: 220
<212> TYPE: PRT
<213> ORGANISM: Artificial Sequence
<220> FEATURE:
<223> OTHER INFORMATION: synthetic polypeptide

<400> SEQUENCE: 65

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ser Phe Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
```

```
                    180                 185                 190
Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 66
<211> LENGTH: 660
<212> TYPE: DNA
<213> ORGANISM: Artificial Sequence
<220> FEATURE:
<223> OTHER INFORMATION: synthetic polynucleotide

<400> SEQUENCE: 66
gacatcgtga tgacccagag ccccgacagc ctggccgtga gcctgggcga gcgggccacc      60
atcaactgca agagcagcca gagcctgttc aacagcggca accagaagaa ctacctgacc     120
tggtaccagc agaagcccgg ccagccccc aagctgctga tctactgggc cagcacccgg      180
gagagcggcg tgcccgaccg gttcagcggc agcggcagcg gcaccgactt caccctgacc     240
atcagcagcc tgcaggccga ggacgtggcc gtgtactact gccagaacgc ctacagcttc     300
ccctacacct tcggcggcgg caccaagctg gagatcaagc ggacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660

<210> SEQ ID NO 67
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 67

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 68
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 68
caggtgcagc tgcaggagag cggccccggc ctgatcaagc ccagccagac cctgagcctg      60
acctgcaccg tgagcggcgg cagcatcagc agcggctaca actggcactg gatccggcag     120
ccccccggca gggcctggaa gtggatcggc tacatccact acaccggcag caccaactac     180
aaccccgccc tgcggagccg ggtgaccatc agcgtggaca ccagcaagaa ccagttcagc     240
ctgaagctga gcagcgtgac cgccgccgac accgccatct actactgcgc ccggatctac     300
aacggcaaca gcttccccta ctggggccag ggcaccaccg tgaccgtgag cagcgctagc     360
accaaaggcc catcggtctt ccccctggca ccctcctcca agagcacctc tgggggcaca     420

```
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc     600 tgcaacgtga atcacaagcc cagcaacacc aaggtggaca gaaagttga gcccaaatct     660 tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca agccgcggg aggagcagta acagcacg      900 taccgtgtgg tcagcgtcct caccgtcctg caccaggact ggctgaatgg caaggagtac    960
aagtgcaagg tctccaacaa agccctccca gccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                           1344
```

<210> SEQ ID NO 69
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 69

Met Ala Leu Pro Val Thr Ala Leu Leu Leu Pro Leu Ala Leu Leu Leu
1               5                   10                  15

His Ala Ala Arg Pro
            20

<210> SEQ ID NO 70
<211> LENGTH: 63
<212> TYPE: DNA
<213> ORGANISM: Artificial Sequence
<220> FEATURE:
<223> OTHER INFORMATION: synthetic polynucleotide

<400> SEQUENCE: 70
atggccttac cagtgaccgc cttgctcctg ccgctggcct tgctgctcca cgccgccagg    60
ccg                                                                  63

<210> SEQ ID NO 71
<211> LENGTH: 45
<212> TYPE: PRT
<213> ORGANISM: Artificial Sequence
<220> FEATURE:
<223> OTHER INFORMATION: synthetic polypeptide

<400> SEQUENCE: 71

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

```
              35                  40                  45
```

<210> SEQ ID NO 72
<211> LENGTH: 135
<212> TYPE: DNA
<213> ORGANISM: Artificial Sequence
<220> FEATURE:
<223> OTHER INFORMATION: synthetic polynucleotide

<400> SEQUENCE: 72
accacgacgc cagcgccgcg accaccaaca ccggcgccca ccatcgcgtc gcagcccctg     60
tccctgcgcc cagaggcgtg ccggccagcg gcggggggcg cagtgcacac gaggggggctg    120 gacttcgcct gtgat                                                    135

<210> SEQ ID NO 73
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 73

Phe Trp Val Leu Val Val Val Gly Gly Val Leu Ala Cys Tyr Ser Leu
1               5                  10                  15

Leu Val Thr Val Ala Phe Ile Ile Phe Trp Val
            20                  25

<210> SEQ ID NO 74
<211> LENGTH: 81
<212> TYPE: DNA
<213> ORGANISM: Artificial Sequence
<220> FEATURE:
<223> OTHER INFORMATION: synthetic polynucleotide

<400> SEQUENCE: 74
ttttgggtgc tggtggtggt tggtggagtc ctggcttgct atagcttgct agtaacagtg     60
gcctttatta ttttctgggt g                                              81

<210> SEQ ID NO 75
<211> LENGTH: 41
<212> TYPE: PRT
<213> ORGANISM: Artificial Sequence
<220> FEATURE:
<223> OTHER INFORMATION: synthetic polypeptide

<400> SEQUENCE: 75

Arg Ser Lys Arg Ser Arg Leu Leu His Ser Asp Tyr Met Asn Met Thr
1               5                  10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 76
<211> LENGTH: 123
<212> TYPE: DNA
<213> ORGANISM: Artificial Sequence
<220> FEATURE:
<223> OTHER INFORMATION: synthetic polynucleotide

<400> SEQUENCE: 76
aggagtaaga ggagcaggct cctgcacagt gactacatga acatgactcc ccgccgcccc     60

```
gggccaaccc gcaagcatta ccagccctat gccccaccac gcgacttcgc agcctatcgc    120
tcc                                                                 123
```

<210> SEQ ID NO 77
<211> LENGTH: 113
<212> TYPE: PRT
<213> ORGANISM: Artificial Sequence
<220> FEATURE:
<223> OTHER INFORMATION: synthetic polypeptide

<400> SEQUENCE: 77

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 78
<211> LENGTH: 339
<212> TYPE: DNA
<213> ORGANISM: Artificial Sequence
<220> FEATURE:
<223> OTHER INFORMATION: synthetic polynucleotide

<400> SEQUENCE: 78

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaaagccgca gagaaggaag accctcagga aggcctgtac   180
aatgaactgc agaaagataa gatggcgagg cctacagtg agattgggat gaaaggcgag   240
cgccggaggg gcaaggggca cgatggcctt taccagggtc tcagtacagc caccaaggac   300
acctacgacg cccttcacat gcaggccctg cccctcgc                          339
```

<210> SEQ ID NO 79
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 79

```
Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 80
<211> LENGTH: 63
<212> TYPE: DNA

-continued

```
<213> ORGANISM: Artificial Sequence
<220> FEATURE:
<223> OTHER INFORMATION: synthetic polynucleotide

<400> SEQUENCE: 80
atctacatct gggcgccctt ggccgggact tgtggggtcc ttctcctgtc actggttatc    60
acc                                                                  63

<210> SEQ ID NO 81
<211> LENGTH: 42
<212> TYPE: PRT
<213> ORGANISM: Artificial Sequence
<220> FEATURE:
<223> OTHER INFORMATION: synthetic polypeptide

<400> SEQUENCE: 81

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 82
<211> LENGTH: 126
<212> TYPE: DNA
<213> ORGANISM: Artificial Sequence
<220> FEATURE:
<223> OTHER INFORMATION: synthetic polynucleotide

<400> SEQUENCE: 82
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 83
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 83

Tyr Ile Asp Pro Ser Ser Gly Tyr Thr Asn Tyr Asn Gln Lys Phe Lys
1               5                   10                  15

Asp

<210> SEQ ID NO 84
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 84

Tyr Ile Asn Pro Ala Ser Gly Tyr Thr Asn Tyr Asn Gln Lys Phe Lys
1               5                   10                  15

Asp

<210> SEQ ID NO 85
<211> LENGTH: 16
<212> TYPE: PRT
```

<213> ORGANISM: Artificial Sequence
<220> FEATURE:
<223> OTHER INFORMATION: synthetic polypeptide

<400> SEQUENCE: 85

Tyr Ile His Tyr Thr Gly Ser Thr Asn Tyr Asn Pro Ala Leu Arg Ser
1               5                   10                  15

<210> SEQ ID NO 86
<211> LENGTH: 220
<212> TYPE: PRT
<213> ORGANISM: Artificial Sequence
<220> FEATURE:
<223> OTHER INFORMATION: synthetic polypeptide

<400> SEQUENCE: 86

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 87
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 87

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

```
Gly Trp Ile Asn Thr Asn Thr Gly Glu Pro Thr Tyr Ala Glu Glu Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Leu Gly Phe Gly Asn Ala Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 88
<211> LENGTH: 220
```

<212> TYPE: PRT
<213> ORGANISM: Artificial Sequence
<220> FEATURE:
<223> OTHER INFORMATION: synthetic polypeptide

<400> SEQUENCE: 88

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 89
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 89

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 90
<211> LENGTH: 3075
<212> TYPE: DNA
<213> ORGANISM: Artificial Sequence
<220> FEATURE:
<223> OTHER INFORMATION: synthetic polynucleotide

<400> SEQUENCE: 90 atggcttac cagtgaccgc cttgctcctg ccgctggcct tgctgctcca cgccgccagg      60
ccgcaggtgc agctgcagga gagcggcccc ggctggtga agcccagcca gaccctgagc     120
ctgacctgca ccgtgagcgg cggcagcatc agcagcggct acaactggca ctggatccgg     180

```
cagcccccg   gcaagggcct   ggagtggatc   ggctacatcc   actacaccgg   cagcaccaac        240
tacaaccccg   ccctgcggag   ccgggtgacc   atcagcgtgg   acaccagcaa   gaaccagttc        300
agcctgaagc   tgagcagcgt   gaccgccgcc   gacaccgccg   tgtactactg   cgcccggatc        360
tacaacggca   cagcttccc   ctactggggc   cagggcacca   ccgtgaccgt   gagcagcggt        420
ggaggcggtt   caggcggagg   tggttctggc   ggtggcggat   cggacatcgt   gatgacccag        480
agccccgaca   gcctggccgt   gagcctgggc   gagcgggcca   ccatcaactg   caagagcagc        540
cagagcctgt   tcaacagcgg   caaccagaag   aactacctga   cctggtacca   gcagaagccc        600
ggccagcccc   ccaagctgct   gatctactgg   gccagcaccc   gggagagcgg   cgtgcccgac        660
cggttcagcg   gcagcggcag   cggcaccgac   ttcaccctga   ccatcagcag   cctgcaggcc        720
gaggacgtgg   ccgtgtacta   ctgccagaac   gcctacagct   cccctacac   cttcggcggc        780 ggcaccaagc   tggagatcaa   gcggaccacg   acgccagcgc   cgcgaccacc   aacaccggcg        840
cccaccatcg   cgtcgcagcc   cctgtccctg   cgcccagagg   cgtgccggcc   agcggcgggg        900
ggcgcagtgc   acacgagggg   gctggacttc   gcctgtgatt   tttgggtgct   ggtggtggtt        960
ggtggagtcc   tggcttgcta   tagcttgcta   gtaacagtgg   cctttattat   tttctgggtg       1020
aggagtaaga   ggagcaggct   cctgcacagt   gactacatga   acatgactcc   ccgccgcccc       1080
gggccaaccc   gcaagcatta   ccagccctat   gccccaccac   gcgacttcgc   agcctatcgc       1140
tccagagtga   agttcagcag   gagcgcagac   gccccgcgt   accagcaggg   ccagaaccag       1200
ctctataacg   agctcaatct   aggacgaaga   gaggagtacg   atgttttgga   caagagacgt       1260
ggccgggacc   ctgagatggg   gggaaagccg   cagagaagga   agaaccctca   ggaaggcctg       1320
tacaatgaac   tgcagaaaga   taagatggcg   gaggcctaca   gtgagattgg   gatgaaaggc       1380
gagcgccgga   ggggcaaggg   gcacgatggc   ctttaccagg   gtctcagtac   agccaccaag       1440
gacacctacg   acgcccttca   catgcaggcc   ctgccccctc   gctaggtcga   caatcaacct       1500
ctggattaca   aaatttgtga   aagattgact   ggtattctta   actatgttgc   tccttttacg       1560
ctatgtggat   acgctgcttt   aatgcctttg   tatcatgcta   ttgcttcccg   tatggctttc       1620
attttctcct   ccttgtataa   atcctggttg   ctgtctcttt   atgaggagtt   gtggcccgtt       1680
gtcaggcaac   gtggcgtggt   gtgcactgtg   tttgctgacg   caacccccac   tggttggggc       1740
attgccacca   cctgtcagct   cctttccggg   actttcgctt   tccccctccc   tattgccacg       1800
gcggaactca   tcgccgcctg   ccttgcccgc   tgctggacag   gggctcggct   gttgggcact       1860
gacaattccg   tggtgttgtc   ggggaagctg   acgtcctttc   catggctgct   cgcctgtgtt       1920
gccacctgga   ttctgcgcgg   gacgtccttc   tgctacgtcc   cttcggccct   caatccagcg       1980
gaccttcctt   cccgcggcct   gctgccggct   ctgcggcctc   ttccgcgtct   tcgccttcgc       2040
cctcagacga   gtcggatctc   cctttgggcc   gcctccccgc   ctggaattcg   ctagcctcga       2100
gctcacacaa   aaaaccaaca   cacagatgta   atgaaaataa   agatatttta   ttgcggccgc       2160
tttagtttcg   gaggtaacct   gtaagtctgt   taatgaagta   aaagttcctt   aggattccca       2220
ctctgactat   ggtccaggca   cagtgactgt   actccttggc   cttcaggtaa   tgcagaatcc       2280
tcccataata   tcttttcagg   tgcagactgc   tcatgagttt   cccctggtg   aaatcttctt       2340 tctccagttt   ttcttccagg   actgtcttca   gatggtttat   ctgatgatag   acattagcca       2400
ggaggttctc   aacaatagtc   tcattccagc   cagtgctaga   tgaatcttgt   ctgaaaatag       2460
caaagatgtt   ctggagcatc   tcatagatgg   tcaatgcggc   gtcctccttc   tggaactgct       2520
```

```
gcagctgctt aatctcctca gggatgtcaa agttcatcct gtccttgagg cagtattcaa    2580
gcctcccatt caattgccac aggagcttct gacactgaaa attgctgctt ctttgtagga    2640
atccaagcaa gttgtagctc atggaaagag ctgtagtgga aagcacaac aggagagcaa     2700 tttggaggag acacttgttg gtcatggtgg cgaccggtag cgctaggtca tatgcaggag    2760
ttgaggttac tgtgagtagt gattaaagag agtgataggg aactcttgaa caagagatgc    2820
aatttatact gttaattctg gaaaatatt atgggggtgt caaatgtcc cgggacaatt      2880 gacgccttct gtatgaaaca gttttcctc cacgccttct gtatgaaaca gttttcctc     2940 cacgccttct gtatgaaaca gttttcctc cgtcgaggac aattgacgcc ttctgtatga     3000
aacagttttt cctccacgcc ttctgtatga aacagttttt cctccacgcc ttctgtatga   3060
aacagttttt cctcc                                                    3075

<210> SEQ ID NO 91
<211> LENGTH: 3075
<212> TYPE: DNA
<213> ORGANISM: Artificial Sequence
<220> FEATURE:
<223> OTHER INFORMATION: synthetic polynucleotide

<400> SEQUENCE: 91
atggccttac cagtgaccgc cttgctcctg ccgctggcct tgctgctcca cgccgccagg      60
ccgcaggtgc agctgcagga gagcggcccc ggcctgatca gcccagcca ccctgagc       120 ctgacctgca ccgtgagcgg cggcagcatc agcagcggct acaactggca ctggatccgg    180
cagccccccg gcaagggcct ggagtggatc ggctacatcc actacaccgg cagcaccaac    240
tacaaccccg ccctgcggag ccgggtgacc atcagcgtgg acaccagcaa gaaccagttc    300
agcctgaagc tgagcagcgt gaccgccgcc gacaccgcca tctactactg cgcccggatc    360
tacaacggca acagcttccc ctactgggc cagggcacca ccgtgaccgt gagcagcggt    420
ggaggcggtt caggcggagg tggttctggc ggtggcggat cggacatcgt gatgacccag    480
agccccgaca gcctggccgt gagcctgggc gagcgggcca ccatcaactg caagagcagc    540
cagagcctgt tcaacagcgg caaccagaag aactacctga cctggtacca gcagaagccc    600
ggccagcccc ccaagctgct gatctactgg gccagcaccc gggagagcgg cgtgcccgac    660
cggttcagcg gcagcggcag cggcaccgac ttcaccctga ccatcagcag cctgcaggcc    720
gaggacgtgg ccgtgtacta ctgccagaac gcctacagct ccccctacac cttcggcggc    780
ggcaccaagc tggagatcaa gcggaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgatt tttgggtgct ggtggtggtt    960
ggtggagtcc tggcttgcta tagcttgcta gtaacagtgg cctttattat tttctgggtg   1020
aggagtaaga ggagcaggct cctgcacagt gactacatga acatgactcc ccgccgcccc   1080
gggccaaccc gcaagcatta ccagccctat gccccaccac gcgacttcgc agcctatcgc   1140
tccagagtga agttcagcag gagcgcagac gcccccgcgt accagcaggg ccagaaccag   1200
ctctataacg agctcaatct aggacgaaga gaggagtacg atgttttgga caagagacgt   1260
ggccgggacc ctgagatggg gggaaagccg cagagaagga gaacccctca ggaaggcctg   1320
tacaatgaac tgcagaaaga taagatggcg gaggcctaca gtgagattgg gatgaaaggc   1380
gagcgccgga ggggcaaggg gcacgatggc ctttaccagg gtctcagtac agccaccaag   1440
gacacctacg acgcccttca catgcaggcc ctgcccctc gctaggtcga caatcaacct   1500
```

-continued

```
ctggattaca aaatttgtga agattgact ggtattctta actatgttgc tccttttacg    1560
ctatgtggat acgctgcttt aatgcctttg tatcatgcta ttgcttcccg tatggctttc    1620
attttctcct ccttgtataa atcctggttg ctgtctcttt atgaggagtt gtggcccgtt    1680
gtcaggcaac gtggcgtggt gtgcactgtg tttgctgacg caaccccac tggttggggc     1740
attgccacca cctgtcagct cctttccggg actttcgctt tcccctccc tattgccacg     1800
gcggaactca tcgccgcctg ccttgcccgc tgctggacag gggctcggct gttgggcact    1860
gacaattccg tggtgttgtc ggggaagctg acgtcctttc catggctgct cgcctgtgtt    1920
gccacctgga ttctgcgcgg gacgtccttc tgctacgtcc cttcggccct caatccagcg    1980
gaccttcctt cccgcggcct gctgccggct ctgcggcctc ttccgcgtct tcgccttcgc    2040
cctcagacga gtcggatctc cctttgggcc gcctccccgc ctggaattcg ctagcctcga    2100
gctcacacaa aaaccaaca cacagatgta atgaaaataa agatatttta ttgcggccgc     2160
tttagtttcg gaggtaacct gtaagtctgt taatgaagta aaagttcctt aggattccaa    2220
ctctgactat ggtccaggca cagtgactgt actccttggc cttcaggtaa tgcagaatcc    2280
tcccataata tcttttcagg tgcagactgc tcatgagttt tcccctggtg aaatcttctt    2340
tctccagttt ttcttccagg actgtcttca gatggtttat ctgatgatag acattagcca    2400
ggaggttctc aacaatagtc tcattccagc cagtgctaga tgaatcttgt ctgaaaatag    2460
caaagatgtt ctggagcatc tcatagatgg tcaatgcggc gtcctccttc tggaactgct    2520
gcagctgctt aatctcctca gggatgtcaa agttcatcct gtccttgagg cagtattcaa    2580
gcctcccatt caattgccac aggagcttct gacactgaaa attgctgctt ctttgtagga    2640
atccaagcaa gttgtagctc atggaaagag ctgtagtgga gaagcacaac aggagagcaa    2700
tttggaggag acacttgttg gtcatggtgg cgaccggtag cgctaggtca tatgcaggag    2760
ttgaggttac tgtgagtagt gattaaagag agtgataggg aactcttgaa caagagatgc    2820
aatttatact gttaattctg gaaaaatatt atgggggtgt caaaatgtcc cgggacaatt    2880
gacgccttct gtatgaaaca gttttcctc cacgccttct gtatgaaaca gttttcctc     2940
cacgccttct gtatgaaaca gttttcctc cgtcgaggac aattgacgcc ttctgtatga    3000
aacagttttt cctccacgcc ttctgtatga acagttttt cctccacgcc ttctgtatga    3060
aacagttttt cctcc                                                     3075
```

<210> SEQ ID NO 92
<211> LENGTH: 187
<212> TYPE: PRT
<213> ORGANISM: Homo sapiens

<400> SEQUENCE: 92

```
Met Thr Asn Lys Cys Leu Leu Gln Ile Ala Leu Leu Cys Phe Ser
1               5                  10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
```

```
                    85                  90                  95
Ser Thr Gly Trp Asn Glu Thr Ile Val Glu Asn Leu Leu Ala Asn Val
                100                 105                 110

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
        130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185

<210> SEQ ID NO 93
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 93

Gly Gly Gly Gly Ser Gly Gly Gly Ser Gly Gly Gly Gly Ser
1               5                   10                  15

<210> SEQ ID NO 94
<211> LENGTH: 194
<212> TYPE: DNA
<213> ORGANISM: Artificial Sequence
<220> FEATURE:
<223> OTHER INFORMATION: synthetic polynucleotide

<400> SEQUENCE: 94
acgccttctg tatgaaacag ttttcctcc acgccttctg tatgaaacag ttttcctcc        60 acgccttctg tatgaaacag ttttcctcc gtcgaggaca attgacgcct tctgtatgaa      120
acagtttttc ctccacgcct tctgtatgaa acagtttttc ctccacgcct tctgtatgaa    180
acagtttttc ctcc                                                      194
```

ANTIBODY FOR ANTI-CLAUDIN 18A2 AND USE THEREOF

CROSS-REFERENCE

This application is a National Stage application under 35 U.S.C. § 371 of International Application No. PCT/CN2017/092381, filed on Jul. 10, 2017, which claims the benefit of Chinese Application No. CN201610536449.9 filed on Jul. 8, 2016, and PCT International Application No. PCT/CN2017/082024 filed on Apr. 26, 2017, the entire disclosures of each of which are hereby incorporated by reference thereto.

SEQUENCE LISTING

The instant application contains a Sequence Listing which has been submitted electronically in ASCII format and is hereby incorporated by reference in its entirety. Said ASCII copy, created on Nov. 29, 2019, is named 400684-001US_165388_SL_ST25.txt and is 90,526 bytes in size.

TECHNICAL FIELD

The present invention belongs to the field of immunology, and in particular, the invention relates to antibodies against claudin 18A2 and uses thereof.

BACKGROUND

Chimeric antigen receptor (CAR) is an artificial recombinant receptor that usually contains the antigen recognition domain of a monoclonal antibody located in extracellular region, a transmembrane region and an intracellular activation signal domain of an immune response cell.

Gastric cancer is one of the cancers with the highest incidence rate worldwide. According to the statistics from WHO Cancer Control Project, there are 7 million patients who die of cancer every year in the world, and 700,000 of them die of gastric cancer. Compared with conventional gastric cancer treatment regimens, antibody-based treatment regimens have far-reaching application prospects due to high specificity and low side effects.

Claudin 18 (CLD18) is an intrinsic membrane protein located in the tight junction of the epithelium and endothelium with a molecular weight of approximately 27.9 KD. The GenBank accession number is splice variant 1 (CLD18A1, CLD18.1): NP_057453, NM016369, and splice variant 2 (CLD18A2, CLD18.2): NM_001002026, NP_001002026. FIG. 1A shows a comparison of identity between claudin 18A2 (SEQ ID NO:55) and claudin 18A1 (SEQ ID NO:57). In normal cells, CLD18A1 is selectively expressed in the epithelium of the lung and stomach, while CLD18A2 is slightly expressed in normal gastric epithelial short-lived cells. However, in tumor cells, CLD18A2 is strongly expressed in various types of cancer. For example, 75% of patients with gastric cancer have high expression of CLD18A2, 50% of patients with pancreatic cancer have high expression of CLD18A2, and 30% of patients with esophageal cancer have high expression of CLD18A2, which is also highly expressed in lung cancer. Therefore, it is of great significance for the treatment and detection of cancer to find antibodies binding CLD18A2 with higher specificity without binding to CLD18A1.

Type I interferons contain IFNα protein (a class of identical proteins encoded by 13 human genes from IFNA1 to IFNA13), IFNβ (encoded by a single human and mouse gene IFNB1), and other less studied interferons. Studies have shown that type I interferons have anticancer effects on some tumors, probably due to their immune stimulating function. However, systemic administration of type I interferons may have immunosuppressive effects (Lotrich, F E Major depression during interferon-α treatment: vulnerability and prevention. Dialogues Clin. Neurosci. 11, 417-425 (2009)) with major undesirable events, the most common of which are fatigue, anorexia, hepatotoxicity, flu-like symptoms and severe depression (Kreutzer, K., Bonnekoh, B., Franke, I., Ulrich, J. & Gollnick, H. Sarcoidosis, myasthenia gravis And anterior ischaemic optic neuropathy: severe side effects of adjuvant interferon-α therapy in malignant melanoma?. J. Dtsch. Dermatol. Ges. 2, 689-694 (in German) (2004)), and such severe side effects severely limit its application.

SUMMARY OF THE INVENTION

The present invention overcomes the aforementioned problems and has additional advantages.

According to an aspect of the present invention, the present invention provides an antibody specifically binding to claudin 18A2, characterized in that the antibody comprises a heavy chain CDR comprising an amino acid sequence selected from the group consisting of SEQ ID NOS:31, 32, 33, 37, 38, 39, 43, 44, 45, 49, 50, 51, 83, 84, 85 or a variant thereof and/or a light chain CDR comprising an amino acid sequence selected from the group consisting of SEQ ID NOS:34, 35, 36, 40, 41, 42, 46, 47, 48, 52, 53, 54 or a variant thereof.

In some embodiments, the antibody of the invention is selected from the group consisting of (a) an antibody comprising a heavy chain variable region, wherein the heavy chain variable region has CDR1 comprising an amino acid sequence of SEQ ID NO:31, SEQ ID NO:37, SEQ ID NO:43 or SEQ ID NO:49, CDR2 comprising an amino acid sequence of SEQ ID NO:32, SEQ ID NO:38, SEQ ID NO:44, SEQ ID NO:50, SEQ ID NO:83, SEQ ID NO:84 or SEQ ID NO:85, CDR3 comprising an amino acid sequence of SEQ ID NO:33, SEQ ID NO:39, SEQ ID NO:45 or SEQ ID NO:51; (b) an antibody comprising a light chain variable region, wherein the light chain variable region has CDR1 comprising an amino acid sequence of SEQ ID NO:34, SEQ ID NO:40, SEQ ID NO:46 or SEQ ID NO:52, CDR2 comprising an amino acid sequence of SEQ ID NO:35, SEQ ID NO:41, SEQ ID NO:47 or SEQ ID NO:53, CDR3 comprising an amino acid sequence of SEQ ID NO:36, SEQ ID NO:42, SEQ ID NO:48 or SEQ ID NO:54; (c) an antibody comprising (a) a heavy chain variable region of said antibody and (b) a light chain variable region of said antibody; (d) an antibody, recognizing the same antigenic determinant site as that of the antibody of any one of (a) to (c).

In some embodiments, the CDR1, CDR2 and CDR3 regions of the heavy chain variable region of the antibody are SEQ ID NO:31, SEQ ID NO:32, SEQ ID NO:33; or SEQ ID NO:37, SEQ ID NO:38, SEQ ID NO:39; or SEQ ID NO:43, SEQ ID NO:44, SEQ ID NO:45; or SEQ ID NO:49, SEQ ID NO:50, SEQ ID NO:51; or SEQ ID NO:31, SEQ ID NO:83, SEQ ID NO:33; or SEQ ID NO:31, SEQ ID NO:84, SEQ ID NO:33; or SEQ ID NO:49, SEQ ID NO 85, SEQ ID NO:51, respectively; and/or the CDR1, CDR2 and CDR3 regions of the light chain variable region of the antibody are SEQ ID NO:34, SEQ ID NO:35, SEQ ID NO:36; or SEQ ID NO:40, SEQ ID NO:41, SEQ ID NO:42; or SEQ ID NO:46, SEQ ID NO:47, SEQ ID NO:48; or SEQ ID NO:52, SEQ ID NO:53, SEQ ID NO:54, respectively.

In some embodiments, the antibody comprises a heavy chain variable region and a light chain variable region, wherein the heavy chain variable region has an amino acid sequence of SEQ ID NO:3, SEQ ID NO:7, SEQ ID NO:11, SEQ ID NO:15, SEQ ID NO:17, SEQ ID NO:19, SEQ ID NO:23, SEQ ID NO:27 or SEQ ID NO:29; and the light chain variable region has an amino acid sequence of SEQ ID NO:1, SEQ ID NO:5, SEQ ID NO:9, SEQ ID NO:13, SEQ ID NO:21 or SEQ ID NO:25. In some embodiments, the antibody is an antibody having a heavy chain variable region of SEQ ID NO:3 and a light chain variable region of SEQ ID NO:1; an antibody having a heavy chain variable region of SEQ ID NO:7 and a light chain variable region of SEQ ID NO:5; an antibody having a heavy chain variable region of SEQ ID NO:11 and a light chain variable region of SEQ ID NO:9; an antibody having a heavy chain variable region of SEQ ID NO:15 and a light chain variable region of SEQ ID NO:13; an antibody having a heavy chain variable region of SEQ ID NO:17 and a light chain variable region of SEQ ID NO:1; an antibody having a heavy chain variable region of SEQ ID NO:19 and a light chain variable region of SEQ ID NO:1; an antibody having a heavy chain variable region of SEQ ID NO:23 and a light chain variable region of SEQ ID NO:21; an antibody having a heavy chain variable region of SEQ ID NO:27 and a light chain variable region of SEQ ID NO:25; or an antibody having a heavy chain variable region of SEQ ID NO:29 and a light chain variable region of SEQ ID NO:25. In some embodiments, the antibody is an antibody having a heavy chain variable region of SEQ ID NO:3 and a light chain variable region of SEQ ID NO:1; an antibody having a heavy chain variable region of SEQ ID NO:17 and a light chain variable region of SEQ ID NO:1; an antibody having a heavy chain variable region of SEQ ID NO:19 and a light chain variable region of SEQ ID NO:1; an antibody having a heavy chain variable region of SEQ ID NO:23 and a light chain variable region of SEQ ID NO:21; an antibody having a heavy chain variable region of SEQ ID NO:27 and a light chain variable region of SEQ ID NO:25; or an antibody having a heavy chain variable region of SEQ ID NO:29 and a light chain variable region of SEQ ID NO:25. In some embodiments, the antibody is a humanized antibody, a chimeric antibody or a fully humanized antibody; or the antibody is a monoclonal antibody; or the antibody is a single chain antibody or a domain antibody. In some embodiments, the antibody is a humanized antibody selected from the group consisting of an antibody having a heavy chain variable region of SEQ ID NO:27 and a light chain variable region of SEQ ID NO:25; an antibody having a heavy chain variable region of SEQ ID NO:23 and a light chain variable region of SEQ ID NO:21; an antibody having a heavy chain variable region of SEQ ID NO:29 and a light chain variable region of SEQ ID NO:25. In some embodiments, the antibody is selected from the group consisting of an antibody having a heavy chain of SEQ ID NO:63 and a light chain of SEQ ID NO:65; an antibody having a light chain of SEQ ID NO:61 and a heavy chain of SEQ ID NO:59; and an antibody having a heavy chain of SEQ ID NO:67 and a light chain of SEQ ID NO:65.

According to one aspect of the invention, the invention provides a nucleic acid encoding the antibody as mentioned above. According to another aspect of the invention, the invention provides an expression vector comprising the nucleic acid. According to another aspect of the present invention, the present invention provides a host cell comprising the expression vector of the present invention or having the nucleic acid of the present invention integrated into its genome.

According to one aspect of the invention, the invention provides the use of an antibody according to the invention for preparing a targeting drug, antibody-drug conjugate or multifunctional antibody specifically targeting tumor cells expressing claudin 18A2; or for preparing a reagent for diagnosing a tumor expressing claudin 18A2; or for preparing a chimeric antigen receptor modified immune cell. In some embodiments, the tumor expressing claudin 18A2 includes: gastric cancer, pancreatic cancer, esophageal cancer, lung cancer.

According to one aspect of the invention, the invention provides a chimeric antigen receptor comprising an antibody of the invention, wherein the chimeric antigen receptor comprises following sequentially linked components: an antibody of the invention, a transmembrane region and an intracellular signal region. In some embodiments, the intracellular signal region is selected from the group consisting of: an intracellular signal region sequence of CD3ζ, FcεRIγ, CD27, CD28, CD137, CD134, MyD88, CD40, or a combination thereof; or the transmembrane region comprises a transmembrane region of CD8 or CD28. In some embodiments, the chimeric antigen receptor comprises sequentially linked an antibody, a transmembrane region and an intracellular signaling region: an antibody of the invention, CD8 and CD3ζ; an antibody of the invention, CD8, CD137 and CD3ζ; or an antibody of the invention, a transmembrane region of CD28 molecule, an intracellular signal region of CD28 molecule, and CD3ζ; or an antibody of the invention, a transmembrane region of CD28 molecule, an intracellular signal region of CD28 molecule, CD137 and CD3ζ.

According to another aspect of the invention, the invention provides a nucleic acid encoding the chimeric antigen receptor. According to another aspect of the invention, the invention provides an expression vector comprising the nucleic acid of the invention. According to another aspect of the invention, the invention provides a virus comprising the vector of the invention.

According to an aspect of the present invention, the present invention provides uses of a chimeric antigen receptor, nucleic acid, expression vector or virus of the present invention for preparing chimeric antigen receptor-modified immune cells targeting tumor cells expressing claudin 18A2. In some embodiments, the tumor expressing claudin 18A2 includes: gastric cancer, pancreatic cancer, esophageal cancer, lung cancer.

According to one aspect of the present invention, the present invention provides a chimeric antigen receptor-modified immune cell transduced with a nucleic acid, expression vector or virus of the present invention; or having a chimeric antigen receptor of the present invention expressed on the surface. In some embodiments, the immune cell is: a T lymphocyte, NK cell or NKT lymphocyte. In some embodiments, the immune cell further carries an encoding sequence for an exogenous cytokine; or further expresses another chimeric antigen receptor which does not contain CD3ζ but contains an intracellular signal domain of CD28, an intracellular signal domain of CD137, or a combination of the both; or further expresses a chemokine receptor (preferably, said chemokine receptor comprises: CCR); or further expresses an siRNA which can reduce expression of PD-1 or a protein which can block PD-L1; or endogenous PD-1 in the immune cell is knocked out by gene editing techniques; or further expresses a safety switch.

According to one aspect of the present invention, the present invention provides uses of the chimeric antigen receptor-modified immune cell for producing a tumor-inhibiting drug, wherein the tumor is a tumor expressing claudin 18A2; preferably, the tumor includes: gastric cancer, pancreatic cancer, esophageal cancer, and lung cancer.

According to one aspect of the present invention, the present invention provides a multifunctional immunoconjugate comprising an antibody of the present invention; and a functional molecule linked thereto; and the functional molecule is selected from the group consisting of: a molecule targeting a surface marker on a tumor, a tumor-inhibiting molecule, a molecule targeting a surface marker of an immune cell or a detectable label. In some embodiments, the molecule targeting a surface marker of an immune cell is an antibody binding to a T cell surface marker, which forms a bifunctional antibody with the antibody of the invention in which T cell is involved. According to another aspect of the invention, the invention provides a nucleic acid encoding said multifunctional immunoconjugate and uses thereof for preparing anti-tumor drugs. In some embodiments, the nucleic acid encoding the multifunctional immunoconjugate is used to prepare a reagent for diagnosing a tumor expressing claudin 18A2. In some embodiments, the nucleic acid encoding the multifunctional immunoconjugate is used to prepare chimeric antigen receptor modified immune cells. In some embodiments, the immune cells includes: a T lymphocyte, NK cell or NKT lymphocyte.

According to one aspect of the invention, the invention provides a pharmaceutical composition comprising an antibody of the invention or a nucleic acid encoding the antibody. According to one aspect of the invention, the invention provides a pharmaceutical composition comprising an immunoconjugate of the invention or a nucleic acid encoding the conjugate. According to one aspect of the invention, the invention provides a pharmaceutical composition comprising a chimeric antigen receptor of the invention or a nucleic acid encoding the chimeric antigen receptor. According to one aspect of the invention, the invention provides a pharmaceutical composition comprising a chimeric antigen receptor modified immune cell of the invention. In some embodiments, the pharmaceutical composition comprises a pharmaceutically acceptable carrier or excipient.

According to an aspect of the invention, a kit is provided in the invention comprising a container, and a pharmaceutical composition of the invention in the container; or a container, and an antibody of the invention or a nucleic acid encoding the antibody in the container; or the immunoconjugate of the present invention or a nucleic acid encoding the conjugate; or the chimeric antigen receptor of the present invention or a nucleic acid encoding the chimeric antigen receptor; or the chimeric antigen receptor modified immune cell of the invention.

According to one aspect of the present invention, the present invention provides an antigen binding unit comprising a light chain CDR and a heavy chain CDR, wherein the antigen binding unit specifically binds to a claudin 18A2 peptide; and the antigen binding unit does not significantly bind to a claudin 18A1 peptide. According to another aspect of the present invention, the present invention provides an antigen binding unit comprising a light chain CDR and a heavy chain CDR, wherein the antigen binding unit specifically binds to a claudin 18A2 peptide; and the antigen binding unit, compared with a reference antigen binding unit, exhibits less non-specific binding to the claudin 18A1 peptide. In some embodiments, the reference antigen binding unit comprises a light chain amino acid sequence of SEQ ID NO:86 or SEQ ID NO:88 and/or a heavy chain amino acid sequence of SEQ ID NO:87 or SEQ ID NO:89. In some embodiments, the claudin 18A2 peptide comprises an amino acid sequence of SEQ ID NO:55. In some embodiments, the claudin 18A1 peptide comprises an amino acid sequence of SEQ ID NO:57. In some embodiments, the non-specific binding of the antigen binding unit to the claudin 18A1 peptide does not exceed 20% of the specific binding to the claudin 18A2 peptide. In some embodiments, the binding specificity is determined by flow cytometry. In some embodiments, the binding specificity is determined by FACS. In some embodiments, the binding specificity is determined by ELISA. In some embodiments, the antigen binding unit binds to the claudin 18A2 peptide with an EC50 of less than about 100 nM. In some embodiments, the antigen binding unit is a monoclonal antibody, a humanized antibody, a chimeric antibody, a multivalent antibody or a chimeric antigen receptor. In some embodiments, the light chain CDR comprises LCDR1, LCDR2 and LCDR3; and the heavy chain CDR comprises HCDR1, HCDR2 and HCDR3; wherein the LCDR1, LCDR2 and LCDR3 respectively have an amino acid sequence selected from the group consisting of: SEQ ID NO:34, SEQ ID NO:35, SEQ ID NO:36, SEQ ID NO:40, SEQ ID NO:41, SEQ ID NO:42, SEQ ID NO:46, SEQ ID NO:47, SEQ ID NO:48, SEQ ID NO:52, SEQ ID NO:53 and SEQ ID NO:54; and the HCDR1, HCDR2 and HCDR3 respectively have an amino acid sequence selected from the group consisting of SEQ ID NO:31, SEQ ID NO:32, SEQ ID NO:33, SEQ ID NO:37, SEQ ID NO:38, SEQ ID NO:39, SEQ ID NO:43, SEQ ID NO:44, SEQ ID NO:45, SEQ ID NO:49, SEQ ID NO:50, SEQ ID NO:51, SEQ ID NO:83, SEQ ID NO:84 and SEQ ID NO:85. In some embodiments, the LCDR1 comprises an amino acid sequence selected from the group consisting of SEQ ID NO:34, SEQ ID NO:40, SEQ ID NO:46 and SEQ ID NO:52. In some embodiments, the LCDR2 comprises an amino acid sequence selected from the group consisting of SEQ ID NO:34, SEQ ID NO:41, SEQ ID NO:47 and SEQ ID NO:53. In some embodiments, the LCDR3 comprises an amino acid sequence selected from the group consisting of SEQ ID NO:35, SEQ ID NO:42, SEQ ID NO:48 and SEQ ID NO:54. In some embodiments, the HCDR1 comprises an amino acid sequence selected from the group consisting of SEQ ID NO:31, SEQ ID NO:37, SEQ ID NO:43 and SEQ ID NO:49. In some embodiments, the HCDR2 comprises an amino acid sequence selected from the group consisting of SEQ ID NO:32, SEQ ID NO:38, SEQ ID NO:44, SEQ ID NO:50, SEQ ID NO:83, SEQ ID NO:84 and SEQ ID NO:85. In some embodiments, the HCDR3 comprises an amino acid sequence selected from the group consisting of SEQ ID NO:33, SEQ ID NO:39, SEQ ID NO:45 and SEQ ID NO:51. In some embodiments, the antigen binding unit is scFv, Fv, Fab or (Fab)2.

According to one aspect of the invention, the invention provides an antigen binding unit comprising a light chain CDR and a heavy chain CDR, wherein said light chain CDR comprises LCDR1, LCDR2 and LCDR3; said heavy chain CDR comprises HCDR1, HCDR2 and HCDR3; the LCDR1, LCDR2 and LCDR3 respectively comprise an amino acid sequence which is at least 80% identical to an amino acid sequence selected from the group consisting of SEQ ID NO:34, SEQ ID NO:35, SEQ ID NO:36, SEQ ID NO:40, SEQ ID NO:41, SEQ ID NO:42, SEQ ID NO:46, SEQ ID NO:47, SEQ ID NO:48, SEQ ID NO:52, SEQ ID NO:53 and SEQ ID NO:54; and the HCDR1, HCDR2 and HCDR3 respectively comprise an amino acid sequence which is at least 80% identical to an amino acid sequence selected from the group consisting of SEQ ID NO:31, SEQ ID NO:32, SEQ ID NO:33, SEQ ID NO:37, SEQ ID NO:38, SEQ ID NO:39, SEQ ID NO:43, SEQ ID NO:44, SEQ ID NO:45, SEQ ID NO:49, SEQ ID NO:50, SEQ ID NO:51, SEQ ID NO:83, SEQ ID NO:84 and SEQ ID NO:85. In some embodiments, the light chain CDR comprises LCDR1, LCDR2 and LCDR3; the heavy chain CDR comprises HCDR1, HCDR2 and HCDR3; the LCDR1, LCDR2 and LCDR3 respectively have an amino acid sequence selected from the group consisting of: SEQ ID NO:34, SEQ ID NO:35, SEQ ID NO:36, SEQ ID NO:40, SEQ ID NO:41, SEQ ID NO:42, SEQ ID NO:46, SEQ ID NO:47, SEQ ID NO:48 SEQ ID NO:52, SEQ ID NO:53 and SEQ ID NO:54; and the HCDR1, HCDR2 and HCDR3 respectively have an amino acid sequence selected from the group consisting of SEQ ID NO:31, SEQ ID NO:32, SEQ ID NO:33, SEQ ID NO:37, SEQ ID NO:38, SEQ ID NONO:39, SEQ ID NO:43, SEQ ID NO:44, SEQ ID NO:45, SEQ ID NO:49, SEQ ID NO:50, SEQ ID NO:51, SEQ ID NO:83, SEQ ID NO:84 and SEQ ID NO:85. In some embodiments, the LCDR1 comprises an amino acid sequence which is at least 80% identical to an amino acid sequence selected from the group consisting of: SEQ ID NO:34, SEQ ID NO:40, SEQ ID NO:46 and SEQ ID NO:52. In some embodiments, the LCDR2 comprises an amino acid sequence which is at least 80% identical to an amino acid sequence selected from the group consisting of SEQ ID NO:34, SEQ ID NO:41, SEQ ID NO:47 and SEQ ID NO:53. In some embodiments, the LCDR3 comprises an amino acid sequence which is at least 80% identical to an amino acid sequence selected from the group consisting of SEQ ID NO:35, SEQ ID NO:42, SEQ ID NO:48 and SEQ ID NO:54. In some embodiments, the HCDR1 comprises an amino acid sequence which is at least 80% identical to an amino acid sequence selected from the group consisting of SEQ ID NO:31, SEQ ID NO:37, SEQ ID NO:43 and SEQ ID NO:49. In some embodiments, the HCDR2 comprises an amino acid sequence which is at least 80% identical to an amino acid sequence selected from the group consisting of: SEQ ID NO:32, SEQ ID NO:38, SEQ ID NO:44, SEQ ID NO:50 SEQ ID NO:83, SEQ ID NO:84 and SEQ ID NO:85. In some embodiments, the HCDR3 comprises an amino acid sequence which is at least 80% identical to an amino acid sequence selected from the group consisting of SEQ ID NO:33, SEQ ID NO:39, SEQ ID NO:45 and SEQ ID NO:51. In some embodiments, the antigen binding unit is a monoclonal antibody, a humanized antibody, a chimeric antibody, a multivalent antibody or a chimeric antigen receptor. In some embodiments, the antigen binding unit is scFv, Fv, Fab or (Fab)2.

According to one aspect of the invention, the invention provides a chimeric antigen receptor comprising an extracellular antigen binding unit, a transmembrane domain and an intracellular domain, wherein the extracellular antigen binding unit comprises an antigen binding unit of the invention. According to one aspect of the invention, the invention provides a composition comprising an antigen binding unit or a chimeric antigen receptor of the invention. In some embodiments, the composition comprises a Type I interferon. According to one aspect of the invention, the invention provides an isolated nucleic acid encoding an antigen binding unit or chimeric antigen receptor of the invention, and optionally a type I interferon. According to one aspect of the invention, the invention provides a vector comprising a nucleic acid of the invention.

According to one aspect of the invention, the invention provides a host cell which expresses an antigen binding unit or chimeric antigen receptor of the invention, and optionally a type I interferon. According to one aspect of the invention, the invention provides a host cell comprising a nucleic acid encoding the antigen binding unit or chimeric antigen receptor of the invention, and optionally a type I interferon. In some embodiments, the host cell is an immune response cell. In some embodiments, the host cell is a T cell, natural killer cell, cytotoxic T lymphocyte, natural killer T cell, DNT cell, and/or regulatory T cell. In some embodiments, the host cell is an NK92 cell.

In some embodiments, the host cell is cytotoxic to a cell comprising a claudin 18A2 peptide comprising the amino acid sequence of SEQ ID NO:55. In some embodiments, the host cell does not have significant cytotoxicity to a cell comprising a claudin 18A1 peptide while not comprising a claudin 18A2 peptide, and the claudin 18A1 peptide comprises an amino acid sequence of SEQ ID NO:57, and the claudin 18A2 peptide comprises the amino acid sequence of SEQ ID NO:55.

According to one aspect of the invention, the invention provides a method for producing an antigen binding unit or chimeric antigen receptor or composition of the invention, including: culturing a host cell of the invention under suitable conditions, and obtaining the product expressed by the host cell.

According to one aspect of the invention, the invention provides a method for inducing the death of a cell comprising a claudin 18A2 peptide, including contacting the cell with an antigen binding unit, chimeric antigen receptor, composition or host cell of the invention. In some embodiments, the cell is contacted with the antigen binding unit, the chimeric antigen receptor, the composition or host cell in vitro. In some embodiments, the cell is contacted with the antigen binding unit, the chimeric antigen receptor, the composition or host cell in vivo. In some embodiments, the cell is a cancer cell. In some embodiments, the cell is a solid tumor cell. In some embodiments, the cell is selected from the group consisting of: a gastric cancer cell, esophageal cancer cell, intestinal cancer cell, pancreatic cancer cell, nephroblastoma cell, lung cancer cell, ovarian cancer cell, colon cancer cell, rectal cancer cell, liver cancer cell, head and neck cancer cell, chronic myeloid leukemia cell and gallbladder cancer cell.

According to one aspect of the invention, the invention provides a method for treating a tumor in an individual in need thereof, the method including administering to the individual an effective amount of an antigen binding unit, chimeric antigen receptor, composition or host cell of the invention. In some embodiments, the tumor is a solid tumor. In some embodiments, the tumor is gastric cancer, esophageal cancer, intestinal cancer, pancreatic cancer, nephroblastoma, lung cancer, ovarian cancer, colon cancer, rectal cancer, liver cancer, head and neck cancer, chronic myelogenous leukemia or gallbladder cancer. In some embodiments, the method further includes administering to the individual an additional therapeutic agent. In some embodiments, the additional therapeutic agent is at least one selected from the group consisting of epirubicin, oxaliplatin and 5-fluorouracil.

INCORPORATION BY REFERENCE

All publications, patents and patent applications mentioned in this specification are herein incorporated by reference as if each of the publications, patents or patent applications is incorporated by reference.

BRIEF DESCRIPTION OF DRAWINGS

Drawings further illustrate novel features disclosed in this specification. Features and advantages of the present disclosure will be better understood from the following description of the accompanying drawings. It is to be understood, however, that the drawings are only intended to illustrate the specific embodiments of the application of principles disclosed herein, and are not intended to limit the scope of the appended claims.

FIG. 1A shows the identity comparison between claudin 18A2 (SEQ ID NO:55) and claudin 18A1 (SEQ ID NO:57)

FIG. 2 shows sequence alignment of murine anti-2B1 (heavy chain variable region SEQ ID NO:3, light chain variable region SEQ ID NO:1), 3E12 (heavy chain variable region SEQ ID NO:7, light chain variable region SEQ ID NO:5), 4A11 (heavy chain variable region SEQ ID NO:11, light chain variable region SEQ ID NO:9), 8E5 (heavy chain variable region SEQ ID NO:15, light chain variable region SEQ ID NO:13).

FIG. 3 shows the relative binding affinity of murine anti-2B1, 8E5 ScFv, after fused to human IgG1 Fc portion, to HEK293 cells stably transfected with human CLD18A2.

FIG. 4 shows the relative binding affinity of engineered murine anti-2B1 antibody 2B1-N52D and 2B1-S54A, after fused to human IgG1 Fc portion, to HEK293 cells stably transfected with human CLD18A2.

FIG. 8A compares CDC effects of the humanized antibodies hu2B1-S54A, hu8E5-2I and the known chimeric antibody ch-163E12 (see CN103509110A) on HEK293 cells transfected with CLD18A2; and FIG. 8B compares CDC results of the humanized antibodies hu2B1-S54A, hu8E5-2I and ch-163E12 on HEK293 cells transfected with CLD18A1.

FIG. 17A shows the secretion of cellular molecules after co-expression of IFN; FIG. 17B is a comparison graph of anti-tumor activities of CAR-T cells containing IFN and IFN-free in subcutaneous xenografts of gastric cancer PDX model; and FIG. 17C is a comparison graph of the number of viable cells in the peripheral blood of a mouse at the 5, 7 and 10 days of returning CAR-T cells.

FIG. 18A and FIG. 18B are plasmid maps for the construction of CAR-NK cells.

FIG. 19 shows the determination of the positive rate of hu8E5-2I-28Z CAR-NK92 and hu8E5-28BBZ CAR-NK92.

MODE FOR CARRYING OUT THE INVENTION

Figure 1B:
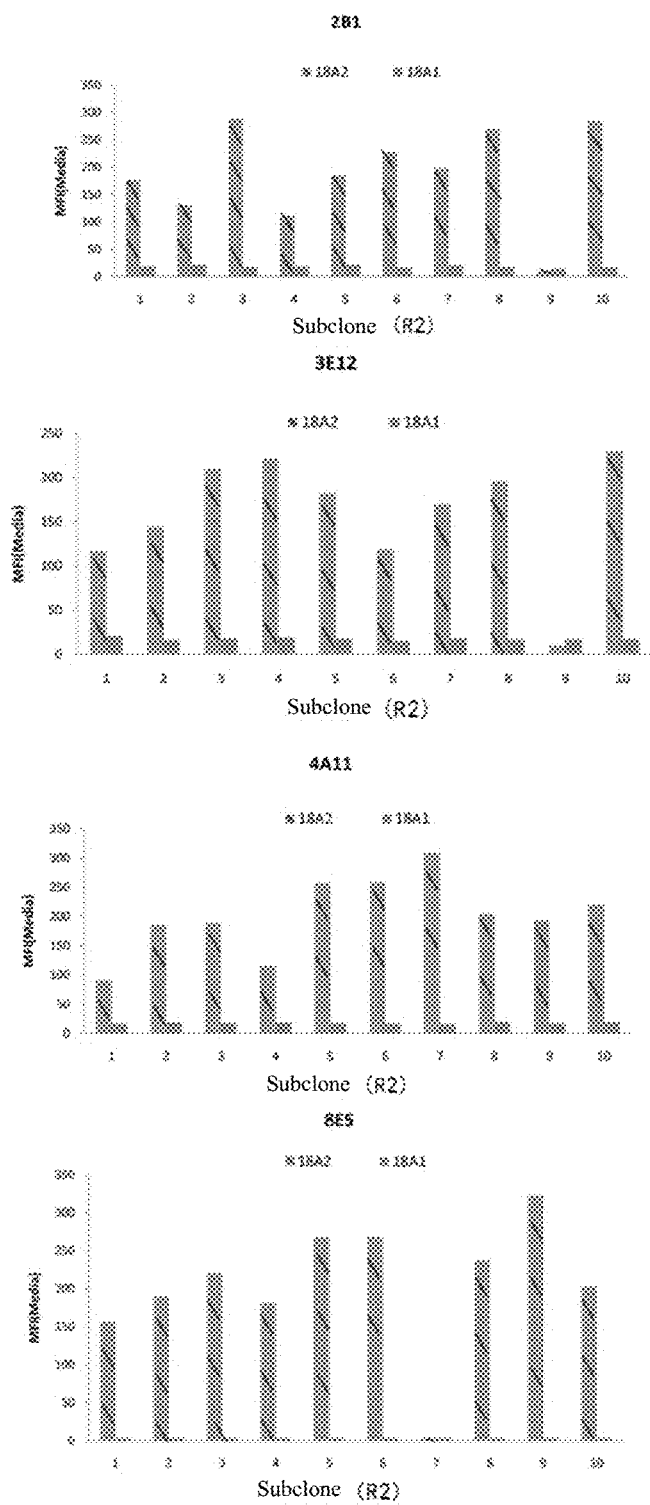
FIG. 1B shows binding of hybridoma supernatants 2B1, 3E12, 4A11 and 8E5 to HEK293 cells stably transfected with human CLD18A2 and CLD18A1 as determined by flow cytometry.

The detailed description below discloses the embodiments disclosed herein in detail. It should be understood that the description is not intended to be limited to the particular embodiments disclosed herein, which can be varied. It will be understood by a skilled person that the present disclosure may be variously modified or varied, and all of the modifications fall within the scope and spirit of the disclosure. Each embodiment can be combined arbitrarily with any other embodiment unless otherwise stated.

Certain embodiments disclosed herein are intended to encompass a range of values, and certain aspects of the invention may be described by using a range. Unless otherwise stated, it should be understood that a range of values or the description of a scope is for the purpose of simplicity and convenience, and the scope of the invention is not to be understood as being strictly limited by the scope of the invention. Therefore, the description of a scope should be construed as being specifically described as all possible sub-ranges and all possible specific numerical points within the range, as these sub-ranges and numerical points are explicitly recited herein. For example, the description of the range from 1 to 6 should be considered to specifically disclose sub-ranges from 1 to 3, 1 to 4, 1 to 5, 2 to 4, 2 to 6, 3 to 6, etc., and specific numerical points within these ranges, such as 1, 2, 3, 4, 5 and 6. Regardless of the breadth of stated values, the above principles are equally applicable. When a range is described, the range includes endpoints of the range.

When referring to measurable values, such as amount, temporary duration, etc., the term "about" is meant to include a change of ±20%, or in some cases ±10%, or in some cases ±5%, or in some cases ±1%, or in some cases ±0.1% of the specified value.

As used herein, the terms "activate" and "activation" can be used interchangeably and they, as well as other grammatical forms thereof, may refer to a process via which a cell transits from a quiescent state to an active state. The process can include a response to an antigen, migration and/or a phenotypic or genetic change in the functionally active state. For example, the term "activation" can refer to a process via which immune cells are gradually activated. For example, T cells may require at least two signals to be fully activated. The first signal can occur after the TCR is bound by the antigen-MHC complex, while the second signal can occur by the conjugation of costimulatory molecules (see costimulatory molecules listed in Table 1). Anti-CD3 can in vitro simulate the first signal and anti-CD28 can simulate the second signal. For example, engineered T cells can be activated by the expressed CAR. As used herein, immune cell activation may refer to a state that has been sufficiently stimulated to induce detectable cell proliferation, cytokine production and/or detectable effector function.

The term "co-stimulatory molecule" as used herein refers to a homologous binding partner on an immune cell, such as a T cell, that specifically binds to a costimulatory ligand, thereby mediating a costimulatory response such as, but not limited to, proliferation. A costimulatory molecule is a molecule on cell surface other than an antigen receptor or its ligand that promotes an effective immune response. Costimulatory molecules include, but are not limited to, MHC class I molecules, BTLA and Toll ligand receptors, and OX40, CD27, CD28, CDS, ICAM-1, LFA-1 (CD11a/CD18), ICOS (CD278) and 4-1BB (CD137). Examples of costimulatory molecules include, but are not limited to, CDS, ICAM-1, GITR, BAFFR, HVEM (LIGHTR), SLAMF7, NKp80 (KLRF1), NKp44, NKp30, NKp46, CD160, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a and a ligand that specifically binds to CD83.

As used herein, "costimulatory signal" refers to a signal that, in combination with a first signal, such as TCR/CD3, results in T cell proliferation and/or up- or down-regulation of key molecules.

The term "antigen binding unit" as used herein refers to an immunoglobulin molecule and an immunologically active portion of an immune molecule, i.e., a molecule containing an antigen binding site that specifically binds to an antigen ("immune response"). The term "antigen-binding unit" also includes immunoglobulin molecules of various species, including invertebrates and vertebrates. The simplest naturally occurring antibody (e.g., IgG) structurally comprises four polypeptide chains, two heavy (H) chains and two light (L) chains interconnected by disulfide bonds. Immunoglobulins represent a large family of molecules including several types of molecules, such as IgD, IgG, IgA, IgM and IgE. The term "immunoglobulin molecule" includes, for example, a hybrid antibody or altered antibody and fragments thereof. It has been shown that the antigen binding function of an antibody can be carried out by fragments of a naturally occurring antibody. Such fragments are collectively named as "antigen combining unit". The term "antigen-binding unit" also includes any polypeptide chain-containing molecular structure having a specific shape that conforms to an epitope and recognizes an epitope, wherein one or more non-covalent binding interactions stabilize the complex between the molecular structure and the epitope. Examples of such antigen binding units include a Fab fragment, monovalent fragment consisting of VL, VH, CL and CH1 domains, bivalent fragment comprising two Fab fragments joined by a disulfide bridge on the hinge region (F(ab)2 fragment); Fd fragment consisting of VH and CH1 domains, Fv fragment consisting of VL and VH domains of a single arm of an antibody; dAb fragment consisting of VH domain (Ward et al., Nature, 341: 544-546, 1989); and isolated complementarity determining regions (CDRs) or any fusion protein comprising such antigen binding units.

The term "antibody" as used herein includes an intact antibody and any antigen-binding fragments (i.e., "antigen-binding portions") or single chains thereof. A naturally occurring "antibody" is a glycoprotein comprising at least two heavy (H) chains and two light (L) chains joined by a disulfide bond. Each heavy chain consists of a heavy chain variable region (abbreviated herein as VH) and a heavy chain constant region. The heavy chain constant region consists of three domains, CH1, CH2 and CH3. Each light chain consists of a light chain variable region (abbreviated herein as VL) and a light chain constant region. The light chain constant region consists of one domain CL. VH and VL regions can be further subdivided into regions of high variability named as complementarity determining regions (CDRs) that are spaced by more conserved regions named as framework region (ER). Each VH and V L consists of three CDRs and four FRs arranged in the following order from the amino terminus to the carboxy terminus: FR1, CDR1, FR2, CDR2, FR3, CDR3, FR4. The variable regions of the heavy chain and light chain contain a binding domain that interacts with the antigen. The constant region of an antibody can mediate the binding of the immunoglobulin to host tissues or factors, including various cells of the immune system (e.g., effector cells) and the first component (C1q) of the classical complement system.

The term "scFv" refers to a fusion protein comprising at least one antibody fragment comprising a variable region of a light chain and at least one antibody fragment comprising a variable region of a heavy chain, wherein said light chain and heavy chain variable regions are contiguous (for example, via a synthetic linker, such as a short flexible polypeptide linker), and can be expressed as a single-chain polypeptide, and wherein the scFv retains the specificity of the intact antibody from which it is derived. Unless specified, as used herein, an scFv can have the VL and VH variable regions in any order (e.g., relative to N-terminus and C-terminus of the polypeptide), and the scFv can include a VL-linker-VH or A VH-linker-VL can be included.

As used herein, the terms "complementarity determining region" and "CDR" refer to an amino acid sequence in the variable region of the antibody that confers antigen specificity and binding affinity. In general, there are three CDRs (HCDR1, HCDR2, HCDR3) in each heavy chain variable region and three CDRs (LCDR1, LCDR2, LCDR3) in the light chain variable region.

An antigen binding unit "specifically binds" to an antigen or is "immunoreactive" with the antigen, if the antigen binding unit binds to the antigen with greater affinity than binding to other reference antigens, including polypeptides or other substances.

The term "humanized" as used herein is used for a non-human (such as a rodent or primate) antibody, is a hybrid immunoglobulin, immunoglobulin chain or a fragment thereof comprising a minimal sequence derived from a non-human immunoglobulin. In most cases, the humanized antibody is a human immunoglobulin (receptor antibody), in which residues from the complementarity determining regions (CDRs) of the receptor are replaced by residues from CDRs of non-human species (donor antibody), such as mice, rats, rabbits or primates having desired specificities, affinities and performances. In some cases, residues in Fv framework region (FR) of human immunoglobulin are replaced by corresponding non-human residues. Furthermore, a humanized antibody may comprise residues that are present in the recipient antibody while not in the introduced CDR or framework sequences. These modifications are made to further improve and optimize antibody performance and minimize immunogenicity when introduced into a human body. In some examples, a humanized antibody will comprise substantially all, at least one, typically two variable domains, wherein all or substantially all of the CDR regions correspond to those of a non-human immunoglobulin, and all or substantially all of FR regions are regions of a human immunoglobulin sequence. A humanized antibody can also comprise at least a portion of an immunoglobulin constant region (Fc), typically a constant region of a human immunoglobulin. In some embodiments, a "humanized antibody" can include a mutation, such as a mutation introduced by random or site-directed mutagenesis in vitro or by somatic mutation in vivo.

The term "immunoglobulin" or "Ig" as used herein may refer to a class of proteins that can function as antibodies. Antibodies expressed by B cells are sometimes named as chimeric antigen receptors or antigen receptors. Five members included in this class are IgA, IgG, IgM, IgD and IgE, with IgG being the most common circulating antibody. It is the most potent immunoglobulin in agglutination, complement fixation and other antibody reactions and is important in protection against bacteria and viruses. For example, tumor cell antigens (or "tumor antigens") or pathogen antigens can be recognized by CAR.

As used herein, the term "isolated" refers to separation from cellular components or other components in which polynucleotides, peptides, polypeptides, proteins, antibodies or fragments thereof are generally associated in a natural state. As will be understood by a skilled person, it is not necessary to 'isolate' non-naturally occurring polynucleotides, peptides, polypeptides, proteins, antibodies or fragments thereof so as to distinguish them from naturally occurring counterparts. Furthermore, a "concentrated", "isolated" or "diluted" polynucleotide, peptide, polypeptide, protein, antibody or a fragment thereof may be distinguished from its naturally occurring counterpart, since the concentration or amount of a molecule per volume is greater ("concentrated") or less ("diluted") than the concentration of its naturally occurring counterpart. The degree of enrichment can be measured on an absolute basis, such as the weight per solution volume, or can be measured relative to another potential interferent present in the source mixture. In some embodiments, higher extent of enrichment is preferable to the technical solutions of the present invention. Therefore, for example, 2-fold enrichment is preferable, 10-fold enrichment is more preferable, 100-fold enrichment is more preferable, 1000-fold enrichment is even more preferable. "Separated" materials can also be provided by artificial assembly methods, such as chemical synthesis or recombinant expression.

As used herein, "antigen" refers to a substance that is recognized and specifically bound by an antigen binding unit. Antigens can include peptides, proteins, glycoproteins, polysaccharides, lipids, portions thereof, and combinations thereof. Non-limiting exemplary antigens include tumor antigens or pathogen antigens. "Antigen" can also refer to a molecule eliciting an immune response. This immune response may involve the production of antibodies or the activation of specific immunologically-competent cells, or both. A skilled person will appreciate that any macromolecule, including virtually all proteins or peptides, can serve as an antigen.

The terms "polypeptide", "peptide" and "protein" are used interchangeably herein to refer to a polymer of amino acids of any length. The polymer may be linear, cyclic or branched, it may comprise modified amino acids, particularly conservatively modified amino acids, and it may be interrupted by non-amino acids. The term also includes modified amino acid polymers such as an amino acid polymer modified through sulfation, glycosylation, lipidation, acetylation, phosphorylation, iodination, methylation, oxidation, proteolytic processing, prenylation, racemization, selenoylation, transfer-RNA-mediated amino addition (such as argination, ubiquitination) or any other manipulation such as conjugation with a labeled component. As used herein, the term "amino acid" refers to natural and/or non-natural or synthetic amino acids, including glycine and D or L optical isomers, as well as amino acid analogs and peptidomimetics. A polypeptide or amino acid sequence "derived from" a specified protein refers to the source of the polypeptide. The term also encompasses polypeptides expressed by a specified nucleic acid sequence.

The term "amino acid modification" (or "modified amino acid") includes amino acid substitutions, insertions and/or deletions in a polypeptide sequence. As used herein, "amino acid substitution" or "substitution" means the replacement of an amino acid at a particular position in a parent polypeptide sequence with another amino acid. For example, substitution R94K means that the arginine at position 94 is replaced by lysine. For the same substitution at the same position in the parent polypeptide sequence, it can also be represented by 94K, i.e., replacing the 94 position with lysine. For the purposes of this document, multiple substitutions are typically separated by slashes. For example, R94K/L78V refers to a double variant comprising the substitutions R94K and L78V. As used herein, "amino acid insertion" or "insertion" means the addition of an amino acid at a particular position in the parent polypeptide sequence. For example, insertion-94 indicates an insertion at position 94. As used herein, "amino acid deletion" or "deletion" means the removal of an amino acid at a particular position in the parent polypeptide sequence. For example, R94- indicates deletion of arginine at position 94.

The term "conservative modification" or "conservative sequence modification" as used herein means an amino acid modification that does not significantly affect or alter desired activities or properties of a peptide containing the amino acid sequence. Such conservative modifications include amino acid substitutions, insertions, and deletions. Modifications can be introduced into the antibody of the invention by standard techniques known in the art, such as site-directed mutagenesis and PCR-mediated mutagenesis. Conservative amino acid substitutions are substitutions in which amino acid residues are replaced with amino acid residues having similar side chains. A family of amino acid residues having similar side chains has been defined in the art. These families include amino acids containing basic side chains (e.g., lysine, arginine, histidine), acidic side chains (e.g., aspartic acid, glutamic acid), uncharged polar side chains (e.g., glycine, asparagine, serine, threonine, tyrosine, cysteine, tryptophan), non-polar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Therefore, one or more amino acid residues in the CDR regions or framework regions of the antibody of the invention can be replaced with other amino acid residues with similar side chains.

The term "autologous" as used herein and other grammatical forms thereof may refer to substances from the same source. For example, a sample (e.g., a cell) can be removed, processed and administered to the same individual (e.g., a patient) at a later time. The autologous process is different from the allogeneic process in which the donor and recipient are different individuals.

As used herein, "xenograft" and other grammatical forms thereof may include any procedure in which a recipient and a donor are from different species and cells, tissues or organs are transplanted, implanted or infused into the recipient. Transplantation of cells, organs and/or tissues described herein can be used as xenografts in humans. Xenografts include, but are not limited to, vascularized xenografts, partially vascularized xenografts, non-vascularized xenografts, xenogeneic dressings, xenogenic bandages, and xenogenic structures.

As used herein, "allograft" and other grammatical forms thereof (e.g., allogeneic transplantation) may include any procedure in which a recipient and a donor are from the same species but different individuals and cells, tissues or organs are transplanted, implanted or infused into the recipient. Transplantation of cells, organs and/or tissues as described herein can be used as allografts in humans. Allografts include, but are not limited to, vascularized allografts, partially vascularized allografts, non-vascularized allografts, allogeneic dressings, allogeneic bandages, and allogeneic structures.

As used herein, "autologous transplantation" and other grammatical forms thereof (e.g., autologous transplantation) may include any procedure in which a recipient and a donor are from the same individual and cells, tissues or organs are transplanted, implanted or infused into the recipient. Transplantation of cells, organs and/or tissues described herein can be used as autografts in humans. Autografts include, but are not limited to, vascular autologous transplantation, partial vascular autologous transplantation, non-vascularized autologous transplantation, autologous dressings, autologous bandages and autologous structures.

The term "chimeric antigen receptor" or "CAR" as used herein refers to an engineered molecule that can be expressed by an immune cell including, but not limited to, T cell or NK cell. CAR is expressed in T cells and redirects T cells to induce specific killing of target cells with a specificity determined by the artificial receptor. The extracellular binding domain of CAR can be derived from a murine, humanized or fully humanized monoclonal antibody.

The term "epitope" as used herein and other grammatical forms thereof may refer to a portion of an antigen that can be recognized by an antibody, B cell, T cell or engineered cell. For example, an epitope can be a tumor epitope or a pathogen epitope recognized by a TCR. Multiple epitopes within an antigen can also be recognized. Epitopes can also be mutated.

"Cell line" or "cell culture" means a bacterium, plant, insect or higher eukaryotic cell grown or maintained in vitro. The progeny of a cell may not be identical (in morphology, genotype or phenotype) to the maternal cell.

The term "engineered" as used herein and other grammatical forms thereof may refer to one or more changes in a nucleic acid, such as a nucleic acid within the genome of an organism. The term "engineered" can refer to alterations, additions, and/or deletions of genes. Engineered cells can also refer to cells having genes that are added, deleted, and/or altered. Engineered cells can also refer to cells that express CAR.

The term "transfection" as used herein refers to the introduction of an exogenous nucleic acid into a eukaryotic cell. Transfection can be achieved by various means known in the art, including calcium phosphate-DNA co-precipitation, DEAE-dextran mediated transfection, polyamine mediated transfection, electroporation, microinjection, liposome fusion, lipofection, protoplast fusion, retroviral infection and biolistics.

The term "stable transfection" or "stably transfect" refers to the introduction and integration of exogenous nucleic acids, DNAs or RNAs into the genome of a transfected cell. The term "stable transfectant" refers to a cell having exogenous nucleic acids stably integrated into genomic DNA.

As used herein, the terms "nucleic acid molecule encoding", "encoding DNA sequence" and "encoding DNA" refer to the order or sequence of deoxyribonucleotides along a deoxyribonucleotide chain. The order of these deoxyribonucleotides determines the order of the amino acids along the polypeptide (protein) chain. Therefore, a nucleic acid sequence encodes an amino acid sequence.

The term "individual" as used herein refers to any animal, such as a mammal or marsupial. Individuals of the invention include, but are not limited to, humans, non-human primates (e.g., rhesus monkeys or other types of macaques), mice, pigs, horses, donkeys, cows, sheep, rats and poultry of any kind.

The term "peripheral blood lymphocytes" (PBL) and other grammatical forms thereof as used herein may refer to lymphocytes circulating in blood (e.g., peripheral blood). Peripheral blood lymphocytes can refer to lymphocytes that are not restricted to organs. Peripheral blood lymphocytes can comprise T cells, NK cells, B cells or any combinations thereof.

The term "immune response cell" (or "immunoreactive cell", "immune effector cell" or "immune cell") as used herein may refer to a cell that can elicit an immune response. An immune response cell can also refer to a cell of the lymphoid or myeloid lineage. Examples of immune cells include, but are not limited to, T cells, such as $\alpha/\beta$ T cells and $\gamma/\delta$ T cells, B cells, natural killer (NK) cells, natural killer T (NKT) cells, mast cells and bone marrow-derived phagocytic cells, respective precursor cells and progenies thereof.

The term "T cell" and other grammatical forms thereof as used herein may refer to T cells from any source. For example, T cell can be a primary T cell, such as an autologous T cell or the like. T cell can also be of human or non-human.

The term "T cell activation" or "T cell trigger" as used herein and other grammatical forms thereof may refer to status of a T cell that is sufficiently stimulated to induce detectable cell proliferation, cytokine production, and/or detectable effector function. In some embodiments, "complete T cell activation" can be similar to triggering cytotoxicity of T cells. T cell activation can be measured using various assays known in the art. The assay can be an ELISA for measuring cytokine secretion, ELISPOT, a flow cytometry assay for measuring intracellular cytokine expression (CD107), a flow cytometry assay for measuring proliferation, and cytotoxicity assay for determining target cell elimination (51Cr release assay). In the assay, controls (non-engineered cells) are typically used to compare with engineered cells (CART) to determine the relative activation of engineered cells compared with controls. Furthermore, the assay can be performed by comparison with engineered cells that are incubated or contacted with target cells that do not express the target antigen. For example, the comparison can be a comparison with CD19-CART cells incubated with target cells that do not express CD19.

The term "sequence" as used herein and other grammatical forms thereof, when used in reference to a nucleotide sequence, may include DNA or RNA, and may be single-stranded or double-stranded. The nucleic acid sequence can be mutated. The nucleic acid sequence can be of any length, for example, a nucleic acid having 2 to 1,000,000 or more nucleotides (or any integer value there between or above), for example, about 100 to about 10,000 nucleotides or about 200 to about 500 nucleotides in length.

The term "effective amount" as used herein refers to an amount that provides therapeutic or prophylactic benefits.

The term "expression vector" as used herein, refers to a vector comprising a recombinant polynucleotide comprising an expression regulation sequence operably linked to a nucleotide sequence to be expressed. The expression vector contains sufficient cis-acting elements for expression; and other elements for expression can be provided by host cells or in vitro expression systems. Expression vectors include those known in the art, such as cosmids, plasmids (e.g., naked or contained in liposomes), and viruses (e.g., lentiviruses, retroviruses, adenoviruses, and adeno-associated viruses).

The term "lentivirus" as used herein refers to the genus of retroviridae family. Retroviruses are unique in retroviruses in their ability to infect non-dividing cells; they can deliver large amounts of genetic information into DNAs of host cells, therefore, they are one of the most efficient methods of gene delivery vectors. HIV, SIV and FIV are examples of lentiviruses. Vectors derived from lentiviruses provide a means to achieve significant levels of gene transfer in vivo.

The term "operably linked" as used herein, refers to a functional linkage between a regulatory sequence and a heterologous nucleic acid sequence, which results in expression of the latter. For example, when the first nucleic acid sequence is functionally associated to the second nucleic acid sequence, the first nucleic acid sequence is operably linked to the second nucleic acid sequence. For example, a promoter is operably linked to an encoding sequence if the promoter affects the transcription or expression of the encoding sequence. Typically, the operably linked DNA sequences are contiguous and, where necessary, two protein encoding regions are ligated in the same reading frame.

The term "promoter" as used herein, is defined as a DNA sequence that is recognized by the synthetic machinery or the introduced synthetic machinery being required to initiate specific transcription of a polynucleotide sequence.

The term "vector," as used herein, is a composition comprising an isolated nucleic acid and being used to deliver an isolated nucleic acid to the interior of a cell. A number of vectors are known in the art including, but not limited to, linear polynucleotides, polynucleotides associated with ionic or amphiphilic compounds, plasmids and viruses. Therefore, the term "vector" includes autonomously replicating plasmids or viruses. The term should also be interpreted to include non-plasmid and non-viral compounds that facilitate the transfer of nucleic acids into cells, such as polylysine compounds, liposomes, and the like. Examples of viral vectors include, but are not limited to, adenoviral vectors, adeno-associated viral vectors, retroviral vectors, and the like.

A "host cell" includes an individual cell or cell culture that can be or has been an acceptor of a target vector. Host cells include the progeny of a single host cell. Due to natural, accidental or intentional mutations, progeny may not necessarily be identical to the original parental cell, for example, in morphological properties or genomic DNA or total DNA. Host cells include cells that are transfected in vivo with the vectors of the invention. "Host cell" can refer to a prokaryotic cell, a eukaryotic cell, or a cell line that is cultured as a single cell entity that can be or has been used as a receptor for recombinant vectors or other transfer polynucleotides, and includes progeny cells that have been transfected.

The term "sequence identity" as used herein determines the percent identity by comparing two best matched sequences over a comparison window (e.g., at least 20 positions), wherein portions of the polynucleotide or polypeptide sequence in the comparison window can comprise addition or deletion (i.e., gap), for example, 20% or less of gaps (e.g., 5 to 15%, or 10 to 12%) compared with a reference sequence (which does not contain additions or deletions) for two best matched sequence. The percentage is usually calculated by determining the number of positions in which nucleotides or amino acid residues are the same in both sequences to produce the number of correctly matched positions. The sequence identity percentage can be obtained by dividing the number of correctly matched positions by the total number of positions in the reference sequence (that is, the window size) and multiplying the result by 100.

The term "disease" or "condition" or "disorder" as used herein, refers to any alteration or disorder that impairs or interferes with the normal function of a cell, tissue or organ. For example, the term "disease" includes, but is not limited to, a tumor, pathogen infection, autoimmune disease, T cell dysfunction disease, or defect in immune tolerance (e.g., transplant rejection).

The term "exogenous" as used herein, refers to a nucleic acid molecule or polypeptide that is not endogenously expressed in a cell, or the expression level of which is insufficient to achieve the function of overexpression. Therefore, "exogenous" includes recombinant nucleic acid molecules or polypeptides expressed in a cell, such as exogenous, heterologous and overexpressed nucleic acid molecules and polypeptides.

The term "regulation" as used herein refers to a positive or negative change. Example of regulation includes 1%, 2%, 10%, 25%, 50%, 75% or 100% variation.

As used herein, the term "treatment" refers to a clinical intervention in an attempt to alter an individual or treat a disease caused by a cell, both prophylactically and in a clinical pathological process. Therapeutic effects include, but are not limited to, preventing the occurrence or recurrence of the disease, alleviating symptoms, reducing the direct or indirect pathological consequences of any disease, preventing metastasis, slowing the progression of the disease, improving or ameliorating the condition, alleviating or improving the prognosis.

The term "constitutive expression" as used herein refers to expression under all physiological conditions.

The term "inducible expression" as used herein refers to expression under certain conditions, such as when a T cell binds to an antigen. One skilled in the art will know how to perform conventional "induced expression".

In some embodiments, an antigen binding unit comprising a light chain CDR and a heavy chain CDR is provided herein, wherein the antigen binding unit specifically binds to claudin 18A2 peptide; and wherein the antigen binding unit does not significantly bind to claudin 18A1 peptide.

In some embodiments, an antigen binding units comprising a light chain CDR and a heavy chain CDR is provided herein, wherein the antigen binding unit specifically binds to claudin 18A2 peptide; and wherein the antigen binding unit shows less non-specific binding to claudin 18A1 peptide, as compared with a reference antigen binding unit.

In some embodiments, an antigen binding unit described herein comprises a light chain CDR. The light chain CDR can be a complementarity determining region of an antigen binding unit. The light chain CDR may comprise a contiguous sequence of amino acid residues, or two or more contiguous sequence of amino acid residues spaced by non-complementarity determining regions, such as framework regions. In some embodiments, the light chain CDR comprises two or more light chain CDRs, which may be named to as light chain CDR-1, CDR-2, and the like. In some embodiments, the light chain CDR comprises three light chain CDRs, which may be named as light chain CDR-1 (LCDR1), light chain CDR-2 (LCDR2) and light chain CDR-3 (LCDR3), respectively. In some embodiments, a set of CDRs present on a common light chain can be collectively referred to as a light chain CDR.

In some embodiments, an antigen binding unit described herein comprises a heavy chain CDR. The heavy chain CDR can be a complementarity determining region of an antigen binding unit. The heavy chain CDR may comprise a contiguous sequence of amino acid residues, or two or more contiguous sequence of amino acid residues spaced by non-complementarity determining regions, such as framework regions. In some embodiments, the heavy chain CDR comprises two or more heavy chain CDRs, which may be named to as heavy chain CDR-1, CDR-2, and the like. In some embodiments, the heavy chain CDR comprises three heavy chain CDRs, which may be named as heavy chain CDR-1 (HCDR1), heavy chain CDR-2 (HCDR2) and heavy chain CDR-3 (HCDR3), respectively. In some embodiments, a set of CDRs present on a common heavy chain can be collectively referred to as a heavy chain CDR.

In some embodiments, an antigen binding unit comprising a light chain CDR and a heavy chain CDR is provided herein, wherein the light chain CDR comprises LCDR1, LCDR2 and LCDR3; and the heavy chain CDR comprises HCDR1, HCDR2 and HCDR3; the amino acid sequences of LCDR1, LCDR2 and LCDR3 are at least 80% identical to an amino acid sequence selected from the group consisting of SEQ ID NO:34, SEQ ID NO:35, SEQ ID NO:36, SEQ ID NO:40, SEQ ID NO:41, SEQ ID NO:42, SEQ ID NO:46, SEQ ID NO:47, SEQ ID NO:48, SEQ ID NO:52, SEQ ID NO:53 and SEQ ID NO:54; and the amino acid sequences of HCDR1, HCDR2 and HCDR3 are at least 80% identical to an amino acid sequence selected from the group consisting of SEQ ID NO:31, SEQ ID NO:32, SEQ ID NO:33, SEQ ID NO:37, SEQ ID NO:38, SEQ ID NO:39, SEQ ID NO:43, SEQ ID NO:44, SEQ ID NO:45, SEQ ID NO:49, SEQ ID NO:50, SEQ ID NO:51, SEQ ID NO:83 SEQ ID NO:84 and SEQ ID NO:85.

In some embodiments, an antigen binding unit comprising a light chain CDR and a heavy chain CDR is provided herein, wherein the light chain CDR comprises LCDR1, LCDR2 and LCDR3; and the heavy chain CDR comprises HCDR1, HCDR2 and HCDR3; wherein the amino acid sequences of LCDR1, LCDR2 and LCDR3 are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the following: SEQ ID NO:34, SEQ ID NO:35, SEQ ID NO:36, SEQ ID NO:40, SEQ ID NO:41, SEQ ID NO:42, SEQ ID NO:46, SEQ ID NO:47, SEQ ID NO:48, SEQ ID NO:52, SEQ ID NO:53 and SEQ ID NO:54; and wherein the amino acid sequences of HCDR1, HCDR2 and HCDR3 are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the group consisting of: SEQ ID NO:31, SEQ ID NO:32, SEQ ID NO:33, SEQ ID NO:37, SEQ ID NO: 38, SEQ ID NO:39, SEQ ID NO:43, SEQ ID NO:44, SEQ ID NO:45, SEQ ID NO:49, SEQ ID NO:50, SEQ ID NO:51, SEQ ID NO:83, SEQ ID NO:84 and SEQ ID NO:85.

In some embodiments, in the antigen binding unit herein, the light chain CDR comprises LCDR1, LCDR2 and LCDR3; and the heavy chain CDR comprises HCDR1, HCDR2 and HCDR3; wherein the LCDR1, LCDR2 and LCDR3 respectively have an amino acid sequence selected from the group consisting of: SEQ ID NO:34, SEQ ID NO:35, SEQ ID NO:36, SEQ ID NO:40, SEQ ID NO:41, SEQ ID NO:42, SEQ ID NO:46, SEQ ID NO:47, SEQ ID NO:48, SEQ ID NO:52, SEQ ID NO:53 and SEQ ID NO:54; and wherein said HCDR1, HCDR2 and HCDR3 respectively have an amino acid sequence selected from the group consisting of: SEQ ID NO:31 SEQ ID NO:32, SEQ ID NO:33, SEQ ID NO:37, SEQ ID NO:38, SEQ ID NO:39, SEQ ID NO:43, SEQ ID NO:44, SEQ ID NO:45, SEQ ID NO:49, SEQ ID NO:50, SEQ ID NO:51, SEQ ID NO:83, SEQ ID NO:84 and SEQ ID NO:85.

In some embodiments, an antigen binding unit is provided herein, wherein the LCDR1 comprises an amino acid sequences which is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the group consisting of: SEQ ID NO:34, SEQ ID NO:40, SEQ ID NO:46, and SEQ ID NO:52. In some embodiments, an antigen binding unit is provided herein, wherein the LCDR2 comprises an amino acid sequences which is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the group consisting of: SEQ ID NO:34, SEQ ID NO:41, SEQ ID NO:47 and SEQ ID NO:53.

In some embodiments, an antigen binding unit is provided herein, wherein the LCDR3 comprises an amino acid sequences which is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the group consisting of: SEQ ID NO:35, SEQ ID NO:42, SEQ ID NO:48, and SEQ ID NO:54. In some embodiments, an antigen binding unit is provided herein, wherein the HCDR1 comprises an amino acid sequences which is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the group consisting of: SEQ ID NO:31, SEQ ID NO:37, SEQ ID NO:43 and SEQ ID NO:49. In some embodiments, an antigen binding unit is provided herein, wherein the HCDR2 comprises an amino acid sequences which is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the group consisting of: SEQ ID NO:32, SEQ ID NO:38, SEQ ID NO:44, SEQ ID NO:50, SEQ ID NO:83, SEQ ID NO:84 and SEQ ID NO:85. In some embodiments, an antigen binding unit is provided herein, wherein the HCDR3 comprises an amino acid sequences which is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% identical to an amino acid sequence selected from the group consisting of: SEQ ID NO:33, SEQ ID NO:39, SEQ ID NO:45 and SEQ ID NO:51.

In some embodiments, an antigen binding unit of the invention binds to claudin 18A2 or a claudin 18A2 peptide. The term "claudin 18A2" or "claudin 18A2 peptide" (CLD18.2, CLD18A2, CLDN18A2, CLDN18.2, Claudin18.2 or Claudin18A2) herein may also refer to a homologue, orthologue, interspecies homolog, codon optimized form, truncated form, fragmented form, mutated form or any other known derivative form of a known claudin 18A2 sequence, such as a post-translational modification variant. In some embodiments, the claudin 18A2 or claudin 18A2 peptide is a peptide with GenBank accession number NP_001002026 (mRNA: NM_001002026). In some embodiments, the claudin 18A2 or claudin 18A2 peptide is a peptide comprising the amino acid sequence of SEQ ID NO:55.

In some embodiments, the antigen binding unit of the invention does not significantly bind to claudin 18A1 peptide. The term "claudin 18A1" or "claudin 18A1 peptide" (CLD18A1, CLD18.1, CLDN18A1, CLDN18.1, Claudin18.1 or Claudin18A1) herein may also refer to a homologue, orthologue, interspecies homolog, codon optimized form, truncated form, fragmented form, mutated form or any other known derivative form of a known claudin 18A1 sequence, such as a post-translational modification variant. In some embodiments, the claudin 18A1 or claudin 18A1 peptide is a peptide with GenBank accession number NP_057453 (mRNA: NM_016369). In some embodiments, the claudin 18A1 or claudin 18A1 peptide is a peptide comprising an amino acid sequence of SEQ ID NO:57.

Binding specificity can be determined by complementarity determining regions or CDRs, such as light chain CDRs or heavy chain CDRs. In many cases, binding specificity is determined by light chain CDRs and heavy chain CDRs. Compared with other reference antigens or reference peptides, a given heavy chain CDR, light chain CDR or a combination thereof provide a given binding pocket with greater affinity and/or specificity to claudin 18A2.

Binding of the antigen binding unit to claudin 18A2 peptide can be characterized or expressed by any method known in the art. For example, binding can be characterized by binding affinity, which can be the strength of the interaction between the antigen binding unit and the antigen. Binding affinity can be determined by any method known in the art, such as in vitro binding assays. For example, when tested in an in vitro binding assay using cells expressing claudin 18A2, the binding affinity of the antigen binding unit disclosed herein can be determined. The binding affinity of the tested antigen binding unit can be expressed as Kd, which is the equilibrium dissociation constant between the antibody and its respective antigen. In some cases, the antigen binding unit disclosed herein specifically binds to claudin 18A2, with Kd ranging from about 10 μM to about 1 mM. For example, the antigen binding unit can specifically bind to claudin 18A2 with a Kd of less than about 10 μM, 1 μM, 0.1 μM, 10 nM, 1 nM, 0.1 nM, 10 pM, 1 pM, 0.1 pM, 10 fM, 1 fM or less than 0.1 fM.

In some embodiments, the antigen binding unit does not exhibit significant binding to a reference peptide. In some examples, the binding level of the antigen binding unit to the reference peptide is not higher than 20% of the binding level of the antigen binding unit to claudin 18A2. For example, the binding level may be 20%, 19%, 18%, 17%, 16%, 15%, 14%, 13%, 12%, 11%, 10%, 9%, 8%, 7%, 6%, 5%, 4%, 3%, 2%, 1% or less than 1% of the binding level of the antigen binding unit to claudin 18A2. In some embodiments, the antigen binding unit herein binds to claudin 18A2 at a level that is 1 fold, 2 fold, 3 fold, 4 fold, 5 fold, 6 fold, 7 fold, 8 fold, 9 fold, 10 fold or more than 10 hold of the binding level to the reference peptide. In some embodiments, the reference peptide is claudin 18A1 peptide. In some embodiments, the reference peptide is a peptide comprising an amino acid sequence of SEQ ID NO:57. In some embodiments, the reference peptide is a peptide of SEQ ID NO:57.

In some embodiments, compared with a reference antigen binding unit, the antigen binding unit herein exhibits less non-specific binding to a reference peptide. In some embodiments, the non-specific binding level of the antigen binding unit herein to the reference peptide is 5%, 10%, 15%, 20%, 25%, 30%, 35%, 40%, 45%, 50%, 55%, 60%, 65%, 70%, 75%, 80%, 85%, 90%, 95% or 100% lower than that of the reference antigen binding unit to the reference peptide. In some embodiments, the non-specific binding level of the antigen binding unit herein to the reference peptide is 1 fold, 2 fold, 3 fold, 4 fold, 5 fold, 6 fold, 7 fold, 8 fold, 9 fold, 10 fold or more than 10 hold lower than that of the reference antigen binding unit to the reference peptide. In some embodiments, the reference antigen binding unit comprises a light chain of SEQ ID NO:86 or SEQ ID NO:88 and/or a heavy chain amino acid sequence of SEQ ID NO:87 or SEQ ID NO:89. In some embodiments, the reference antigen binding unit comprises an amino acid sequence of SEQ ID NO:86. In some embodiments, the reference antigen binding unit comprises an amino acid sequence of SEQ ID NO:87. In some embodiments, the reference antigen binding unit comprises an amino acid sequence of SEQ ID NO:88. In some embodiments, the reference antigen binding unit comprises an amino acid sequence of SEQ ID NO: 89. In some embodiments, the reference peptide is claudin 18A1 peptide. In some embodiments, the reference peptide is a peptide comprising an amino acid sequence of SEQ ID NO:57. In some embodiments, the reference peptide is a peptide of SEQ ID NO:57.

In some embodiments, the antigen binding unit is cytotoxic to a cell comprising claudin 18A2 peptide comprising an amino acid sequence of SEQ ID NO:55. The cytotoxicity level is at least 5%, 10%, 15%, 20%, 25%, 30%, 35%, 40% or 45%, when the ratio of the antigen binding unit to the target cell is 20:1, 10:1, 5:1, 3:1, 2.5:1, 1:1 or 1:3.

In some embodiments, the antigen binding unit does not have significant cytotoxicity to a cell comprising claudin 18A1 peptide but not comprising claudin 18A2 peptide, wherein the claudin 18A1 peptide comprises an amino acid sequence of SEQ ID NO:57, and the claudin 18A2 peptide comprises an amino acid sequence of SEQ ID NO:55. In some embodiments, the cytotoxicity level is not higher than 10%, 5%, 4%, 3%, 2% or 1%.

In some embodiments, an antibody specifically binding to claudin 18A2 is provided herein, characterized in that the antibody comprises a heavy chain CDR comprising an amino acid sequence selected from the group consisting of SEQ ID NOS:31, 32, 33, 37, 38, 39, 43 of 44, 45, 49, 50, 51, 83, 84, 85 or a variant thereof and/or a light chain CDR comprising an amino acid sequence selected from the group consisting of SEQ ID NOS:34, 35, 36, 40, 41, 42, 46, 47, 48, 52, 53, 54 or a variant thereof.

In some embodiments, an antibody is provided herein which is selected from the group consisting of (a) an antibody comprising a heavy chain variable region, wherein the heavy chain variable region has CDR1 comprising an amino acid sequence of SEQ ID NO:31, SEQ ID NO:37, SEQ ID NO:43 or SEQ ID NO:49, CDR2 comprising an amino acid sequence of SEQ ID NO:32, SEQ ID NO:38, SEQ ID NO:44, SEQ ID NO:50, SEQ ID NO:83, SEQ ID NO:84 or SEQ ID NO:85, and CDR3 comprising an amino acid sequence of SEQ ID NO:33, SEQ ID NO:39, SEQ ID NO:45 or SEQ ID NO:51; (b) an antibody comprising a light chain variable region, wherein the light chain variable region has CDR1 comprising an amino acid sequence of SEQ ID NO:34, SEQ ID NO:40, SEQ ID NO:46 or SEQ ID NO:52, CDR2 comprising an amino acid sequence of SEQ ID NO:35, SEQ ID NO:41, SEQ ID NO:47 or SEQ ID NO:53, and CDR3 comprising an amino acid sequence of SEQ ID NO:36, SEQ ID NO:42, SEQ ID NO:48 or SEQ ID NO:54; (c) an antibody comprising (a) a heavy chain variable region of said antibody and (b) a light chain variable region of said antibody; and (d) an antibody, recognizing the same antigenic determinant site as that of the antibody of any one of (a) to (c). In some embodiments, an antibody is provided herein, wherein the CDR1, CDR2 and CDR3 regions of the heavy chain variable region of the antibody are SEQ ID NO:31, SEQ ID NO:32, SEQ ID NO:33; or SEQ ID NO:37, SEQ ID NO:38, SEQ ID NO:39; or SEQ ID NO:43, SEQ ID NO:44, SEQ ID NO:45; or SEQ ID NO:49, SEQ ID NO:50, SEQ ID NO:51; or SEQ ID NO:31, SEQ ID NO:83, SEQ ID NO:33; or SEQ ID NO:31, SEQ ID NO:84, SEQ ID NO:33; or SEQ ID NO:49, SEQ ID NO:85, SEQ ID NO:51, respectively; and/or the CDR1, CDR2 and CDR3 regions of the light chain variable region of the antibody are SEQ ID NO:34, SEQ ID NO:35, SEQ ID NO:36; or SEQ ID NO:40, SEQ ID NO:41, SEQ ID NO:42; or SEQ ID NO:46, SEQ ID NO:47, SEQ ID NO:48; or SEQ ID NO:52, SEQ ID NO:53, SEQ ID NO:54, respectively.

In some embodiments, the amino acid sequences of the CDR1, CDR2 and CDR3 of the heavy chain of the antibody of the invention are selected from the group consisting of the amino acid sequences set forth in the following table or variants thereof:

TABLE 1

|   | HCDR1 | HCDR2 | HCDR3 |
|---|-------|-------|-------|
| A | SEQ ID NO: 31 | SEQ ID NO: 32 | SEQ ID NO: 33 |
| B | SEQ ID NO: 37 | SEQ ID NO: 38 | SEQ ID NO: 39 |
| C | SEQ ID NO: 43 | SEQ ID NO: 44 | SEQ ID NO: 45 |
| D | SEQ ID NO: 49 | SEQ ID NO: 50 | SEQ ID NO: 51 |
| E | SEQ ID NO: 31 | SEQ ID NO: 83 | SEQ ID NO: 33 |
| F | SEQ ID NO: 31 | SEQ ID NO: 84 | SEQ ID NO: 33 |
| G | SEQ ID NO: 49 | SEQ ID NO: 85 | SEQ ID NO: 51 |

In some embodiments, an antibody is provided herein, wherein the amino acid sequences of the light chain CDR1, CDR2 and CDR3 are selected from the group consisting of the amino acid sequences in the following table or variants thereof:

TABLE 2

|   | LCDR1 | LCDR2 | LCDR3 |
|---|-------|-------|-------|
| A | SEQ ID NO: 34 | SEQ ID NO: 35 | SEQ ID NO: 36 |
| B | SEQ ID NO: 40 | SEQ ID NO: 41 | SEQ ID NO: 42 |
| C | SEQ ID NO: 46 | SEQ ID NO: 47 | SEQ ID NO: 48 |
| D | SEQ ID NO: 52 | SEQ ID NO: 53 | SEQ ID NO: 54 |

In some embodiments, an antibody of the invention comprises a heavy chain variable region comprising an amino acid sequence selected from SEQ ID NOS:3, 7, 11, 15, 17, 19, 23, 27, 29 or variants thereof, and/or a light chain variable region comprising an amino acid sequenced sequence selected from SEQ ID NOS:1, 5, 9, 13, 21, 25 or a variant thereof. In some embodiments, the heavy chain variable region is SEQ ID NO:3 or a variant thereof and the light chain variable region is SEQ ID NO:1 or a variant thereof. In some embodiments, the heavy chain variable region is SEQ ID NO:7 or a variant thereof and the light chain variable region is SEQ ID NO:5 or a variant thereof. In some embodiments, the heavy chain variable region is SEQ ID NO:11 or a variant thereof and the light chain variable region is SEQ ID NO:9 or variant thereof. In some embodiments, the heavy chain variable region is SEQ ID NO:15 or a variant thereof and the light chain variable region is SEQ ID NO:13 or variant thereof. In some preferred embodiments, the amino acid sequences of the heavy chain CDR1, CDR2 and CDR3 are selected from the table below.

TABLE 3

|   | HCDR1 | HCDR2 | HCDR3 |
|---|-------|-------|-------|
| E | SEQ ID NO: 31 | SEQ ID NO: 83 | SEQ ID NO: 33 |
| F | SEQ ID NO: 31 | SEQ ID NO: 84 | SEQ ID NO: 33 |
| G | SEQ ID NO: 49 | SEQ ID NO: 85 | SEQ ID NO: 51 |

In some embodiments, an antibody of the invention comprises a heavy chain variable region comprising an amino acid sequence selected from SEQ ID NOS:17, 19, or variants thereof. In some embodiments, the heavy chain variable region is SEQ ID NO:17 or a variant thereof and the light chain variable region is SEQ ID NO:1 or a variant thereof. In some embodiments, the heavy chain variable region is SEQ ID NO:19 or a variant thereof and the light chain variable region is SEQ ID NO:1 or variant thereof.

In some embodiments, an antibody of the invention or a functional fragment thereof comprises a heavy chain variable region comprising an amino acid sequence selected from SEQ ID NOS:23, 27, 29 or a variant thereof, and/or a light chain variable region comprising an amino acid sequence selected from SEQ ID NOS: 21, 25 or a variant thereof. In some embodiments, the heavy chain variable region is SEQ ID NO:23 or a variant thereof and the light chain variable region is SEQ ID NO:21 or a variant thereof. In some embodiments, the heavy chain variable region is SEQ ID NO:27 or a variant thereof and the light chain variable region is SEQ ID NO:25 or a variant thereof. In some embodiments, the heavy chain variable region is SEQ ID NO:29 or a variant thereof and the light chain variable region is SEQ ID NO:25 or a variant thereof.

In some embodiments, an antigen binding unit or antibody of the invention is further linked or fused to another functional molecule. Accordingly, the invention also encompasses formed multifunctional immunoconjugates.

"Linked" or "fused" are used interchangeably herein. These terms means that two or more chemical elements or components are joined together by any means including chemical conjugation or recombinant methods. "In-frame fusion" means that two or more reading frames are joined in a manner maintaining the correct reading frame of the original open reading frame (ORF) to form a contiguous and longer ORF. Therefore, the resulting recombinant fusion protein is a single protein containing two or more fragments corresponding to the polypeptide encoded by the original ORF (these fragments are usually not so ligated in a natural state). The reading frames are contiguous throughout the fusion fragment, however the fragments may be physically or spatially separated by, for example, an in-frame joining sequence (e.g., "flexion").

The functional molecule is, for example used for the diagnosis or treatment of a tumor.

The term "tumor" as used herein refers to a disease characterized by pathological hyperplasia of cells or tissues, and subsequent migration or invasion of other tissues or organs. Tumor growth is usually uncontrolled and progressive and does not induce or inhibit normal cell proliferation. Tumors can affect a variety of cells, tissues or organs, including but not limited to, bladder, bone, brain, breast, cartilage, glial cells, esophagus, fallopian tubes, gallbladder, heart, intestine, kidney, liver, lung, lymph nodes, Nerve tissue, ovary, pancreas, prostate, skeletal muscle, skin, spinal cord, spleen, stomach, testis, thymus, thyroid, trachea, urethra, ureter, urethra, uterus, vaginal organs, or tissue or corresponding cells. Tumors include cancers such as sarcomas, carcinomas, or plasmacytomas (malignant tumors of plasma cells). The tumor of the present invention may include, but is not limited to, leukemia (such as acute leukemia, acute lymphocytic leukemia, acute myeloid leukemia, acute myeloid leukemia, acute promyelocytic leukemia, acute granulocyte-monocytic leukemia, acute monocytic leukemia, acute leukemia, chronic leukemia, chronic myeloid leukemia, chronic lymphocytic leukemia, polycythemia vera), lymphoma (Hodgkin's disease, non-Hodgkin's disease), primary macroglobulinemia Disease, heavy chain disease, solid tumors such as sarcoma and cancer (such as fibrosarcoma, mucinous sarcoma, liposarcoma, chondrosarcoma, osteosarcoma, chordoma, endothelial sarcoma, lymphangiosarcoma, angiosarcoma, lymphatic endothelial sarcoma, synovial vioma, mesothelioma, Ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, sweat gland cancer, sebaceous gland cancer, papillary cancer, papillary adenocarcinoma, carcinoma, bronchial carcinoma, medullary carcinoma, renal cell carcinoma, liver cancer, bile tube cancer, choriocarcinoma, fine Tumor, embryonic carcinoma, nephroblastoma, cervical cancer, uterine cancer, testicular cancer, lung cancer, small cell lung cancer, bladder cancer, epithelial cancer, glioma, astrocytoma, medulloblastoma, craniopharyngioma, Ependymoma, pineal tumor, hemangioblastoma, acoustic neuroma, oligodendroglioma, schwannomas, meningiomas, melanoma, neuroblastoma, retinoblastoma), esophageal cancer, gallbladder carcinoma, kidney cancer, multiple myeloma. Preferably, the "tumor" includes, but is not limited to, pancreatic cancer, liver cancer, lung cancer, gastric cancer, esophageal cancer, head and neck squamous cell carcinoma, prostate cancer, colon cancer, breast cancer, lymphoma, gallbladder cancer, Kidney cancer, leukemia, multiple myeloma, ovarian cancer, cervical cancer and glioma.

The functional molecule includes, for example, a tumor antigen, such as a tumor specific antigen (TSA) or a tumor associated antigen (TAA). TSA is unique to tumor cells and does not occur on other cells in the body. The TAA-associated antigen is not unique to tumor cells, but is expressed on normal cells under conditions in which the immune tolerance state to the antigen cannot be induced. Expression of an antigen on a tumor can occur under conditions that allow the immune system to respond to the antigen. When the immune system is immature and unable to respond, the TAA may be an antigen that is expressed on normal cells during fetal development, or they may be antigens that are normally present at very low levels on normal cells but are expressed at a higher level on tumor cells.

Non-limiting examples of TSA or TAA antigens include the following: differentiation antigens such as MART-1/MelanA (MART-I), gp100 (Pme117), tyrosinase, TRP-1, TRP-2, and tumor-specific multicenter antigens, such as MAGE-1, MAGE-3, BAGE, GAGE-1, GAGE-2, p15; overexpressed embryonic antigens, such as CEA; overexpressed oncogenes and mutant tumor suppressor genes, such as p53, Ras, HER-2/neu; unique tumor antigens caused by chromosomal translocations, such as BCR-ABL, E2A-PRL, H4-RET, IGH-IGK and MYL-RAR; and viral antigens, such as Epstein Barr virus antigen EBVA and human papilloma Virus (HPV) antigens E6 and E7, etc. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, β-catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\Cyclophilin C-related protein, TAAL6, TAG72, TLP and TPS.

In some embodiments, the "tumor antigen" includes, but is not limited to, prostate specific membrane antigen (PSMA), carcinoembryonic antigen (CEA), IL13Ralpha, HER-2, CD19, NY-ESO-1, HIV-1 Gag, Lewis Y, MART-1, gp100, tyrosinase, WT-I, hTERT, mesothelin, EGFR, EGFRvIII, phosphatidylinositol 3, EphA2, HER3, EpCAM, MUC1, MUC16, Folate receptor, CLDN6, CD30, CD138, ASGPR1, CDH16, GD2, 5T4, 8H9, αvβ6 integrin, B cell mature antigen (BCMA), B7-H3, B7-H6, CAIX, CA9, CD20, CD22, κ Kappa light chain, CD33, CD38, CD44, CD44v6, CD44v7/8, CD70, CD123, CD171, CSPG4, EGP2, EGP40, ERBB3, ERBB4, ErbB3/4, FAP, FAR, FBP, embryonic AchR, GD2, GD3, HLA-AI MAGE A1, MAGE3, HLA-A2, IL11Ra, KDR, Lambda, MCSP, NCAM, NKG2D ligand, PRAME, PSCA, PSC1, ROR1, Sp17, SURVIVIN, TAG72, TEM1, TEM8, VEGRR2, HMW-MAA, VEGF receptor, and/or fibronectin, tenascin or carcinoembryonic variants of tumor necrotic regions.

In some embodiments, the functional molecule is an interferon. In some embodiments, the interferon is a type I interferon.

The term "type I interferon" as used herein includes IFNα, IFNβ, IFN-ε, IFN-ω and the like. All type I interferons bind to specific cell surface receptors (so-called IFN-α/β receptors) consisting of two strands of IFNAR1 and IFNAR2. In some embodiments, the term "type I interferon" as used herein is IFNα or IFNβ. In some embodiments, the term "type I interferon" as used herein is IFNβ. In some embodiments, Type I interferon as used herein includes a human, mouse or synthetic Type I interferon. In some embodiments, the term "interferon α" as used herein may be a polypeptide having the sequence shown in NCBI aaa52724.1 or aaa52716.1 or aaa52725.1, or a polypeptide, the sequence of which has at least 85% identity to these sequences. In some embodiments, the term "interferon β" (INF-β) as used herein may be a protein having at least 85% identity to NCBI aac41702.1 or np_002167.1 or aah96152.1p41273 or NP_001552, or a fragment having the function of a tumor necrosis factor (TNF) ligand. In some embodiments, the interferon β is human interferon β. In some embodiments, the interferon β has an amino acid sequence of SEQ ID NO:92.

In some embodiments, Type I interferon may be naturally occurring, for example, isolated or purified from a mammal; or may be artificially prepared, for example, recombinant components or type I interferon can be produced according to conventional genetic engineering recombination techniques. Preferably, recombinant elements or type I interferons may be used in the present invention.

Amino acid sequences formed based on the type I interferon polypeptide sequence by substitution, deletion or addition of one or more amino acid residues are also included in the present invention. Appropriate replacement of amino acids is a technique well known in the art that can be readily implemented and ensures that the biological activities of a resulting molecule will not be altered. Based on these techniques, a skilled person will appreciate that, in general, altering a single amino acid in a non-essential region of a polypeptide does not substantially alter biological activities.

Polypeptides modified according to the type I interferon polypeptide sequence can also be used in the present invention. For example, a polypeptide modified to promote its half-life, effectiveness, metabolism and/or potency can be used. That is, any variation that does not affect the biological activities of a polypeptide can be used in the present invention.

Biologically active fragments of type I interferon polypeptide can be used in the present invention. As used herein, the meaning of a biologically active fragment refers to a polypeptide which, as part of a full length polypeptide, still retains all or part of the function of the full length polypeptide. Typically, the biologically active fragment retains at least 50% of the activities of the full length polypeptide. Under more preferred conditions, the active fragment is capable of retaining 60%, 70%, 80%, 90%, 95%, 99%, or 100% of the activities of the full length polypeptide.

In another aspect, the invention provides a chimeric antigen receptor comprising an extracellular antigen binding unit as described herein, a transmembrane domain, and an intracellular domain. The term "Chimeric Antigen Receptor (CAR)" as used herein refers to a tumor antigen binding domain fused to an intracellular signal transduction domain that activates T cells. Typically, the extracellular binding domain of CAR is derived from a mouse or humanized or human monoclonal antibody.

A chimeric antigen receptor typically comprises an extracellular antigen binding region or antigen binding unit. In some embodiments, the extracellular antigen binding unit is an antigen binding unit as described herein above.

In some embodiments, the extracellular antigen binding region can be of full human. In other instances, the extracellular antigen binding region can be humanized. In other instances, the extracellular antigen binding region can be murine or the chimera in the extracellular antigen binding region consists of amino acid sequences derived from at least two different animals. In some embodiments, the extracellular antigen binding region can be of non-human.

A variety of antigen binding regions can be designed. Non-limiting examples include single-chain variable fragments (scFv) derived from antibodies, fragments of antigen-binding regions (Fabs) selected from libraries, single-domain fragments, or natural ligands that bind to their cognate receptors. In some embodiments, the extracellular antigen binding region can comprise scFv, Fab or natural ligand, as well as any derivatives thereof. An extracellular antigen binding region can refer to a molecule other than an intact antibody, which can comprise a portion of an intact antibody and can bind to an antigen to which the intact antibody binds. Examples of antibody fragments can include, but are not limited to, Fv, Fab, Fab', Fab'-SH, F(ab')$_2$; bifunctional antibodies, linear antibodies; single-chain antibody molecules (e.g., scFv); and multispecific antibodies formed from antibody fragments.

An extracellular antigen binding region, such as a scFv, Fab or natural ligand, can be a part of a CAR that determines antigen specificity. The extracellular antigen binding region can bind to any complementary target. The extracellular antigen binding region can be derived from an antibody with known variable region sequence. The extracellular antigen binding region can be obtained from antibody sequences from available mouse hybridomas. Alternatively, extracellular antigen binding regions can be obtained from tumor cells or primary cells, such as tumor infiltrating lymphocytes (TIL) through whole external cutting sequencing.

In some embodiments, the binding specificity of the extracellular antigen binding region can be determined by a complementarity determining region or CDR, such as a light chain CDR or a heavy chain CDR. In many instances, binding specificity can be determined by light chain CDRs and heavy chain CDRs. Compared with other reference antigens, a combination of a given heavy chain CDR and light chain CDR can provide a given binding pocket with greater affinity and/or specificity to an antigen.

In certain aspects of any embodiment disclosed herein, the extracellular antigen binding region, such as scFv, can comprise a light chain CDR specific for an antigen. The light chain CDR can be a complementarity determining region of an antigen binding unit, such as scFv light chain of a CAR. The light chain CDRs may comprise contiguous sequence of amino acid residues, or two or more contiguous sequences of amino acid residues separated by non-complementarity determining regions (e.g., framework regions). In some embodiments, a light chain CDR can comprise two or more light chain CDRs, which can be named as light chain CDR-1, CDR-2, and the like. In some embodiments, the light chain CDRs can comprise three light chain CDRs, which can be named as light chain CDR-1, light chain CDR-2 and light chain CDR-3, respectively. In some examples, a set of CDRs present on a common light chain can be collectively named as light chain CDR.

In certain aspects of any embodiment disclosed herein, the extracellular antigen binding region, such as scFv, can comprise a heavy chain CDR specific for an antigen. The heavy chain CDR can be a complementarity determining region of an antigen binding unit, such as scFv heavy chain. The heavy chain CDRs may comprise contiguous sequence of amino acid residues, or two or more contiguous sequences of amino acid residues separated by non-complementarity determining regions (e.g., framework regions). In some embodiments, a heavy chain CDR can comprise two or more heavy chain CDRs, which can be named as heavy chain CDR-1, CDR-2, and the like. In some embodiments, the heavy chain CDRs can comprise three heavy chain CDRs, which can be named as heavy chain CDR-1, heavy chain CDR-2 and heavy chain CDR-3, respectively. In some examples, a set of CDRs present on a common heavy chain can be collectively named as heavy chain CDR.

The extracellular antigen binding region can be modified in various ways by genetic engineering. In some embodiments, the extracellular antigen binding region can be mutated such that the extracellular antigen binding region can be selected to have a higher affinity for its target. In some embodiments, the affinity of the extracellular antigen binding region for its target can be optimized for targets expressed at a low level on normal tissues. This optimization can be carried out to minimize potential toxicities. In other instances, clones of an extracellular antigen binding region with a higher affinity for the membrane-bound form of a target may be preferred over the counterpart in a soluble form. Such modifications can be performed, since different levels of soluble forms of a target can also be detected and their targeting can cause undesirable toxicity.

In some embodiments, the extracellular antigen binding region comprises a hinge or spacer region. The terms "hinge" and "spacer region" can be used interchangeably. The hinge can be considered as a part of a CAR for rendering flexibility to the extracellular antigen binding region. In some embodiments, the hinge can be used to detect CAR on the surface of a cell, especially when antibodies detecting the extracellular antigen binding region are ineffective or available. For example, it may be necessary to optimize the length of the hinge derived from an immunoglobulin, depending on the location of the epitope on the target that the extracellular antigen binding region targets.

In some embodiments, the hinge may not belong to an immunoglobulin, but to another molecule, such as the native hinge of a CD8a molecule. CD8a hinge may contain cysteine and proline residues known to play a role in the interaction of CD8 co-receptor and MHC molecule. The cysteine and proline residues can affect the performance of the CAR.

The CAR hinge can be adjustable in size. This morphology of the immunological synapse between an immune response cell and a target cell also defines the distance that cannot be functionally bridged by a CAR due to the distal membrane epitope on a target molecule at the cell surface, that is, the synaptic distance cannot reach an approximation that a signal can be conducted even using a CAR with short hinge. Similarly, for the membrane proximal target antigen epitope of a CAR, signal outputs can only be observed in the context of a CAR with long hinge. The hinge can be adjusted depending on the used extracellular antigen binding region. The hinge can be of any length.

The transmembrane domain can anchor a CAR to the plasma membrane of a cell. The natural transmembrane portion of CD28 can be used for a CAR. In other instances, the natural transmembrane portion of CD8a can also be used in a CAR. "CD8" may be a protein having at least 85, 90, 95, 96, 97, 98, 99 or 100% identity to NCBI reference number: NP_001759 or a fragment thereof having stimulatory activities. A "CD8 nucleic acid molecule" may be a polynucleotide encoding a CD8 polypeptide, and in some instances, the transmembrane region may be a natural transmembrane portion of CD28. "CD28" may be a protein having at least 85, 90, 95, 96, 97, 98, 99 or 100% identity to NCBI reference number: NP_006130 or a fragment thereof having stimulatory activities. A "CD28 nucleic acid molecule" can be a polynucleotide encoding a CD28 polypeptide. In some embodiments, the transmembrane portion can comprise a CD8α region.

The intracellular signaling region of a CAR may be responsible for activating at least one effector functions of an immune response cell into which a CAR has been placed. CAR can induce effector functions of T cells, for example, the effector function is cytolytic activity or helper activity, including secretion of cytokines. Therefore, the term intracellular signaling region refers to a protein portion that transduces effector function signals and directs the cell to perform a specific function. The entire intracellular signaling region can generally be used, however, in many cases, it is not necessary to use the entire chain of the signal domain. In some embodiments, a truncated portion of an intracellular signaling region is used. In some embodiments, the term intracellular signaling region is therefore intended to include any truncated portion of an intracellular signaling region sufficient to transduce effector function signals.

Preferred examples of signal domains for use in CAR may include cytoplasmic sequences of T cell receptors (TCRs) and co-receptors that act synergistically to initiate signal transduction after target-receptor binding, as well as any derivatives thereof or variant sequences and any synthetic sequences of these sequences that have the same functionality.

In some embodiments, the intracellular signaling region can contain a known signal motif for an immunoreceptor tyrosine activation motif (ITAM). Examples of ITAMs containing cytoplasmic signaling sequences include those derived from TCRζ, FcRγ, FcRβ, CD3γ, CD3δ, CD3ε, CD5, CD22, CD79a, CD79b and CD66d. However, in a preferred embodiment, the intracellular signal domain is derived from a CD3ζ chain.

An example of a T cell signaling domain containing one or more ITAM motifs is CD3ζ domain, also known as T cell receptor T3ζ chain or CD247. This domain is a part of T cell receptor-CD3ζ complex and plays an important role in binding antigen recognition of several intracellular signal transduction pathways to the main effector activation of T cells. As used herein, CD3ζ refers primarily to human CD3ζ and isoforms thereof, as known from Swissprot entry P20963, including proteins having substantially identical sequences. As a part of a chimeric antigen receptor, it is reiterated that whole T cell receptor T3ζ chain is not required, and that any derivative of the signal domain comprising T cell receptor T3ζ chain is suitable, including any functional equivalent thereof.

The intracellular signaling domain can be selected from any domains in Table 1. In some embodiments, the domain can be modified such that identity to the reference domain can range from about 50% to about 100%. Any domain in Table 1 can be modified such that the modified form can comprise about 50, 60, 70, 80, 90, 95, 96, 97, 98, 99 or up to about 100% identity.

The intracellular signaling region of CAR may further comprise one or more costimulatory domains. The intracellular signaling region may comprise a single costimulatory domain, such as an chain (first generation of CAR) or it and CD28 or 4-1BB (second generation of CAR). In other examples, the intracellular signaling region can comprise two costimulatory domains, such as CD28/OX40 or CD28/4-1BB (third generation).

Together with intracellular signaling domains such as CD8, these costimulatory domains can generate downstream activation of the kinase pathway, thereby supporting gene transcription and functional cellular responses. The co-stimulatory domain of CAR can activate CD28 (phosphatidylinositol-4,5-diphosphate 3-kinase) or 4-1BB/OX40 (TNF-receptor-associated factor adaptor protein) pathways as well as MAPK and Akt activation-associated proximal signaling protein.

In some instances, signals generated by a CAR may be combined with an auxiliary or costimulatory signal. For costimulatory signaling domains, chimeric antigen receptor-like complexes can be designed to contain several possible costimulatory signal domains. As is well known in the art, in naive T cells, only ligation of T cell receptors is not sufficient to induce complete activation of T cells into cytotoxic T cells. A second co-stimulatory signal is required for complete productive T cell activation. Several receptors have been reported to provide co-stimulation for T cell activation including, but not limited to, CD28, OX40, CD27, CD2, CD5, ICAM-1, LFA-1 (CD11a/CD18), 4-1BBL, MyD88 and 4-1BB. The signal transduction pathways used by these costimulatory molecules can act synergistically with the primary T cell receptor activation signal. The signals provided by these costimulatory signaling regions can act synergistically with primary effect activation signals derived from one or more ITAM motifs (e.g., the CD3zeta signal transduction domain) and can fulfill the requirements for T cell activation.

In some embodiments, the addition of a costimulatory domain to a chimeric antigen receptor-like complex can enhance the efficacy and durability of engineered cells. In other embodiments, the T cell signaling domain and the costimulatory domain are fused to each other to form a signaling region.

the target. For example, in some embodiments, the chimeric antigen receptor is present on a cytotoxic cell, such as an NK cell or a cytotoxic T cell, and, when activated by a target, the toxicity of the cytotoxic cell to the target cell can be increased. In some embodiments, the chimeric antigen receptors herein can increase the effect of immunoreactive cells on cells expressing claudin 18A2, such as tumor cells. In some embodiments, compared with a cell that does not express a chimeric antigen receptor herein, the cytotoxic effect of a cell expressing a chimeric antigen receptor described herein on cells expressing claudin 18A2 is increased by at least 10%, at least 15. %, at least 20%, at least 25%, at least 30%, at least 35%, at least 40%, at least 45%, at least 50%, at least 55%, at least 60%, at least 65%,

TABLE 4

Costimulatory domain

| Gene marker | Abbreviation | Name |
|---|---|---|
| CD27 | CD27; T14; S152; Tp55; TNFRSF7; S152. LPFS2 | CD27 molecule |
| CD28 | Tp44; CD28; CD28 antigen | CD28 molecule |
| TNFRSF9 | ILA; 4-1BB; CD137; CDw137 | Tumor necrosis factor receptor superfamily member 9 |
| TNFRSF4 | OX40; ACT35; CD134; IMD16; TXGP1L | Tumor necrosis factor receptor superfamily member 4 |
| TNFRSF8 | CD30; Ki-1; D1S166E | Tumor necrosis factor receptor superfamily member 8 |
| CD40LG | IGM; IMD3; TRAP; gp39; CD154; CD40L; HIGM1; T-BAM; TNFSF5; hCD40L | CD40 ligand |
| ICOS | AILIM; CD278; CVID1 | Inducible T cell costimulator |
| ITGB2 | LAD; CD18; MF17; MFI7; LCAMB; LFA-1; MAC-1 | Integrin β2 (Complement component 3 receptor 3 and 4 subunits) |
| CD2 | T11; SRBC; LFA-2 | CD2 molecule |
| CD7 | GP40; TP41; Tp40; LEU-9 | CD7 molecule |
| KLRC2 | NKG2C; CD159c; NKG2-C | Killer cell lectin-like receptor subfamily C, member 2 |
| TNFRSF18 | AITR; GITR; CD357; GITR-D | Tumor necrosis factor receptor superfamily member 18 |
| TNFRSF14 | TR2; ATAR; HVEA; HVEM; CD270; LIGHTR | Tumor necrosis factor receptor superfamily member 14 |
| HAVCR1 | TIM; KIM1; TIM1; CD365; HAVCR; KIM-1; TIM-1; TIMD1; TIMD-1; HAVCR-1 | Hepatitis A virus cell receptor 1 |
| LGALS9 | HUAT; LGALS9A, Galectin-9 | Lectin, galactoside binding, soluble, 9 |
| CD83 | BL11; HB15 | CD83 molecule |

The chimeric antigen receptor binds to the target antigen. When T cell activation is measured in vitro or ex vivo, the target antigen can be obtained or isolated from various sources. The target antigen as used herein is an antigen or an immunological epitope on an antigen that is critical in mammals for immune recognition and ultimately elimination or control of pathogenic factors or disease states. The immune recognition can be a cell and/or a body fluid. In the case of intracellular pathogens and cancer, the immune recognition can be, for example, a T lymphocyte reaction.

In some embodiments, the target antigen comprises an antigen associated with a pre-cancerous or proliferative state. Target antigens may also be associated with or caused by cancer. For example, in some embodiments, a chimeric antigen receptor of the invention recognizes and binds to a tumor antigen comprising TSA and TAA as described herein above.

In some embodiments, when a chimeric antigen receptor herein is present on the plasma membrane of a cell, binds to its target and is activated, the cell expressing the chimeric antigen receptor can produce cytotoxicity to a cell carrying at least 70%, at least 75%, at least 80%, at least 85%, at least 90%, at least 95%, at least 1 times, at least 1.5 times, at least 2 times, at least 2.5 times, at least 3 times, at least 3.5 times, at least 4 times, at least 4.5 times, at least 5 times, at least 6 times, at least 7 times, at least 8 times, at least 9 times or at least 10 times.

In some embodiments, when a chimeric antigen receptor herein is present on the plasma membrane of a cell, binds to its target and is activated, a chimeric antigen receptor herein does not induce significant cytotoxicity on cells comprising claudin 18A1 peptide but not claudin 18A2 peptide. In some embodiments, the cytotoxicity level is no greater than 10%, 5%, 4%, 3%, 2% or 1%.

A transgene encoding a receptor or a CAR binding a target antigen can be incorporated into a cell. For example, a transgene can be incorporated into an immune response cell, such as a T cell. When inserted into a cell, the transgene can be a complementary DNA (cDNA) fragment that is a copy of messenger RNA (mRNA); or the gene itself (with or without introns) located in the original region of its genomic DNA.

A nucleic acid encoding a transgene sequence, such as DNA, can be randomly inserted into the chromosome of a cell. Random integration can be produced by any method that introduces a nucleic acid, such as DNA, into a cell. For example, the method can include, but is not limited to, electroporation, ultrasound, use of a gene gun, lipofection, calcium phosphate transfection, use of dendrimers, microinjection, and use of virus vector including adenovirus, AAV, and retroviral vectors, and/or type II ribozyme.

The DNA encoding the transgene can also be designed to include a reporter gene such that the presence of the transgene or its expression product can be detected by activation of the reporter gene. Any reporter gene can be used, such as those described above. The cells containing the transgene can be selected by selecting cells in the cell culture in which the reporter gene has been activated.

Expression of CAR can be verified by expression assays. such as qPCR or by measuring the level of RNA. The expression level can also indicate the number of copies. For example, if the expression level is very high, this may indicate that more than one copy of a CAR are integrated into the genome. Alternatively, high expression may indicate that the transgene is integrated in a high transcribed region, such as near a highly expressed promoter. Expression can also be verified by measuring protein levels, for example by Western blotting.

In some embodiments, an immune response cell of the invention may comprise one or more transgenes. The one or more transgenes can express a CAR protein that recognizes and binds to at least one epitope on an antigen or binds to a mutant epitope on the antigen. CAR can be a functional CAR. In some embodiments, the immune response cells of the invention may comprise one or more CARs, or they may comprise a single CAR and a secondary engineered receptor.

In some embodiments, the transgene can encode a suicide gene. As evidenced by many effective treatments for cancer patients, CAR immune response cells can cause tumor regression while with toxicity. In some embodiments, when the target antigen is shared in normal tissues and tumor cells, the CAR immune response cells may not be able to distinguish between tumors and normal tissues ("on-target/off-target toxicity"). In other cases, a systemic disturbance of the immune system, called cytokine release syndrome (CRS), can occur. The CRS may comprise a systemic inflammatory response syndrome or a cytokine storm, which may be a consequence of rapid expansion of the CAR immune response cells in vivo. CRS is a condition characterized by fever and hypotension, which can lead to multiple organ failure. In most cases, the toxicity is associated with in vivo expansion of infused CAR immune response cells, which can cause an overall disturbance of the immune system, as well as release high levels of pro-inflammatory cytokines such as TNFα and IL-6. Suicide genes can induce the elimination of CAR immunoreactive cells. The suicide gene may be any gene that induces apoptosis in CAR immunoreactive cells. A suicide gene can be encoded in the viral vector together with the antigen-binding receptor. The encoding of the suicide gene allows for the alleviation or complete abortion of the toxicity caused by in vivo expansion of the infused CAR immune response cells under specific conditions.

In some embodiments, CAR immunoreactive cells for an antigen that are present in normal tissues can be produced such that they transiently express CAR, e.g., after electroporation of the mRNA encoding the receptor. In addition, in the case of severe target toxicity, CAR immunoreactive cells can be substantially eliminated through an effort to further strengthen CAR immunoreactive cells by including a safety switch.

In some embodiments, the CAR-encoding vector can be combined with, for example, an inducible caspase-9 gene (activated by a dimeric chemical inducer) or a truncated form of EGF receptor R (activated by the monoclonal antibody Cetuximab) or RQR8 safety switch.

One or more transgenes used herein may be from different species. For example, one or more transgenes can comprise a human gene, a mouse gene, a rat gene, a porcine gene, a bovine gene, a dog gene, a cat gene, a monkey gene, a chimpanzee gene, or any combination thereof. For example, a transgene can be from a human having a human genetic sequence. One or more transgenes may comprise a human gene. In some cases, one or more transgenes are not adenoviral genes.

As described above, a transgene can be inserted into the genome of an immunoreactive cell in a random or site-specific manner. For example, a transgene can be inserted into a random site in the genome of an immune cell. These transgenes can be functional, for example, fully functional when inserted into any part of the genome. For example, a transgene can encode its own promoter or can be inserted into a position controlled by internal promoter. Alternatively, the transgene can be inserted into a gene, such as an intron of a gene or an exon, promoter or non-coding region of a gene. A transgene can be inserted to disrupt a gene, such as an endogenous immune checkpoint.

In some embodiments, more than one copy of a transgene can be inserted into multiple random sites within the genome. For example, multiple copies can be inserted into random sites in the genome. This may result in an increase in overall expression compared with random insertion of the transgene for one time. Alternatively, a copy of the transgene can be inserted into a gene and another copy of the transgene can be inserted into a different gene. The transgene can be targeted such that it can be inserted into a specific site in the genome of an immunoreactive cell.

In some embodiments, a polynucleic acid comprising a sequence encoding an antigen-binding receptor can take the form of a plasmid vector. The plasmid vector may comprise a promoter. In some cases, the promoter can be constitutive. In some embodiments, the promoter is inducible. The promoter may be or may be derived from CMV, U6, MND or EF1a. In some embodiments, the promoter can be adjacent to the CAR sequence. In some embodiments, the plasmid vector further comprises a splice acceptor. In some embodiments, the splice acceptor can be adjacent to a CAR sequence. The promoter sequence can be PKG or MND promoter. MND promoter may be a synthetic promoter comprising U3 region of MoMuLV LTR modified with myeloproliferative sarcoma virus enhancer.

In some embodiments, a polynucleic acid encoding a receptor of interest can be designed to be delivered to a cell by non-viral techniques. In some cases, the polynucleic acid can be a GMP-compatible reagent.

Expression of a polynucleic acid encoding a receptor that binds to an antigen or a CAR can be controlled by one or more promoters. Promoters can be ubiquitous, constitutive (unrestricted promoters, allowing for continuous transcription of related genes), tissue-specific promoters or inducible promoters. Expression of a transgene inserted adjacent to or proximate to a promoter can be modulated. For example, a transgene can be inserted near or beside a ubiquitous promoter. Some ubiquitous promoters may be CAGGS promoter, hCMV promoter, PGK promoter, SV40 promoter or ROSA26 promoter.

Promoters can be endogenous or exogenous. For example, one or more transgenes can be inserted adjacent to or proximate to endogenous or exogenous ROSA26 promoter. Furthermore, the promoter may be specific for immunoreactive cells. For example, one or more transgenes can be inserted adjacent to or proximate to porcine ROSA26 promoter.

Tissue-specific promoters or cell-specific promoters can be used to control the location of expression. For example, one or more transgenes can be inserted into proximity to a tissue-specific promoter. The tissue-specific promoter may be FABP promoter, Lck promoter, CamKII promoter, CD19 promoter, keratin promoter, albumin promoter, aP2 promoter, insulin promoter, MCK promoter, MyHC promoter, WAP promoter or Col2A promoter.

Inducible promoters can also be used. These inducible promoters can be turned on and off by adding or removing an inducer, if necessary. The inducible promoter is contemplated to be, but not limited to, Lac, tac, trc, trp, araBAD, phoA, recA, proU, cst-1, tetA, cadA, nar, PL, cspA, T7, VHB, Mx and/or Trex.

The term "inducible promoter" as used herein is a controlled promoter which does not express or underexpresses a gene operably linked thereto before the desired conditions are reached, and expresses or expresses at high level a gene operably linked thereto when the desired conditions are achieved under. For example, in some embodiments, an inducible promoter of the present application does not express or underexpress a gene operably linked thereto under normal or hyperoxic conditions in a cell, and in response to a reduced oxygen content in the cell, a gene operably linked thereto is expressed or overexpressed under hypoxic conditions. In some embodiments, an inducible promoter used herein includes Hypoxia-Inducible Transcription factor-1α (HIF-1α). In some embodiments, the term "inducible promoter" as used herein refers to an "immune cell-inducible promoter" that does not express or underexpresses a gene operably linked thereto before an immune response cell contacts an antigen or when the immune response cell is not activated, while only when the immune response cell contacts the antigen or the immune response cell is activated, the promoter drives the gene operably linked to express at a high level or express under conditions such as hypoxia. In some embodiments, the "immune cell-inducible promoter" comprises a NFAT (activated T cell nuclear factor) type promoter.

As used herein, "NFAT-type promoter" refers to a class of promoters that regulate the expression of a gene operably linked thereto based on NFAT binding activity.

NFAT is a general term for a family of transcription factors that play an important role in immune responses. One or more members of the NFAT family are expressed in most cells of the immune system. NFAT is also involved in the development of the heart, skeletal muscle and nervous system.

The NFAT transcription factor family consists of five members, NFAT1, NFAT2, NFAT3, NFAT4 and NFAT5. NFAT1 to NFAT4 are regulated by calcium signals. Calcium signaling is critical for NFAT activation since calmodulin (CaM) activates serine/threonine phosphatase calcineurin (CN). Activated CN rapidly dephosphorylates the serine-rich region (SRR) and SP repeats at the amino terminus of NFAT protein, resulting in a conformational change that exposes nuclear localization signals leading to NFAT entry into the nucleus.

Based on the role of NFAT in the transcriptional expression of cytokines during T cell activation, it can be used to modulate the immune cell-inducible promoters described herein, thereby expressing or expressing at high levels a gene operably linked thereto when the immune response cells contact the antigen and are activated.

A nucleic acid of the invention may comprise any suitable nucleotide sequence encoding NFAT type promoter (or a functional part or a functional variant thereof). As used herein, "NFAT-type promoter" refers to one or more NFAT response elements linked to the minimal promoter of any gene expressed by a T cell. Preferably, the minimal promoter of the gene expressed by T cells is the smallest human IL-2 promoter. The NFAT response element can include, for example, NFAT1, NFAT2, NFAT3, and/or NFAT4 response elements. In some embodiments, "NFAT-type promoter" as described herein includes more than one NFAT binding motif. For example, the "NFAT-type promoter" can include 2, 3, 4, 5, 6, 7, 8, 9, 10 or more NFAT binding motifs. In some embodiments, the "NFAT-type promoter" includes up to 12 NFAT binding motifs. In some embodiments, the "NFAT-type promoter" can be a promoter consisting of a plurality of NFAT-binding motifs in series with a promoter, such as IL2 minimal promoter. In some embodiments, the NFAT-type promoter described herein comprises six NFAT binding motifs, designated $(NFAT)_6$. For convenience purposes, the $(NFAT)_6$ is also referred to as NFAT6. In some embodiments, the NFAT6 also represents 6 repeated NFAT binding motifs (SEQ ID NO:94) in the NFAT-type promoter.

Furthermore, the transgenic sequences may also include transcriptional or translational regulatory sequences, such as promoters, enhancers, insulators, internal ribosome entry sites, sequences encoding 2A peptides and/or polyadenylation signals, although not essential for expression.

In some embodiments, the transgene encodes a receptor or CAR that binds to the antigen, wherein the transgene is inserted into a safe harbor such that the antigen-binding receptor is expressed. In some embodiments, the transgene is inserted into PD1 and/or CTLA-4 locus. In other cases, the transgene is delivered as a lentivirus to the cells for random insertion, while a PD1- or CTLA-4 specific nuclease can be provided as mRNA. In some embodiments, the transgene is delivered by a viral vector system such as retrovirus, AAV or adenovirus and mRNA encoding a safe harbor specific nuclease (e.g., AAVS1, CCR5, albumin or HPRT). Cells can also be treated with mRNA encoding PD1 and/or CTLA-4 specific nucleases. In some embodiments, the polynucleotide encoding the CAR is provided by a viral delivery system together with an mRNA encoding an HPRT-specific nuclease and a PD1- or CTLA-4 specific nuclease. CARs that can be used with the methods and compositions disclosed herein can include all types of these chimeric proteins.

In some embodiments, a transgene can be introduced into an immunoreactive cell using a retroviral vector (γ-retroviral or lentiviral vector). For example, a transgene encoding a CAR or any receptor that binds an antigen, or a variant or fragment thereof, can be cloned into a retroviral vector and can be driven from an endogenous promoter, a retroviral long terminal repeat or target cell type-specific promoter. Non-viral vectors can also be used. Non-viral vector delivery systems can include a DNA plasmid, a naked nucleic acid, and a nucleic acid complexed with a delivery vehicle such as a liposome or poloxamer.

Many virus-based systems have been developed for transferring genes into mammalian cells. For example, retroviruses provide a convenient platform for gene delivery systems. The selected gene can be inserted into a vector and packaged in retroviral particles using techniques known in the art. Vectors derived from retroviruses such as lentiviruses are suitable tools for achieving long-term gene transfer, since they allow long-term stable integration of the transgene and its propagation in daughter cells. Lentiviral vectors have additional advantages over vectors derived from retroviruses such as murine leukemia virus, since they can transduce non-proliferating cells. They also have additional advantages of low immunogenicity. An advantage of adenoviral vectors is that they do not fuse into the genome of a target cell, thereby bypassing negative integration-related events.

Cells can be transfected with a transgene encoding the antigen-binding receptor. The concentration of a transgene can range from about 100 picograms to about 50 micrograms. In some embodiments, the amount of nucleic acid (e.g., ssDNA, dsDNA or RNA) introduced into a cell can be altered to optimize transfection efficiency and/or cell viability. For example, 1 microgram of dsDNA can be added to each cell sample for electroporation. In some embodiments, the amount of nucleic acid (e.g., double-stranded DNA) required for optimal transfection efficiency and/or cell viability varies depending on the cell type. In some embodiments, the amount of nucleic acid (e.g., dsDNA) used for each sample can directly correspond to transfection efficiency and/or cell viability, for example, a range of transfection concentrations. The transgene encoded by the vector can be integrated into the genome of a cell. In some embodiments, the transgene encoded by the vector is forward integrated. In other cases, the transgene encoded by the vector is reverse integrated.

The vector is delivered into an individual patient typically by systemic administration (e.g., intravenous, intraperitoneal, intramuscular, subcutaneous, or intracranial infusion) or topical application, as described below. Alternatively, the vector can be delivered ex vivo to a cell, such as a cell removed from an individual patient (e.g., lymphocytes, T cells, bone marrow aspirate, tissue biopsy), and then the cells into which the vector is incorporated is typically selected and implanted in a patient. Cells can be expanded before or after selection.

Suitable immunoreactive cells for expression of a receptor that binds to an antigen may be cells that are autologous or non-autologous to the individual in need thereof.

A suitable source of immune response cells can be obtained from the individual. In some cases, T cells can be obtained. T cells can be obtained from a number of sources, including PBMC, bone marrow, lymph node tissue, cord blood, thymus tissue, and tissues from infected sites, ascites, pleural effusion, spleen tissue and tumor tissue. In some cases, T cells can be obtained from blood collected from the individual using any number of techniques known to a skilled person, such as Ficoll separation. In some embodiments, cells from circulating blood of an individual are obtained by apheresis. Apheresis products typically contain lymphocytes, including T cells, monocytes, granulocytes, B cells, other nucleated white blood cells, red blood cells, and platelets. In some embodiments, cells collected by apheresis can be washed to remove plasma fractions and placed in a suitable buffer or medium for subsequent processing steps.

Alternatively, cells can be derived from a healthy donor, from a patient diagnosed with cancer or a patient diagnosed with an infection. In some embodiments, the cells can be a part of a mixed cell population with different phenotypic characteristics. Cell lines can also be obtained from transformed T cells according to the methods previously described. Cells can also be obtained from a cell therapy library. Modified cells that are resistant to immunosuppressive therapy can be obtained by any of the methods described herein. It is also possible to select an appropriate cell population prior to modification. The engineered cell population can also be selected after modification. Engineered cells can be used for autologous transplantation. Alternatively, the cells can be used for allogeneic transplantation. In some embodiments, the cells are administered to a sample for identifying the same patient of a cancer-associated target sequence. In other instances, the cells are administered to a patient other than a patient whose sample is used to identify a cancer-associated target sequence.

In some embodiments, suitable primary cells include peripheral blood mononuclear cells (PBMC), peripheral blood lymphocytes (PBL), and other blood cell subpopulations such as, but not limited to, T cells, natural killer cells, monocytes, Natural killer T cells, monocyte precursor cells, hematopoietic stem cells or non-pluripotent stem cells. In some embodiments, the cell can be any immune cell, including any T cell such as a tumor infiltrating cell (TIL), such as a CD3+ T cell, a CD4+ T cell, a CD8+ T cell, or any other type of T cell. T cells can also include memory T cells, memory stem T cells, or effector T cells. It is also possible to select T cells from a large population, for example to select T cells from whole blood. T cells can also be expanded from a large population. T cells may also be inclined to specific populations and phenotypes. For example, T cell can be inclined to a phenotype comprising CD45RO(−), CCR7 (+), CD45RA(+), CD62L(+), CD27(+), CD28(+) and/or IL-7Ra(+). Suitable cells may have one or more of the following markers: CD45RO(−), CCR7(+), CD45RA(+), CD62L(+), CD27(+), CD28(+) and/or IL-7Ra(+). Suitable cells also include stem cells such as, for example, embryonic stem cells, induced pluripotent stem cells, hematopoietic stem cells, neuronal stem cells, and mesenchymal stem cells. Suitable cells can comprise any number of primary cells, such as human cells, non-human cells, and/or mouse cells. Suitable cells can be progenitor cells. Suitable cells can be derived from a subject (e.g., a patient) to be treated.

The therapeutically effective amount of cells required in a patient can vary depending on the viability of the cells and the efficiency with which the cells are genetically modified (e.g., the efficiency with which the transgene is integrated into one or more cells, or the expression level of the protein encoded by the transgene). In some embodiments, the product (e.g., doubling) of the cell viability after genetic modification and the efficiency of transgene integration may correspond to a therapeutic amount of cells which can be used for administration to a subject. In some embodiments, an increase in cell viability after genetic modification may correspond to a reduction in the essential amount of cells effective for being administered to a patient. In some embodiments, an increase in the efficiency of integration of a transgene into one or more cells can correspond to a reduction in the number of cells necessary administered in a patient for effective treatment. In some embodiments, determination of the amount of cells necessary for effective treatment can include determination of functions associated with changes in cells over time. In some embodiments, determination of the amount of cells necessary for effective treatment can include determination of functions corresponding to changes in efficiency of integrating a transgene into one or more cells according to a time-dependent variable (e.g., cell culture time, electroporation time, Cell stimulation time). In some embodiments, therapeutically effective cells can be a population of cells comprising about 30% to about 100% of the expression of an antigen-binding receptor on the surface of the cell. In some embodiments, the therapeutically effective cells, as measured by flow cytometry, can express about 30%, 35%, 40%, 45%, 50%, 55%, 60%, 65%, 70%, 75% 80%, 85%, 90%, 91%, 92%, 93%, 94%, 95%, 96%, 97%, 98%, 99%, 99.5%, 99.9% or more than about 99.9% of the antigen-binding receptor on the cell surface.

According to one aspect of the invention, the invention also encompasses a nucleic acid encoding the antigen-binding receptor. The invention also relates to variants of the above polynucleotides which encode a polypeptide or a fragment, analog and derivative of the polypeptide having the same amino acid sequence as the invention.

The present invention also provides a vector comprising the above nucleic acid encoding the antigen-binding receptor protein expressed on the surface of an immune response cell.

The invention also includes viruses comprising the vectors described above. The virus of the present invention includes an infectious virus after packaging, and also includes a virus to be packaged to contain components necessary for being packaged into an infectious virus. Other viruses known in the art that can be used to transduce exogenous genes into immune response cells and their corresponding plasmid vectors can also be used in the present invention.

In another aspect, a host cell is provided herein, comprising an antigen binding unit or chimeric antigen receptor as described herein, and optionally type I interferon. In another aspect, a host cell is provided herein, comprising a nucleic acid encoding an antigen binding unit or chimeric antigen receptor described herein, and optionally type I interferon.

In some embodiments, the host cell is an immune response cell. In some embodiments, the immune response cell is a T cell, a natural killer cell, a cytotoxic T lymphocyte, a natural killer T cell, a DNT cell and/or a regulatory T cell. In some embodiments, the host cell is an NK92 cell.

In some embodiments, an expression construct can be included in an immune response cell of the invention, and elements are sequentially linked in the following manner: antibody, CD28 costimulatory signal domain, CD3ζ, as well as NFAT6 and type I interferon expression unit inversely linked with the aforementioned elements. Preferably, the antibody and CD28 costimulatory signal domain are joined by a CD8α transmembrane region and a CD8α hinge region.

In some embodiments, NFAT (nuclear factor of activated T cells) plays an important role in the transcriptional expression of cytokines during T cell activation. Based on this consideration, the inventors placed the IFN-beta encoding sequence under the regulation of NFAT6 promoter, so that IFN-beta can be expressed at a high level only when CAR-T cells contact the antigen to induce T cell activation.

NFAT6 promoter is a promoter obtained by combining six NFAT binding positions and a minimal promoter of IL2 (Hooijberg E, Bakker A Q, Ruizendaal J J, Spits H. NFAT-controlled expression of GFP permits visualization and Isolation of antigen-stimulated primary human Tcells. Blood. 2000 Jul. 15; 96(2): 459-66), which can be used to regulate the expression of cytokines such as IL12 in T lymphocytes such as TCR-T (Zhang L, Kerkar S P, Yu Z, Zheng Z, Yang S, Restifo N P, Rosenberg S A, Morgan R A. Improving adoptive T cell therapy by targeting and controlling IL-12 expression to the tumor environment. Mol Ther. 2011 April; 19(4):751-9).

The immune response cell of the present invention is transduced with a construct capable of expressing an antigen-binding receptor and an exogenous type I interferon, or an expression vector or a virus comprising the plasmid. Conventional nucleic acid transduction methods in the art, including non-viral and viral transduction methods, can be used in the present invention.

The immune response cell of the present invention may further carry an encoding sequence of an exogenous cytokine, including, but not limited to, IL-12, IL-15 or IL-21 and the like. These cytokines have further immunomodulatory or anti-tumor activity, enhance the function of effector T cells and activated NK cells, or directly exert anti-tumor effects. Thus, a skilled person will appreciate that using these cytokines will help the immune response cells to function better.

The immune response cell of the present invention may also express another antigen-binding receptor other than the antigen-binding receptor described above.

The immune response cells of the invention may also express a chemokine receptor; and the chemokine receptors include, but are not limited to, CCR2. A skilled person will appreciate that CCR2 chemokine receptor can compete with CCR2 binding in vivo, which is advantageous for blocking tumor metastasis.

The immune response cells of the present invention can also express siRNA which can reduce PD-1 expression or a protein which can block PD-L1. A skilled person will appreciate that competitively blocking the interaction of PD-L1 with its receptor PD-1 facilitates the recovery of anti-tumor T cell responses, thereby inhibiting tumor growth.

The immune response cells of the present invention may also express a safety switch; and preferably, the safety switch includes: iCaspase-9, Truncated EGFR or RQR8.

In some embodiments, the immune response cells of the invention do not express a costimulatory ligand, such as 4-1BBL.

Accordingly, in another aspect, a method for producing an antigen binding unit or chimeric antigen receptor described herein, or a composition comprising the same is provided herein, comprising culturing a host cell described herein under suitable conditions. In some embodiments, the method includes isolating and obtaining an expression product of the host cell.

In another aspect, a composition is provided herein comprising an antigen binding unit, chimeric antigen receptor or nucleic acid described herein. In some embodiments, the composition is a pharmaceutical composition comprising the antigen binding unit, chimeric antigen receptor or nucleic acid. In some embodiments, the pharmaceutical composition further comprises a pharmaceutically acceptable carrier.

In another aspect, a pharmaceutical composition is provided herein, comprising a host cell described herein and a pharmaceutically acceptable carrier.

The term "pharmaceutically acceptable" means that when a molecular and composition are suitably administered to an animal or a human, they do not produce adverse, allergic or other untoward reactions.

In some embodiments, the composition comprises an additional therapeutic agent. In some embodiments, the additional therapeutic agent is a chemotherapeutic agent, such as those described in US20140271820 and/or a pharmaceutically acceptable salt or analog thereof. In some embodiments, the therapeutic agent includes, but is not limited to, a mitotic inhibitor (vinca alkaloid), including vincristine, vinblastine, vindesine, and Novibin™ (vinorelbine, 5'-dehydrohydrogen sulfide); topoisomerase I inhibitors, such as camptothecin compounds, including Camptosar™ (irinotecan HCL), Hycamtin™ (topotecan HCL), and other compounds derived from camptothecin and the like; a podophyllotoxin derivative such as etoposide, teniposide and midozozo; an alkylating agent cisplatin, cyclophosphamide, nitrogen mustard, trimethylene thiophosphoramide, carmustine, busulfan, chlorambucil, briquetazine, uracil mustard, cloprofen and dacarbazine; antimetabolites, including cytarabine, 5-fluorouracil, methotrexate, guanidine, azathioprine and procarbazine; antibiotics, including but not limited to doxorubicin, bleomycin, dactinomycin, daunorubicin, mycinmycin, mitomycin, sarcoma C and daunorubicin; as well as other chemotherapeutic drugs, including but not limited to anti-tumor antibodies, dacarbazine, cytidine, amushakang, melphalan, ifosfamide and mitoxantrone. In some embodiments, the additional therapeutic agent is selected from one or more of epirubicin, oxaliplatin and 5-fluorouracil. In some embodiments, the additional therapeutic agent includes, but is not limited to, an anti-angiogenic agent, including anti-VEGF antibodies (including humanized and chimeric antibodies, anti-VEGF aptamers and antisense oligonucleotides), and other angiogenesis inhibitor such as angiostatin, endostatin, interferon, interleukin 1 (including α and β), interleukin 12, retinoic acid and tissue inhibitors of metalloproteinases-1 and -2, and the like.

Specific examples of some substances which can be used as pharmaceutically acceptable carriers or components thereof are sugars such as lactose, glucose and sucrose; starches such as corn starch and potato starch; cellulose and derivatives thereof such as carboxymethyl cellulose sodium, ethyl cellulose and methyl cellulose; tragacanth gum powder; malt; gelatin; talc; solid lubricants, such as stearic acid and magnesium stearate; calcium sulfate; vegetable oils, such as peanut oil, cottonseed oil, sesame oil, olive oil, corn oil and cocoa butter; polyols such as propylene glycol, glycerin, sorbitol, mannitol and polyethylene glycol; alginic acid; emulsifiers such as Tween®; wetting agents such as sodium lauryl sulfate Colorant; flavoring agent; compressed tablets, stabilizers; antioxidants; preservatives; pyrogen-free water; isotonic saline solution; and phosphate buffer.

The pharmaceutical composition described herein may comprise one or more pharmaceutically acceptable salts. "Pharmaceutically acceptable salt" refers to a salt that retains the desired biological activities of the parent compound and does not produce any adverse toxicological effects (see, for example, Berge, S. M., et al., 1977, J. Pharm. Sci. 66: 1-19). Examples of such salts include acid addition salts and base addition salts.

Acid addition salts include salts derived from non-toxic inorganic acids, such as hydrochloric acid, nitric acid, phosphoric acid, sulfuric acid, hydrobromic acid, hydroiodic acid, phosphorous acid, and the like, and derived from non-toxic organic acids such as aliphatic monocarboxylic acids and dicarboxylic acid, a phenyl-substituted alkanoic acid, a hydroxyalkanoic acid, an aromatic acid, an aliphatic or an aromatic sulfonic acid. Base addition salts include salts derived from alkaline earth metals (such as sodium, potassium, magnesium, calcium, etc.), as well as salts derived from non-toxic organic amines, such as N,N'-dibenzylethylenediamine, N-methylglucosamine, glucosamine, chloroprocaine, choline, diethanolamine, ethylenediamine, procaine and the like.

The pharmaceutical composition described herein may also comprise an antioxidant. Examples of antioxidants include, but are not limited to, water-soluble antioxidants such as ascorbic acid, cysteine hydrochloride, sodium hydrogen sulfate, sodium metabisulfite, sodium sulfite, etc.; oil-soluble antioxidants such as ascorbyl palmitate, butylated hydroxyanisole (BHA), butylated hydroxytoluene (BHT), lecithin, propyl gallate, alpha-tocopherol, etc.; and metal chelating agents such as citric acid, ethylenediaminetetraacetic acid (EDTA), sorbitol, tartaric acid, phosphoric acid, etc.

The composition of the present invention can be formulated into various dosage forms as needed, and can be administered by a physician in accordance with factors such as patient type, age, body weight, general disease condition and mode of administration, and the like in a beneficial dose to a patient. The mode of administration can be, for example, parenteral administration (e.g., injection) or other treatment.

"Parenteral" administration of an immunogenic composition includes, for example, subcutaneous (s.c.), intravenous (i.v.), intramuscular (i.m.) or intrasternal injection or infusion techniques.

Formulations comprising an immunoreactive cell population administered to an individual comprise a plurality of immunoreactive cells effective to treat and/or prevent a particular indication or disease. Therefore, a therapeutically effective population of immunoreactive cells can be administered to an individual. Typically, a formulation comprising from about $1 \times 10^4$ to about $1 \times 10^{10}$ immunoreactive cells is administered. In most cases, the formulation will comprise from about $1 \times 10^5$ to about $1 \times 10^9$ immunoreactive cells, from about $5 \times 10^5$ to about $5 \times 10^8$ immunoreactive cells, or from about $1 \times 10^6$ to about $1 \times 10^7$ immunoreactive cells. However, depending on the location, source, identity, extent and severity of a cancer, the age and physical condition of an individual to be treated, and the like, the number of CAR immunoreactive cells administered to the individual will vary within a wide range. The doctor will finalize an appropriate dose to be used.

In some embodiments, a chimeric antigen receptor is used to stimulate an immune cell mediated immune response. For example, a T cell mediated immune response is an immune response involving T cell activation. Activated antigen-specific cytotoxic T cells are capable of inducing apoptosis in target cells that exhibit an exogenous epitope on the surface, such as cancer cells that display tumor antigens. In other embodiments, a chimeric antigen receptor is used to provide anti-tumor immunity in a mammal. Subjects will develop anti-tumor immunity due to T cell-mediated immune responses.

In certain instances, a method for treating a subject having cancer can involve administering one or more immune response cells of the invention to a subject in need of treatment. The immune response cell can bind to a target molecule of a tumor and induce death of cancer cells. As also mentioned above, the invention also provides a method for treating pathogen infections in an individual, comprising administering to an individual a therapeutically effective amount of immune response cells of the invention.

The administration frequency of the immunoreactive cells of the present invention will depend on factors including the treated disease, the elements of the particular immunoreactive cells, and the mode of administration. For example, it can be administered 4 times, 3 times, 2 times a day, once a day, every other day, every three days, every four days, every five days, every six days, once a week, once every eight days, once every nine days, once every ten days, once a week, or twice a month. As described herein, the immune response cells of the present application can be administered not only in a therapeutically effective amount which is lower than that of a similar immune response cell without expressing exogenous type I interferon, but also can be administered at a lower frequency to achieve at least similar, and preferably more pronounced therapeutic effects, since the immune response cells of the present application have improved viability.

In some embodiments, the compositions may be isotonic, i.e., they may have the same osmotic pressure as blood and tears. The desired isotonicity of the compositions of the present invention can be achieved using sodium chloride or other pharmaceutically acceptable agents such as glucose, boric acid, sodium tartrate, propylene glycol or other inorganic or organic solutes. If desired, the viscosity of the composition can be maintained at a selected level using a pharmaceutically acceptable thickening agent. Suitable thickeners include, for example, methylcellulose, xanthan gum, carboxymethylcellulose, hydroxypropylcellulose, carbomer, and the like. The preferred concentration of thickener will depend on the reagent selected. It will be apparent that the choice of suitable carrier and other additives will depend on the exact route of administration and properties of the particular dosage form, such as a liquid dosage form.

The invention also provides kits comprising an antigen binding unit, chimeric antigen receptor, nucleic acid or immune response cell as described herein. In some embodiments, a kit can include a therapeutic or prophylactic composition comprising an effective amount of an antigen binding unit, chimeric antigen receptor, nucleic acid, or immune response cell described herein in one or more unit dosage forms. In some embodiments, the kit comprises a sterile container that can contain a therapeutic or prophylactic composition; and such a container can be a cartridge, ampule, bottle, vial, tube, bag, blister pack, or other suitable container form known in the art. Such containers may be made of plastic, glass, laminated paper, metal foil or other materials suitable for holding the drug. In some embodiments, the kit comprises an antigen binding unit, chimeric antigen receptor, nucleic acid or immune response cell as described herein, and an instruction for administering the antigen binding unit, chimeric antigen receptor, nucleic acid or immune response cell described herein to an individual. The instruction generally include methods for treating or preventing cancer or tumors using the antigen binding units, chimeric antigen receptors, nucleic acids or immune response cells described herein. In some embodiments, the kit comprises host cells as described herein and can comprise from about $1\times10^4$ cells to about $1\times10^6$ cells. In some embodiments, the kit can comprise at least about $1\times10^5$ cells, at least about $1\times10^6$ cells, at least about $1\times10^7$ cells, at least about $4\times10^7$ cells, at least about $5\times10^7$ cells, at least about $6\times10^7$ cells, at least about $6\times10^7$ cells, $8\times10^7$ cells, at least about $9\times10^7$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least at least about $9\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about $5\times10^{11}$ cells, at least about $8\times10^{11}$ cells, at least about $9\times10^{11}$ cells or at least about $1\times10^{12}$ cells. For example, approximately $5\times10^{10}$ cells can be included in the kit. In another example, the kit can include $3\times10^6$ cells; and the cells can be expanded to about $5\times10^{10}$ cells and administered to a subject.

In some embodiments, the kit can include allogeneic cells. In some embodiments, the kit can include cells that can contain genomic modifications. In some embodiments, the kit can comprise "ready-made" cells. In some embodiments, the kit can include cells that can be expanded for clinical use. In some cases, the kit may contain content for research purposes.

In some embodiments, the instruction includes at least one of: a description of a therapeutic agent; a dosage regimen and administration for treating or preventing a tumor or a symptom thereof; preventive measures, warnings, contraindications, excessive information, adverse reactions, animal pharmacology, clinical research, and/or citations. The instruction can be printed directly on the container (if any), or as a label on the container, or as a separate paper, booklet, card or folder in the container. In some embodiments, the instruction provides a method for administering an immune response cell of the invention for treating or preventing a tumor. In some cases, the instruction provides a method for administering an immunoreactive cell of the invention before, after or simultaneously with the administration of a chemotherapeutic agent.

In another aspect, a method for inducing death of a cell comprising claudin 18A2 peptide is provided herein, the method comprising: contacting the cell with an antigen binding unit described herein, a chimeric antigen receptor described herein, a compositions described herein, or a host cell described herein. In some embodiments, the contacting is in vitro contacting. In some embodiments, the contacting is in vivo contacting.

In some embodiments, the cell is a tumor cell. In some embodiments, the cell is a cell of solid tumor. In some embodiments, the cell is a cell of a cancer or a tumor as described herein. Particular examples of such cells may include, but are not limited to, leukemia (e.g., acute leukemia, acute lymphocytic leukemia, acute myeloid leukemia, acute myeloid leukemia, acute promyelocytic leukemia, acute granulocyte-monocytic leukemia, acute monocytic leukemia, acute leukemia, chronic leukemia, chronic myeloid leukemia, chronic lymphocytic leukemia, polycythemia vera) cells, lymphoma (Hodgkin's disease, non-Hodgkin's disease) cells, primary macroglobulinemia disease cells, heavy chain disease cells, solid tumors such as sarcoma and cancer cells (such as fibrosarcoma, mucinous sarcoma, liposarcoma, chondrosarcoma, osteosarcoma, chordoma, endothelial sarcoma, lymphangiosarcoma, angiosarcoma, lymphatic endothelial sarcoma, synovial vioma, mesothelioma, Ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, sweat gland cancer, sebaceous gland cancer, papillary carcinoma, papillary adenocarcinoma, cancer, bronchial carcinoma, medullary carcinoma, renal cell carcinoma, liver cancer, bile Tube cancer, choriocarcinoma, seminoma, embryonic carcinoma, nephroblastoma, cervical cancer, uterine cancer, testicular cancer, lung cancer, small cell lung cancer, bladder cancer, epithelial cancer, glioma, astrocytoma, medulla Blastoma, craniopharyngioma, ependymoma, pineal tumor, hemangioblastoma, acoustic neuroma, oligodendroglioma, schwannomas, meningioma, melanoma, neuroblastoma, retinoblastoma), esophageal cancer cells, gallbladder cancer cells, renal cancer cells, multiple myeloma cells, and the like. In some embodiments, the cell is a gastric cancer cell, an esophageal cancer cell, an intestinal cancer cell, a pancreatic cancer cell, a nephroblastoma cell, a lung cancer cell, an ovarian cancer cell, a colon cancer cell, a rectal cancer cell, a liver cancer cell, a head and neck cancer cells, a chronic myeloid leukemia cell and a gallbladder cancer cell.

In another aspect, a method for treating a tumor in an individual in need thereof is provided herein, the method comprising administering to the individual an effective amount of an antigen binding unit, chimeric antigen receptor, composition, vector or host cell described herein.

In some embodiments, the tumor includes, but is not limited to, a tumor of bladder, bone, brain, breast, cartilage, glial cells, esophagus, fallopian tubes, gallbladder, heart, intestine, kidney, liver, lung, lymph nodes, nervous tissue, ovary, pancreas, prostate, skeletal muscle, skin, spinal cord, spleen, stomach, testis, thymus, thyroid, trachea, urethra, ureter, urethra, uterus, vaginal organs. In some embodiments, the tumor includes, but is not limited to, leukemia (e.g., acute leukemia, acute lymphocytic leukemia, acute myeloid leukemia, acute myeloid leukemia, acute promyelocytic leukemia, acute granulocyte-monocytic leukemia, acute monocytic leukemia, acute leukemia, chronic leukemia, chronic myeloid leukemia, chronic lymphocytic leukemia, polycythemia vera), lymphoma (Hodgkin's disease, non-Hodgkin's disease), primary macroglobulinemia disease, heavy chain disease, solid tumors such as sarcoma and cancer (such as fibrosarcoma, mucinous sarcoma, liposarcoma, chondrosarcoma, osteosarcoma, chordoma, endothelial sarcoma, lymphangiosarcoma, angiosarcoma, lymphatic endothelial sarcoma, synovial vioma, mesothelioma, Ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, sweat gland cancer, sebaceous gland cancer, papillary cancer, papillary adenocarcinoma, cancer, bronchial carcinoma, medullary carcinoma, renal cell carcinoma, liver cancer, bile tube cancer, choriocarcinoma, seminoma, embryonic carcinoma, nephroblastoma, cervical cancer, uterine cancer, testicular cancer, lung cancer, small cell lung cancer, bladder cancer, epithelial cancer, glioma, astrocytoma, medulloblastoma, craniopharyngioma, ependymoma, pineal tumor, hemangioblastoma, acoustic neuroma, oligodendroglioma, schwannomas, meningiomas, melanoma, neuroblastoma, retinoblastoma), esophageal cancer, gallbladder cancer, kidney cancer, multiple myeloma. In some embodiments, the tumor is gastric cancer, esophageal cancer, intestinal cancer, pancreatic cancer, nephroblastoma, lung cancer, ovarian cancer, colon cancer, rectal cancer, liver cancer, head and neck cancer, chronic myelogenous leukemia, or gallbladder cancer.

In some embodiments, immunoreactive cells can be administered to a subject, wherein the immunoreactive cells that can be administered can be from about 1 to about 35 days of age. For example, the administered cells may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or up to about 40 days of age. The age of CAR immunoreactive cells can be calculated from the time of stimulation. The age of the immunoreactive cells can be calculated from the time of blood collection. The age of immunoreactive cells can be calculated from the time of transduction. In some embodiments, the immunoreactive cells that can be administered to a subject are from about 10 to about 14 or about 20 days of age. In some embodiments, the "age" of an immunoreactive cell can be determined by the telomere length. For example, a "young" immune response cell can have a longer telomere length than that of "depleted" or "old" immunoreactive cells. Without being bound by a particular theory, it is believed that immunoreactive cells lose an estimated telomere length of about 0.8 kb per week in culture, and a young immunoreactive cell culture can have a longer telomere than an immunoreactive cell of about 44 days about 1.4 kb. Without being bound by a particular theory, it is believed that a longer telomere length can be associated with a positive objective clinical response in a patient and persistence of cells in vivo.

Cells (e.g., engineered cells or engineered primary T cells) can be functional before, after and/or during transplantation. For example, the transplanted cells may function at least about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 40, 50, 60, 70, 80, 90 or 100 days after transplantation. The transplanted cells can function at least about 1, 2, 3, 4, 5, 6, 7, 8, 9, 10, 11 or 12 months after transplantation. The transplanted cells can function at least about 1, 2, 3, 4, 5, 6, 7, 8, 9, 10, 15, 20, 25 or 30 years after transplantation. In some embodiments, the transplanted cells can function during the life of the recipient.

In addition, the transplanted cells can function at 100% of normally expected function. The transplanted cells can also exert about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or up to about 100% of their normally expected function.

Transplanted cells can also exert more than 100% of their normally expected function. For example, the transplanted cells can exert about 110, 120, 130, 140, 150, 160, 170, 180, 190, 200, 250, 300, 400, 500, 600, 700, 800, 900, 1000 or up to about 5000% of their normally expected function.

Transplant can be any type of transplant. Local position may include, but is not limited to, subhepatic sac space, subsplenic sac space, subcapsular space, omentum, gastric or intestinal submucosa, small intestinal vascular segment, venous sac, testis, brain, spleen, or cornea. For example, the transplant can be a subcapsular transplant. The transplant can also be an intramuscular transplant. The transplant can be a portal vein transplant.

The transplant rejection can be improved after treatment with the immune response cells of the present invention as compared with the situation when one or more wild type cells are transplanted to a recipient. For example, transplant rejection can be a hyperacute rejection. Transplant rejection can also be an acute rejection. Other types of rejection may include chronic rejection. Transplant rejection can also be cell-mediated rejection or T cell-mediated rejection. Transplant rejection can also be a natural killer cell mediated rejection.

Improvement in transplantation may refer to alleviation of hyperacute rejection, which may include reduction, alleviation or lowering of adverse effects or symptoms. Transplantation can refer to adoptive transplantation of cellular products.

Another sign of successful transplantation may be the number of days for which the recipient does not need immunosuppressive therapy. For example, after providing the immune response cells of the invention, the recipient may not require at least about 1, 2, 3, 4, 5, 6, 7, 8, 9, 10 or more days of immunosuppressive therapy. This can indicate successful transplantation. This can also indicate that the transplanted cells, tissues and/or organs are not rejected.

In some cases, the recipient does not require immunosuppressive therapy for at least 1 day. The recipient may not require immunosuppressive therapy for at least 7 days. The recipient does not require immunosuppressive therapy for at least 14 days. The recipient does not require immunosuppressive therapy for at least 21 days. The recipient does not require immunosuppressive therapy for at least 28 days. The recipient does not require immunosuppressive therapy for at least 60 days. In addition, the recipient may not require immunosuppressive therapy for at least 1, 2, 3, 4, 5, 6, 7, 8, 9, 10 or more years.

Another sign of successful transplants may be the reduced number of days for which a recipient needs an immunosuppressive therapy. For example, after the treatment provided herein, the recipient may require a reduced immunosuppressive therapy for at least 1, 2, 3, 4, 5, 6, 7, 8, 9, 10 or more days. This can indicate successful transplantation. This may also indicate that there are no or only minimal rejection of the transplanted cells, tissues and/or organs.

For example, a recipient may require a reduced immunosuppressive therapy for at least 1 day. The recipient may also require a reduced immunosuppressive therapy for at least 7 days. The recipient may require a reduced immunosuppressive therapy for at least 14 days. The recipient requires a reduced immunosuppressive therapy for at least 21 days. The recipient requires a reduced immunosuppressive therapy for at least 28 days. The recipient requires a reduced immunosuppressive therapy for at least 60 days. In addition, the recipient may require a reduced immunosuppressive therapy for at least 1, 2, 3, 4, 5, 6, 7, 8, 9, 10 or more years.

A reduced immunosuppressive therapy can refer to less requirement on immunosuppressive therapy as compared with the situation when one or more wild type cells are transplanted to a recipient.

Immunosuppressive therapy can include any treatment that inhibits the immune system. Immunosuppressive therapy can facilitate alleviation, reduction or elimination of transplant rejection in patients. For example, immunosuppressants can be used before, during, and/or after transplantation, including MMF (Mycophenolate mofetil, Cellcept), ATG (anti-thymocyte globulin), anti-CD154 (CD40L), anti-CD40 (2C10), immunosuppressive drugs, anti-IL-6R antibodies (tocilizumab, Actemra), anti-IL-6 antibodies (sarilumab, olokizumab), CTLA4-Ig (Abatacept/Orencia), anti-IL-6 antibodies (ASKP1240, CCFZ533X2201)), amphetamine (Campath), anti-CD20 (rituximab), bevacizumab (LEA29Y), sirolimus (Rapimune), everolimus, tacrolimus (Prograf), Zemegab, Zemilect, Remicade, cyclosporin, deoxygenin, soluble complement receptor 1, cobra venom, anti-CS antibody Eculizumab/Soliris), methylprednisolone, FTY720, everolimus, leflunomide, anti-IL-2R-Ab, rapamycin, anti-CXCR3 antibody, anti-ICOS antibody, anti-OX40 antibody and anti-CD122 antibody. In addition, one or more immunosuppressive agents/drugs may be used together or sequentially. One or more immunosuppressive agents/drugs can be used to induce therapy or to maintain therapy. Same or different drugs can be used in the induction and maintenance phases. In some cases, daclizumab (Zenapax) can be used for induction therapy, and Tacrolimus (Prograf) and Sirolimus (Rapimune) can be used to maintain treatment. Non-pharmacological regimens can also be used to achieve immunosuppression, including but not limited to whole body irradiation, thymic irradiation, and total and/or partial splenectomy. These techniques can also be used in combination with one or more immunosuppressive drugs.

In some embodiments, an antigen binding unit, chimeric antigen receptor, composition, vector or host cell described herein can be administered in combination with another therapeutic agent. In some embodiments, the additional therapeutic agent is a chemotherapeutic agent, such as those described in US20140271820. Chemotherapeutic agents that can be used in combination with the immune response cells of the invention include, but are not limited to, mitotic inhibitors (vinca alkaloids), including vincristine, vinblastine, vindesine, and Novibin™ (vinorelbine), 5'-dehydrohydrogen sulfide); topoisomerase I inhibitors, such as camptothecin compounds, including Camptosar™ (Irinotecan HCL), Hycamtin™ (topotecan HCL), and other compounds derived from camptothecin and analogs thereof; podophyllotoxin derivatives such as etoposide, teniposide and midozozo; alkylating agents cisplatin, cyclophosphamide, nitrogen mustard, trimethylene thiophosphoramide, nitrogen mustard, busulfan, chlorambucil, briquetazine, uracil mustard, cloprofen and dacarbazine; antimetabolites, including cytarabine, 5-fluorouracil, methotrexate, anthraquinone, azathioprine and procarbazine; antibiotics including, but not limited to, doxorubicin, bleomycin, dactinomycin, daunorubicin, mycinmycin, mitomycin, sarcoma C and daunorubicin; and other chemotherapeutic drugs, including but not limited to anti-tumor antibodies, dacarbazine, cytidine, amushakang, melphalan, ifosfamide and mitoxantrone. In some embodiments, the additional therapeutic agent is selected from one or more of epirubicin, oxaliplatin and 5-fluorouracil.

In some embodiments, chemotherapeutic agents that can be used in combination with the immune response cells of the invention include, but are not limited to, an anti-angiogenic agent, including anti-VEGF antibodies (including humanized and chimeric antibodies, anti-VEGF aptamers and antisense oligonucleotides), and other angiogenesis inhibitor such as angiostatin, endostatin, interferon, interleukin 1 (including α and β), interleukin 12, retinoic acid and tissue inhibitors of metalloproteinases-1 and -2, and the like.

Examples

The invention is further illustrated below in conjunction with specific embodiments. It is to be understood that the examples are intended to demonstrate the invention while not intended to limit the scope of the invention. The experimental methods in the following examples, specific conditions of which are not specified are usually prepared according to conventional conditions such as conditions described in J. Sambrook et al., Molecular Cloning Experimental Guide, Third Edition, Science Press, 2002, or according to the conditions suggested by the manufacturer.

In the following examples of the invention, when the antigen-binding receptor or CAR is constructed, CD28 costimulatory signal domain is abbreviated as 28; CD3ζ is abbreviated as Z; 4-1BB or CD137 is abbreviated as BB. For example, a chimeric antigen receptor constructed by a scFv with a code of 8E5-2I and CD3ζ as well as CD28 costimulatory signal domains as an intracellular signal domain can be referred to as 8E5-2I-28Z. CARs for different antigens are constructed as such.

Example 1. Production and Characterization of Mouse Antibody Against CLD18A2

Antibody fragments were obtained using standard biological protocols. Briefly, 8-week old Balb/c mice were immunized with a eukaryotic expression vector containing human CLD18A2 full-length sequence (NCBI Reference Sequence: NM_001002026.2). The spleen of the immunized mouse was removed, and a monoclonal antibody was obtained using a conventional biological scheme in the art.

Individual cells were screened for anti-CLD18A2 monoclonal antibody by flow cytometry, and HEK293 cells (HEK-CLD18A2) stably expressing human CLD18A2 were used for primary screening by flow cytometry using a Guava easyCyte™ HT System instrument. The binding of the antibody to human CLD18A1 and CLD18A2 transformants was then compared by flow cytometry. The instrument used was the Guava easyCyte™ HT System.

After multiple rounds of preparation and screening of hybridomas, the inventors found several antibodies with relatively ideal binding properties. FIG. 1B shows an example of the binding of hybridoma supernatants 2B1, 3E12, 4A11, 8E5 to HEK293 cells stably transfected with human CLD18A2 or CLD18A1 as determined by flow cytometry. As shown in FIG. 1B, after two rounds of subcloning, most of subclones of antibodies 2B1, 3E12, 4A11 and 8E5 specifically bound to human CLD18A2 but not human CLD18A1, and the average fluorescence intensities differed by more than 5 times.

The monoclonal antibody-secreting hybridoma cell strain was cultured, and total RNA was extracted from the cell pellet according to instructions of TRIzol® Plus RNA Purification kit (Invitrogen, 12183-555). The cDNA was reverse-transcribed using total RNA as template according to the instructions of High capacity RNA to cDNA kit (Invitrogen, 4387406). The cDNA was used as a template, and 5'-Full RACE kit (TAKARA, D315) and primers of the constant region of the antibody were used for amplification. PCR products were separated on 1.5% agarose gel, and the DNA fragments were purified and recovered. The sequencing results were as follows:

TABLE 5

Sequencing results

| | Amino acid sequence | Nucleotide sequence |
|---|---|---|
| 2B1 VL | SEQ ID NO: 1 | SEQ ID NO: 2 |
| 2B1 VH | SEQ ID NO: 3 | SEQ ID NO: 4 |
| 3E12 VL | SEQ ID NO: 5 | SEQ ID NO: 6 |
| 3E12 VH | SEQ ID NO: 7 | SEQ ID NO: 8 |
| 4A11 VH | SEQ ID NO: 9 | SEQ ID NO: 10 |
| 4A11 VL | SEQ ID NO: 11 | SEQ ID NO: 12 |
| 8E5 VL | SEQ ID NO: 13 | SEQ ID NO: 14 |
| 8E5 VH | SEQ ID NO: 15 | SEQ ID NO: 16 |

The antibody sequences were aligned and the results are shown in FIG. 2.

Example 2. Construction of Anti-Claudin 18A2 scFv_Fc Fusion Antibody and its Transient Expression in Eukaryotic Cells For VH and VL fragments of 2B1, 8E5, a flexible amino acid GGGGSGGGGSGGGGS (SEQ ID NO:93) was introduced as a linker to constitute scFv; an appropriate restriction site and protective bases were introduced upstream to VH, and an appropriate restriction site and protective bases were introduced downstream to VL; and digested and ligated into an eukaryotic expression vector (see vector pH or vector pK used in CN101602808). 293Fectin™ Transfection reagent (Invitrogen, 12347-019) was used in transient transfection, the supernatant was collected and subjected to affinity purification, and the obtained antibody was quantitatively and qualitatively analyzed by SDS PAGE.

Binding of anti-Claudin 18A2 scFv_Fc fusion antibody to HEK293 cells stably transfected with CLD18A2 was determined by flow cytometry. Experimental data was analyzed using GraphPad Prism and Guava easyCyte™ HT System instrument as described in Example 1 to obtain EC50 value. FIG. 3 shows the relative binding affinity of scFvs of monoclonal antibody 2B1, 8E5, after fused to human IgG1 Fc portion, to HEK293 cells stably transfected with human CLD18A2. It can be seen that the EC50 value of 2B1 is 3.56 nM, and the EC50 value of 8E5 is 49.19 nM.

Example 3. Preparation of Variants of Anti-Claudin 18A2 Antibodies

Antibody 2B1 was subject to site-directed mutagenesis by bridge PCR. Mutations were introduced at position 52 or 54 (N-glycosylation site) on the heavy chain of antibody 2B1 for preparing two 2B1 mutants 2B1-N52D (VH amino acid sequence: SEQ ID NO:17; nucleotide sequence: SEQ ID NO:18) and 2B1-S54A (VH amino acid sequence: SEQ ID NO:19; nucleotide sequence: SEQ ID NO:20).

The amino acid sequences and nucleotide sequences of the light chains of 2B1-N52D and 2B1-S54A are identical to the corresponding sequences of 2B1.

Expression vectors of ScFv Fc-form of the two mutants were constructed as described in Example 2, and according to the procedure of Example 2, and the experimental data was analyzed using GraphPad Prism and Guava easyCyte™ HT System instrument to obtain EC50.

FIG. 4 shows the relative binding affinity of 2B1-N52D and 2B1-S54A, after fused to human IgG1 Fc portion, to HEK293 cells stably transfected with human CLD18A2. It can be seen that the EC50 value of 2B1-N52D is 6.11 nM, and the EC50 value of 2B1-S54A is 3.85 nM.

Example 4. Preparation of Humanized Antibody of 2B1-S54A

Sequences of 6 CDRs of the antibody light and heavy chain were determined according to Kabat, Chothia and IMGT Naming schemes. By using sequence similarity alignment, the antibody sequence with the highest similarity to 2B1-S54A was selected as the antibody template. In this example, IGHV1-46*01 in IMGT database was selected as an antibody template for hu2B1-S54A heavy chain. IGKV4-1*01 was used as an antibody template for hu2B1-S54A light chain. The light and heavy chain CDR regions of 2B1-S54A were replaced with CDR regions of the antibody template.

Determination of reverse mutation sites: (1) Aligning a designed humanized antibody with the starting antibody, and checking which amino acids in the antibody framework region are different. (2) Checking whether these different amino acids are amino acids that support the loop structure of the antibody or amino acids that affect the binding of variable regions of the light and heavy chains, and if yes, these regions are relatively conserved regions. (3) Checking whether there are some potential post-translational modification sites in humanized antibodies, such as deamidation sites (Asn-Gly), isomerization sites (Asp-Gly), surface-exposed methionine, N glycosylation site (Asn-X-Ser/Thr, X is not proline). (4) There are six potential reverse mutation sites in the heavy chain of humanized antibody (hu2B1-S54A), namely M48I, V68A, M70L, R72A, T74K, T91S, respectively. There is a potential reverse mutation site in the light chain of humanized antibody (hu2B1-S54A), L84V.

Expression and purification of humanized antibodies: (1) A nucleotide sequence was designed and synthesized based on the amino acid sequence of humanized antibody (hu2B1-S54A). A light chain nucleotide sequence (SEQ ID NO:62) was synthesized; and a heavy chain nucleotide sequence (SEQ ID NO:60) was synthesized. (2) The synthetic antibody nucleotide sequence including the signal peptide, variable region of the antibody and constant region is inserted into a mammalian cell expression vector to construct antibody expression vectors containing the heavy chain and the light chain, respectively, sequenced and identified.

The heavy chain amino acid sequence of hu2B1-S54A is set forth in SEQ ID NO:59; and the nucleotide sequence is set forth in SEQ ID NO:60. The amino acid sequence of hu2B1-S54A light chain is set forth in SEQ ID NO:61; and the nucleotide sequence is set forth in SEQ ID NO:62. The amino acid sequence of hu2B1-S54A heavy chain variable region is set forth in SEQ ID NO:23, the nucleotide sequence is set forth in SEQ ID NO:24; and the amino acid sequence of light chain variable region is set forth in SEQ ID NO:21, and the nucleoside sequence is shown in SEQ ID NO:22.

293F cells were transiently transfected by 293Fectin and the HCDR of hu2B1-S54A and the same sequence of LCDR were expressed.

Figure 5:
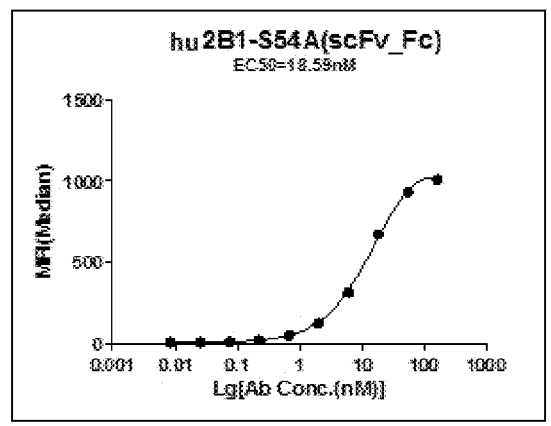
FIG. 5 shows the relative binding affinity of humanized hu2B1-S54A, after fused to human IgG1 Fc portion, to HEK293 cells stably transfected with human CLD18A2.

The binding activity assay was performed as described in Example 2, and experimental data was analyzed using HEK293 cells (HEK-CLD18A2) stably expressing human CLD18A2, GraphPad Prism and Guava easyCyte™ HT System instrument to obtain EC50, and the results are shown in FIG. 5. The relative binding affinity EC50 value of the scFv of hu2B1-S54A, after fused to human IgG1 Fc portion, to HEK293 cell stably transfected with human CLD18A2 was 18.59 nM, indicating that hu2B1-S54A also exhibited a good binding to HEK-CLD18A2.

Example 5. Preparation and Optimization of Humanized Antibody of Monoclonal Antibody 8E5

Following the procedure of Example 4, 8E5 was humanized while the N-glycosylation site in monoclonal antibody 8E5 was removed by point-mutation of S62A to obtain humanized antibody hu8E5 (or hu8E5-S62A). The specific method is described as follows:

(1) IGHV4-30*03 was selected as the antibody template of 8E5 heavy chain, and IGKV4-1*01 was selected as the antibody template of 8E5 light chain. The light chain or heavy chain CDR regions of 8E5 antibody are replaced by the CDR regions of the antibody template.

(2) Reverse mutation sites are determined, there are six potential reverse mutation sites in the heavy chain of humanized antibody (hu8E5), namely G27Y, G45K, L46M, I49M, V68I, V72R, A97T, respectively. There is a potential reverse mutation site in the light chain of humanized antibody (hu8E5), L84V.

(3) Nucleotide sequences were designed, light chain nucleotide sequence was synthesized and a heavy chain nucleotide sequence was synthesized, based on the amino acid sequence of humanized antibody hu8E5.

The heavy chain amino acid sequence of hu8E5-S62A is set forth in SEQ ID NO:67; and the nucleotide sequence is set forth in SEQ ID NO:68. The amino acid sequence of hu8E5-S62A light chain is set forth in SEQ ID NO:65; and the nucleotide sequence is set forth in SEQ ID NO:66. The amino acid sequence of heavy chain variable region of hu8E5-S62A is set forth in SEQ ID NO:27, the nucleotide sequence is set forth in SEQ ID NO:28; the amino acid sequence of light chain variable region of hu8E5-S62A is set forth in SEQ ID NO:25, the nucleotide sequence is set forth in SEQ ID NO:26; HCDR2 in hu8E5-S62A is different from that in 8E5, the sequence of which is set forth in SEQ ID NO:85; and the other HCDRs and LCDR are the same as 8E5.

(4) The synthetic antibody nucleotide sequence including the signal peptide, variable region of the antibody and constant region are inserted into a mammalian cell expression vector to construct an antibody expression vector containing a heavy chain and a light chain, respectively, sequenced and identified. 293F cells were transiently transfected by 293Fectin and expressed.

Figure 6:
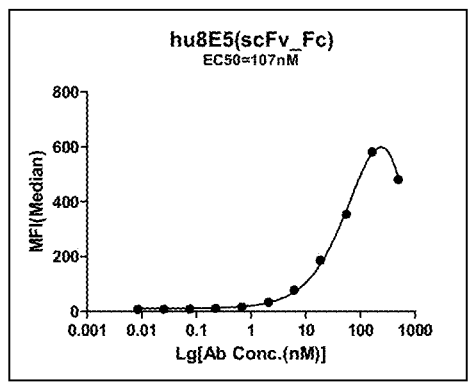
FIG. 6 shows the relative binding affinity of humanized hu8E5, after fused to human IgG1 Fc portion, to HEK293 cells stably transfected with human CLD18A2.

(5) The binding activity was tested, and experimental data was analyzed using HEK293 cells (HEK-CLD18A2) stably expressing human CLD18A2, GraphPad Prism and Guava easyCyte™ HT System instrument, and the results are shown in FIG. 6. It is shown that the relative binding affinity of the scFv of hu8E5, after fused to human IgG1 Fc portion, to HEK293 cell stably transfected with human CLD18A2 was 107 nM.

The 3D model of hu8E5 was established by Discovery studio software, and the potential aggregation sites were analyzed. It was found that the $12^{th}$ and $93^{rd}$ valine of the heavy chain tend to cause aggregation of antibodies, which, in turn affects the stability of the antibody. By analysis on point mutation, it was found that when the two sites were mutated to I, the antibody was more stable. The results of the molecular sieve showed that after these two sites were mutated to I (hu8E5-2I), the proportion of the monomeric form in scFv_Fc fusion antibody was increased from the initial 74% (hu8E5) to 87% (hu8E5-2I).

The amino acid sequence of hu8E5-2I heavy chain of is set forth in SEQ ID NO:63; and the nucleotide sequence is set forth in SEQ ID NO:64. The amino acid sequence of hu8E5-2I light chain is set forth in SEQ ID NO:65; and the nucleotide sequence is set forth in SEQ ID NO:66. HCDR2 in hu8E5-2I is different from that in 8E5, but is identical to that in hu8E5, and its sequence is shown in SEQ ID NO: 85; other HCDRs and LCDR are the same as 8E5.

Figure 7:
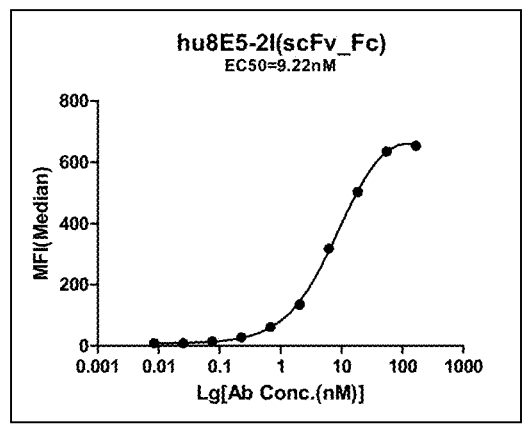
FIG. 7 shows the relative binding affinity of engineered humanized hu8E5-2I to HEK293 cells stably transfected with human CLD18A2.

The mutant hu8E5-2I of the humanized antibody hu8E5 was constructed as described in Example 3. Experimental data was analyzed using HEK293 cells (HEK-CLD18A2) stably expressing human CLD18A2, GraphPad Prism and Guava easyCyte™ HT System instrument, and the results are shown in FIG. 7. The relative binding affinity, EC50 value of the scFv of hu8E5-2I, after fused to human IgG1 Fc portion, to HEK293 cell stably transfected with human CLD18A2 was 9.22 nM. Compared with the parent antibody 8E5, the affinity of mutant hu8E5-2I had a 5-fold increase.

Example 6. In Vitro Functional Assay and In Vivo Functional Assay of Humanized Antibody hu2B1-S54A and Humanized Antibody hu8E5-2I The humanized antibody hu2B1-S54A (light chain sequence: SEQ ID NO:62, heavy chain sequence: SEQ ID NO:60); humanized antibody hu8E5-2I (Light chain sequence: SEQ ID NO:66, heavy chain sequence: SEQ ID NO:64) were cloned into a eukaryotic expression vector by standard methods known to a skilled person. 293F cells in logarithmic growth phase were transiently transfected with 293Fectin™ Transfection reagent (Invitrogen, 12347-019), and the culture supernatant was collected and subjected to affinity purification. The obtained antibodies were quantitatively and qualitatively analyzed by SDS PAGE. The above eukaryotic expression vector uses the vector pH or vector pK used in CN101602808B.

1. Complement Dependent Cytotoxicity (CDC)

Blood was collected from healthy volunteers and serum was prepared by centrifugation. A CCK-8 cell proliferation-toxicity assay kit (Dojindo, #CK04) was used. HEK293 cells stably transfected with CLD18A2 or CLD18A1 were used as target cells. The cells were washed twice, resuspended in complete medium at a density of $1\times10^5$ cells/ml, seeded in a 96-well culture plate at 100 μl per well and cultured overnight at 37° C. The next day, antibody was added to each well at a final concentration of 20 μg/ml, and incubate for 30 min at 37° C. in an incubator. Then, serum at a final concentration of 10% was added and incubated at 37° C. for 1.5 hours. 10 ul of CCK-8 solution was added to each well, incubated at 37° C. for 3.5 h (adjusted as appropriate), and the absorbance at 450 nm was measured with a microplate reader. The experiment was divided into six groups and duplicate wells were set up, as shown in the following table.

2. Antibody-Dependent Cytotoxicity (ADCC) Activity

The ADCC activity of the humanized antibody, claudin 18A2 antibody was measured by a lactate dehydrogenase (LDH) release assay using a cytoTox 96 non-radioactive cytotoxicity assay kit (Promega, Madison, USA). Human peripheral blood mononuclear cells (PBMC) were purified from citrated whole blood by standard Ficoll-paque separation and resuspended in complete medium (RPMI-1640 culture, Gibco) supplemented with 10% fetal bovine serum (FBS, Gibco) at a density of $8\times10^6$ cells/ml. HEK293 cells stably transfected with CLD18A2 were used as target cells. The cells were washed twice and resuspended in a complete culture at a density of $2\times10^5$ cells/ml. PBMCs were incubated with an antibody at a final concentration of 20 ug/ml for 30 minutes at 37° C., and then 50 μl of antibody and effector cells were added into 50 μl of target cells at a effector-to-target ratio of 50:1, 20:1, 10:1 (total $1\times10^4$ target cells). After incubated for 4 hours at 37° C., the cells were centrifuged, and 50 μl of cell-free supernatant sample was collected, transferred to a flat-bottomed 96-well plate, and assayed. The percentage of lysis was calculated as follows: (sample release−target spontaneous release−spontaneous release of effector cells)/(maximum release−target spontaneous release)*100; wherein the target spontaneous release is fluorescence in wells containing only target cells, spontaneous release of effector cells is fluorescence in wells containing only effector cells, and maximum release is fluorescence in wells containing target cells that have been treated with lysis buffer.

TABLE 6

| | Grouping | | | | | | |
|---|---|---|---|---|---|---|---|
| Experimental Materials | experiment well | Lysis well | antibody control well | complement control well | cell control well | cell Blank well | Blank well |
| CLD18A2 cell 1*10⁶/ml | 100 ul | 100 ul | 100 ul | 100 ul | 100 ul | 0 | 0 |
| DMEM | −50 ul | 0 | −50 ul | −25 ul | 0 | 50 ul | 100 ul |
| Ch-163E12 antibody 60 ug/ml | 25 ul | Lysate 10 ul | 25 ul | 0 | 0 | 25 ul | 0 |
| Complement (serum)40% | 25 ul | | 25 ul | 25 ul | 0 | 25 ul Inactivated complement | 0 |
| CCK-8 solution | 10 ul | 10 ul | 10 ul | 10 ul | 10 ul | 10 ul | 10 ul | lysis percentage is calculated as follows:

Lysis percentage=(cell control well−experiment well)/cell control well−(cell control well−antibody control well)/cell control well.

Figure 8A:
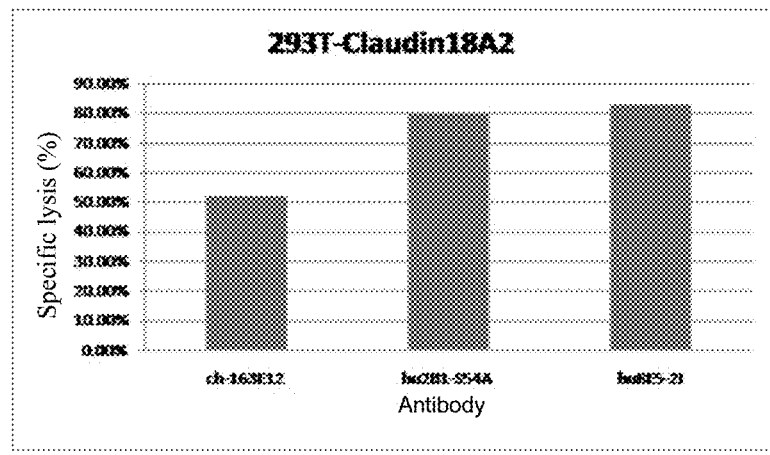
FIGS. 8A-8B.
Figure 8B:
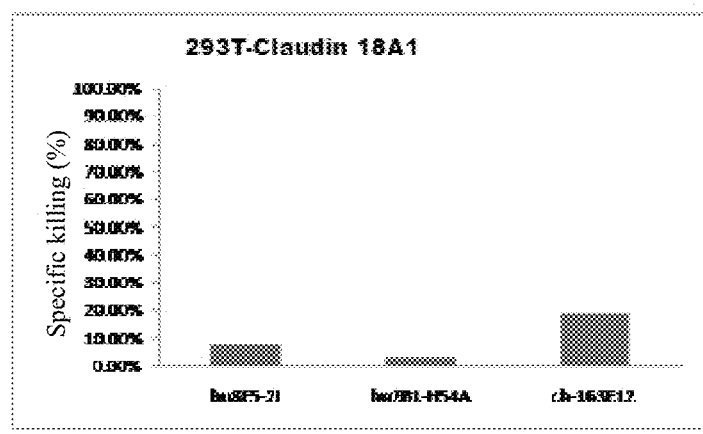

FIG. 8A compares CDC effects of the humanized antibodies hu2B1-S54A, hu8E5-2I and the chimeric antibody ch-163E12 on HEK293 cells transfected with CLD18A2. The experiment results showed that when the concentration of hu2B1-S54A and hu8E5-2I were 20 μg/ml, CDC effects against HEK293-CLD18A2 were 79.88% and 82.65%, respectively, and CDC effects of ch-163E12 under the same reaction conditions was lower than 55%. FIG. 8B compares CDC results of the humanized antibodies hu2B1-S54A, hu8E5-2I and chimeric antibody ch-163E12 on HEK293 cells transfected with CLD18A1. The results showed that ch-163E12 also had a certain killing on cells expressing 18A1, and hu2B1-S54A and hu8E5-2I did not kill cells expressing 18A1.

Figure 9:
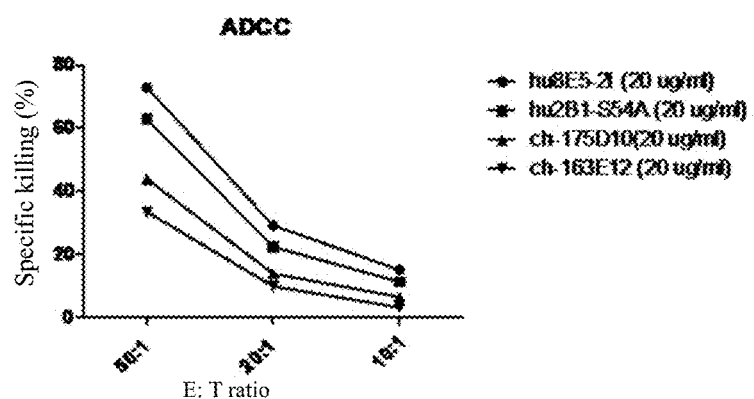
FIG. 9 compares ADCC effects of the humanized antibodies hu2B1-S54A, hu8E5-2I and the chimeric antibodies ch-163E12, ch-175D10 (see CN103509110A).

FIG. 9 compares ADCC effects of the humanized antibodies hu2B1-S54A, hu8E5-2I and the known chimeric antibodies ch-163E12, ch-175D10 (see CN103509110A). The experimental results showed that the humanized antibodies hu2B1-S54A and hu8E5-2I, at an antibody concentration of 20 μg/ml and a effector-to-target ratio of 50:1, 20:1 and 10:1, exhibited significantly higher ADCC effects than ch-175D10 and ch-163E12, and the ADCC effects against HEK293-CLD18A2 at a effector-to-target ratio of 50:1 were 62.84% and 72.88%, respectively. While the ADCC effects of ch-163E12 and ch-175D10 against HEK293-CLD18A2 under the same reaction conditions were only 33.39% and 43.74%. The antibody of the present invention exhibits significantly better killing effects than ch-163E12 and ch-175D10.

3. In Vivo Experiment in Mice

Establishment of a PDX model of gastric cancer: Tumors of about 3 mm×3 mm×3 mm in size were inoculated subcutaneously into the right ankle of BALB/c nude mice. The day of tumor cell inoculation was recorded as D0 days, the tumor volume was measured at D27 from the inoculation of tumor, and the mice were randomly divided into 5 groups. The specific groups are as follows: (1) PBS (phosphate buffer) control group; (2) hu8E5-2I antibody treatment group (40 mg/kg); (3) EOF treatment group (E is epirubicin: 1.25 mg/Kg; O is oxaliplatin: 3.25 mg/kg; F is 5-fluorouracil: 56.25 mg/kg)+PBS; (4) hu8E5-2I antibody (40 mg/kg)+EOF treatment group (1.25 mg/kg Epirubicin+3.25 mg/kg oxaliplatin+56.25 mg/kg 5-fluorouracil); (5) ch175D10 antibody (40 mg/kg)+EOF treatment group (1.25 mg/kg epirubicin+3.25 mg/kg oxaliplatin+56.25 mg/kg 5-fluorouracil). Dosage: EOF was administered once a week for 2 weeks; hu8E5-2I and ch175D10 antibodies were administered 3 times per week for 2 weeks.

Figure 10:
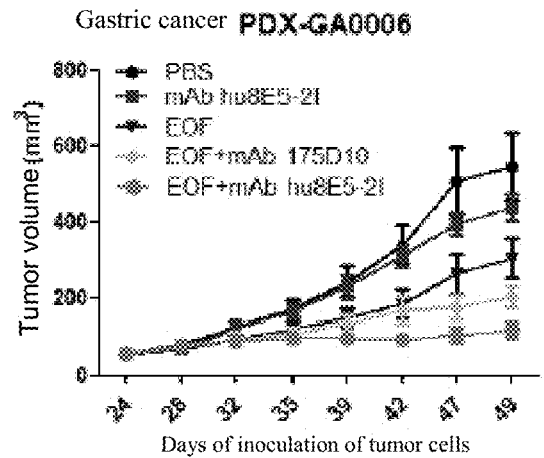
FIG. 10 compares killing activities of hu8E5-2I and ch-175D10 in mice.

The results are shown in FIG. 10. The tumor was inoculated for D56 days, the EOF was injected twice, the antibody was injected 6 times, and the mice were sacrificed by cervical dislocation. Compared with the PBS control group, the tumor inhibition rates were: 21.13% in the hu8E5-2I monoclonal antibody group, 47.89% in the EOF+PBS treatment group, 81.69% in the EOF+mAb hu8E5-2I treatment group, and 71.83% in the EOF+mAb 175D10 treatment group, respectively. From the tumor weighing, the EOF+mAb hu8E5-2I treatment group was statistically different over the EOF+PBS group, P=0.033; while the EOF+mAb 175D10 treatment group was not statistically different over the EOF+PBS group, P=0.097.

Example 7. Construction of Humanized Antibody Chimeric Antigen Receptor Plasmid (CAR Plasmid)

1. Construction of Humanized Antibody hu8E5 Chimeric Antigen Receptor Plasmid

Using PRRLSIN-cPPT.EF-1α as a vector, lentiviral plasmids encoding the second and third generation of chimeric antigen receptors of humanized antibody hu8E5 were constructed, including PRRLSIN-cPPT.EF-1α-hu8E5-28Z, PRRLSIN-cPPT.EF-1α-hu8E5-BBZ and PRRLSIN-cPPT.EF-1α-hu8E5-28BBZ.

Hu8E5-28Z mainly includes (from 5' to 3' end): encoding sequence of CD8α signal peptide (SEQ ID NO:70), hu8E5 scFV (VH: SEQ ID NO:27, VL: SEQ ID NO:25, Linker: SEQ ID NO:93), CD8 hinge (SEQ ID NO:72), CD28 transmembrane region (SEQ ID NO:74) and intracellular signaling domain (SEQ ID NO:76) as well as intracellular segment CD3ξ of CD3 (SEQ ID NO:78).

hu8E5-BBZ mainly includes (from 5' to 3' end): encoding sequence of CD8α signal peptide (SEQ ID NO:70), hu8E5 scFV (VH: SEQ ID NO:27, VL: SEQ ID NO:25, Linker: SEQ ID NO:93), CD8 hinge (SEQ ID NO:72), CD8 transmembrane region (SEQ ID NO:80), CD137 intracellular signaling domain (SEQ ID NO:82) and CD3ξ (SEQ ID NO:78).

hu8E5-28BBZ mainly includes (from 5' to 3' end): encoding sequence of CD8α signal peptide (SEQ ID NO:70), hu8E5-scFV, CD8 hinge (SEQ ID NO:72), CD28 transmembrane region (SEQ ID NO:74) and intracellular segment (SEQ ID NO:76), CD137 intracellular signaling domain (SEQ ID NO:82) and CD3ξ (SEQ ID NO:78).

2. Construction of Humanized Antibody hu8E5-2I Chimeric Antigen Receptor Plasmid Using PRRLSIN-cPPT.EF-1α as a vector, lentiviral plasmid PRRLSIN-cPPT.EF-1α-hu8E5-2I-28Z encoding the second generation of chimeric antigen receptors of humanized antibody hu8E5 was constructed.

hu8E5-2I-28Z mainly includes (from 5' to 3' end): encoding sequence of CD8α signal peptide (SEQ ID NO:70), hu8E5-2I scFV (VH: SEQ ID NO:29, VL: SEQ ID NO:25, Linker: SEQ ID NO:93), CD8 hinge (SEQ ID NO:72), CD28 transmembrane region (SEQ ID NO:74) and intracellular signaling domain (SEQ ID NO:76) and intracellular signaling domain CD3ξ of CD3 (SEQ ID NO:78).

3. Construction of Humanized Antibody hu2B1-S54A Chimeric Antigen Receptor Plasmid Using PRRLSIN-cPPT.EF-1a as a vector, lentiviral plasmid PRRLSIN-cPPT.EF-1α-hu2B1-S54A-28Z encoding the second generation of chimeric antigen receptors of humanized antibody hu2B1-S54A was constructed.

hu2B1-S54A-28Z mainly includes (from 5' end to 3' end): encoding sequence of CD8α signal peptide (SEQ ID NO:70), hu2B1-S54A scFV (VH: SEQ ID NO:23; VL: SEQ ID NO:21; Linker: SEQ ID NO:93), CD8 hinge (SEQ ID NO:72), CD28 transmembrane region (SEQ ID NO:74) and intracellular segment (SEQ ID NO:76), and intracellular CD3Z of CD3 (SEQ ID NO:78).

Example 8. Lentiviral Packaging and Titer Determination

The 293T cells cultured to the $6^{th}$ to $10^{th}$ passage were inoculated at a virus density of $5\times10^6$ in a 10 cm culture dish, and cultured overnight at 37° C., 5% $CO_2$ for transfection, and the medium was DMEM containing 10% fetal bovine serum (Gibico).

The target gene plasmid PRRLSIN-cPPT.EF-1α-EGFP (Mock) and different CAR plasmids prepared in Example 9 (5.4 μg) and packaging plasmid pRsv-REV (6.2 μg), RRE-PMDLg (6.2 μg) and Vsvg (2.4 μg) were dissolved in 800 μL of blank DMEM medium; 60 μg of PEI (1 μg/μl) was dissolved in 800 μl of serum-free DMEM medium and mixed for 5 min at room temperature.

The plasmid mixture was added to PEI mixture, and mixed for 20 min at room temperature to form a transfection complex; 1.6 ml of the transfection complex was added dropwise to a 10 cm culture dish containing 11 ml of DMEM medium; after 4-5 hours, 10% FBS DMEM medium was used to change the medium for the transfected 293T cells, and incubated at 37° C. for 72 h. The virus supernatant was collected and concentrated, and the titer was determined. The number of cells with a positive rate of 5~20% was preferred, and the titer (U/mL) was calculated as =cell number×positive rate/virus volume.

Upon concentration, the virus titers were:
hu8E5-28Z: $2.3\times10^7$ U/ml;
hu8E5-BBZ: $6.65\times10^7$ U/ml;
hu8E5-28BBZ: $6.67\times10^7$ U/ml;
hu8E5-2I-28Z: $1.54\times10^8$ U/ml;
hu2B1-S54A-28Z: $1.14\times10^8$ U/ml.

Example 9. Cytotoxicity Assay of Lentiviral-Transduced T Lymphocytes and CAR-T Cells 1. Lentivirus-Infected T Lymphocytes (1) Lymphocyte culture medium was added at a density of about $1\times10^6$/mL for culture, and magnetic beads (Invitrogen) coated with anti-CD3 and CD28 antibodies and recombinant human IL-2 with a final concentration of 300 U/mL were added according to a magnetic bead: cell ratio of 1:1 for stimulation and culture for 48h;

(2) Retronectin coated 24-well plates: 380 μl of 5 μg/ml retronectin solution (PBS) was added to each well, and after incubation at 4° C. overnight, the retronectin solution (PBS) in a 24-well plate was discarded, and washed twice with 1 ml of PBS;

(3) Cells were seeded in a 24-well plate coated with retronectin. The number of cells per well was $3\times10^5$, and the volume of the culture solution was 600 µl. The concentrated lentivirus was added to PBMCs cells at MOI=10, centrifuged at 32° C. for 40 min and transferred to a cell culture incubator;

(4) Expansion culture: The infected cells were passaged every other day at a density of $5\times10^5$/mL, and recombinant human IL-2 was supplemented in the lymphocyte culture solution at a final concentration of 300 U/mL.

2. T Lymphocyte Chimeric Antigen Receptor Expression (1) On the $7^{th}$ day of culture of lentivirus-infected T lymphocytes, $1\times10^6$ T cells were taken, aliquoted into a 2 ml centrifuge tube, centrifuged at 4° C., 5000 rpm for 5 min, the supernatant was discarded, and PBS was washed twice.

(2) Control cells were added 50 µl of PE-SA (1:200 dilution) antibody and incubated for 45 min on ice, washed twice with PBS (2% NBS), and resuspended as a control; cells in the test group+50 µl 1:50 diluted biotin-Goat anti human IgG, F(ab')2 antibody, incubated on ice for 45 min; washed twice with PBS (2% NBS).

(3) 50 µl of PE-SA (1:200 dilution) antibody was added and incubated for 45 min on ice; 2 ml of PBS (2% NBS) was added for resuspending the cells, and the supernatant was discarded upon centrifugation.

(4) Proportion of CAR-positive T cells was detected by Flow cytometry. The infection positive rates of three CAR T cells, hu8E5-28Z, hu8E5-BBZ and hu8E5-28BBZ and Mock control cells were 52.1%, 47.8%, 44.6% and 71.7%, respectively.

3. Cytotoxicity Assay of CLD18A2-Targeting CAR T Cells (1) Target cells: 75 µL of $2\times10^5$/mL 293T-A1 cells, 293T-A2 cells, gastric adenocarcinoma cell line AGS, AGS-A2, gastric cancer cell lines BGC-823, and BGC-823-A2 cells were inoculated respectively. Gastric adenocarcinoma cell line AGS, gastric cancer cell line BGC-823 were purchased from ATCC cell bank, 293T-A1 cells, 293T-A2 cells, AGS-A2, BGC-823-A2 cells were constructed with reference to CN101602808B, among which 293T-A2 cells, AGS-A2, and BGC-823-A2 cells were CLD18A2-positive cells, and the rest were CLD18A2-negative cells.

(2) Effector cells: T-Mock and CAR T cells expressing different chimeric antigen receptors were added at an effector-to-target ratio of 3:1, 1:1 or 1:3;

(3) 4 duplicate wells were set for each group, and the average of 4 replicate wells was taken. The detection time was 18h.

Each experimental group and each control group are as follows:

Each experimental group: each target cell+CAR T expressing different chimeric antigen receptors;

Control group 1: maximum release of LDH from target cells;

Control group 2: spontaneous release of LDH from target cells;

Control group 3: spontaneous release of LDH from effector cells;

(4) Detection method: CytoTox 96 non-radioactive cytotoxicity test kit (Promega) was used. CytoTox 96® assay quantitatively measures lactate dehydrogenase (LDH), in particular, referring to instructions of CytoTox 96 Non-Radioactive Cytotoxicity Assay Kit.

(5) The calculation formula for cytotoxicity is:

$$\text{Cytotoxicity \%} = (\text{Experimental group} - \text{Control group 2} - \text{Control group 3}) / (\text{Control group 1} - \text{Control group 2}) * 100\%$$

Figure 11:
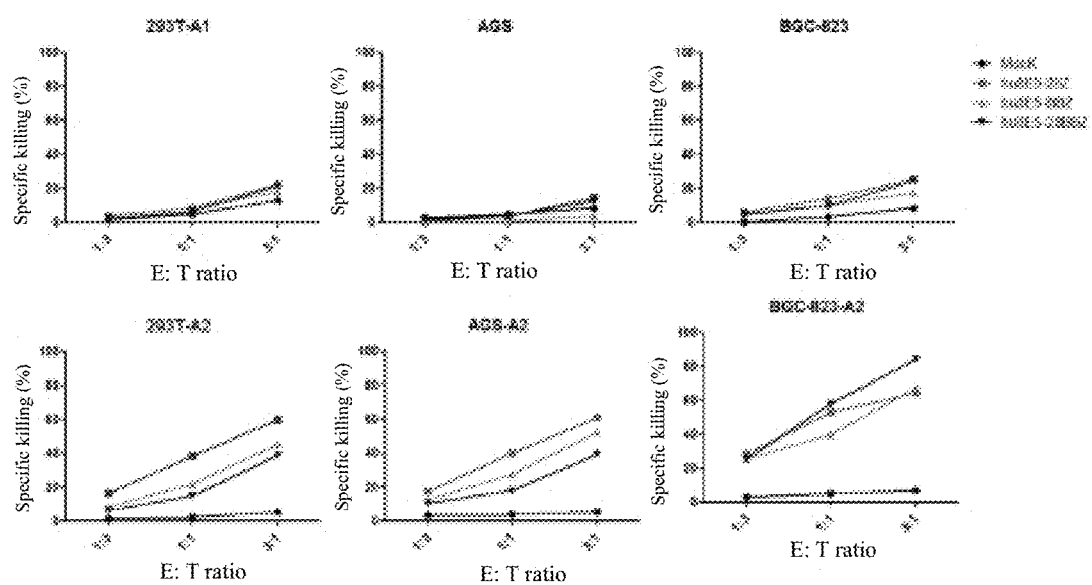
FIG. 11 compares in vitro killing activities of hu8E5-28Z, hu8E5-BBZ and hu8E5-28BBZ T cells on different cell lines.
Figure 12:
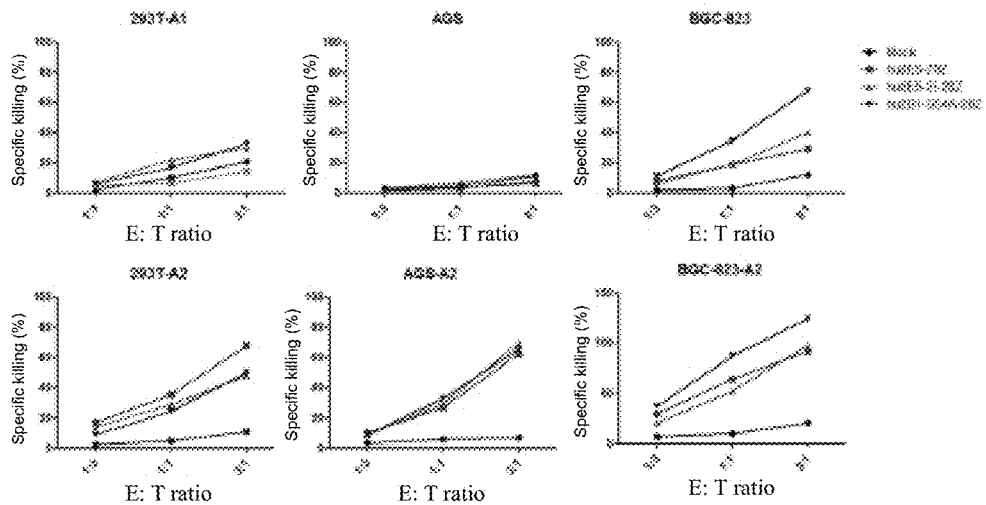
FIG. 12 compares in vitro killing activities of hu8E5-28Z, hu8E5-2I-28Z and hu2B1-hs54A T cells on different cell lines.

The cell killing results at different effector-to-target ratios are shown in FIG. 11 and FIG. 12. The results showed that the CAR-T products showed good killing effects on 293T-A2, AGS-A2 and BGC-823-A2 cells with positive CLD18A2 expression. Among them, hu8E5-28Z and hu8E5-2I-28Z cells can kill more than 60% of AGS-A2 cells at an effector-to-target ratio of 3:1, and the killing effects on BGC-823-A2 cells can reach higher than 90%. At the same time, the results also showed that the killing effects of each CAR T cell (except Hu2B1-S54A-28Z) on cells with negative expression of CLD18A2 was not obvious.

Example 10. In Vivo Activity of CLD18A2 CAR-T Cell

Anti-tumor treatment experiments of untransfected T cells (UTD) and hu8E5-2I-28Z T cells on subcutaneously transplanted tumors in gastric cancer PDX were observed.

1) Establishment of PDX model of gastric cancer: a gastric cancer PDX tumor of about 2×2×2 mm was inoculated in the right axillary area of female NOD/SCID mice of 6-8 weeks old, and the day of tumor cell inoculation was recorded as D0 day.

2) Experimental group: The tumors were inoculated for 15 days, and NOD-SCID mice were randomly divided into 3 groups, 7 in each group, untransfected T cell group and hu8E5-2I-28Z T cell group.

Figure 13A:
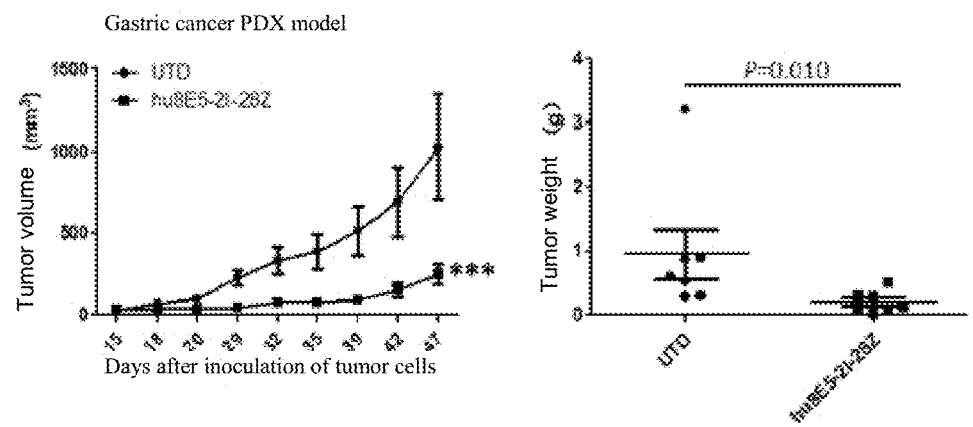
FIGS. 13A-13B are comparison graphs of the effect of CLDN18A2-CAR T on tumor volume over time in a subcutaneous xenograft model of gastric cancer PDX mice (FIG. 13A) and a comparison graph of tumor photographs (FIG. 13B).
Figure 13B:
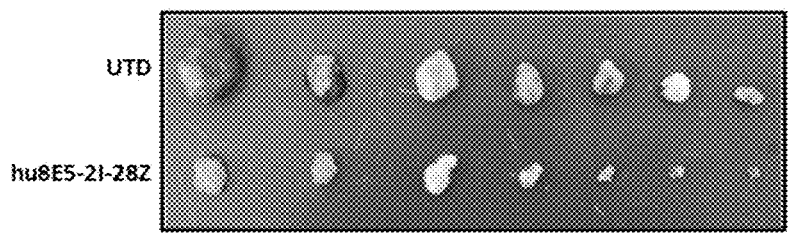

3) Adoptive transfer of T cells: 100 mg/kg of cyclophosphamide was intraperitoneally injected when a tumor volume was 30 mm$^3$, and $1.0\times10^7$ CAR-T cells were infused through the tail vein 24 hours after injection, while untransfected T cell groups were used as control. The growth of subcutaneous xenografts of gastric cancer PDX was observed and measured. The experiment results are shown in FIGS. 13A and 13B. On the D32 day after CART injection, the mice were sacrificed by cervical dislocation. Compared with the UTD group, the anti-tumor effect of the hu8E5-2I-28Z treatment group was significant, and the inhibition rate was 79.2%. From the tumor weighing, the hu8E5-2I-28Z treatment group was statistically different over the UTD group, P=0.01.

Example 11. Cytokine Release Assay Induced by CLD18A2 CAR-T Cells In Vitro

To verify whether the constructed hu8E5-28Z and hu8E5-2I-28Z T cells can be efficiently activated under stimulation of target cell, we examined secretion of cytokines from hu8E5-28Z and hu8E5-2I-28Z T cells after co-incubation with target cells.

Cytokines released by transfected T cells (Mock), hu8E5-28Z and hu8E5-2I-28Z T cells were detected respectively. The above two T cells of good growth within 1-2 weeks after lentivirus infection were collected, inoculated in a 24-well plate at $5\times10^4$/200 µL (positive cell number), and $5\times10^4$/200 µL/24 well of target cells were inoculated at an effector-totarget ratio of 1:1. The target cells include 293T-A1, 293T-A2, AGS, AGS-A2, BGC-823 and BGC-823-A2 cells. The supernatant was collected after 24 hours of co-cultivation. The sandwich ELISA method was used to detect IL2, IFN-γ and TNF-α in the supernatant released during the co-culture of CAR T lymphocytes with target cells.

Figure 14:
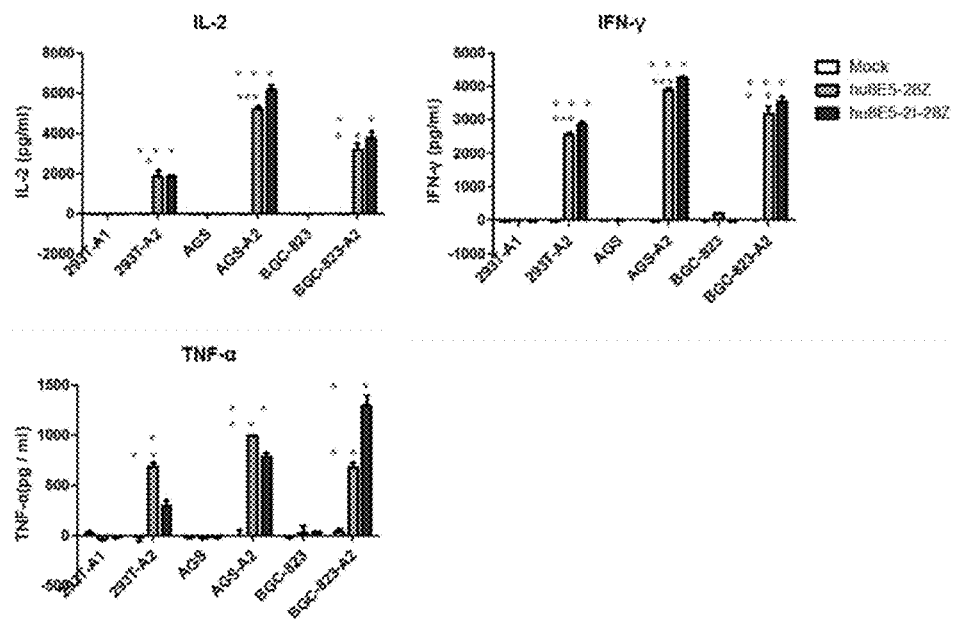
FIG. 14 shows results of secretion assay of cytokines of hu8E5-28Z and hu8E5-2I-28Z.

The experiment results are shown in FIG. 14. The results showed that when hu8E5-28Z, hu8E5-2I-28Z were incubated with CLD18A2 positive 293T-A2, AGS-A2 and BGC-823-A2 cells, the secretion of IL-2, IFN-γ and TNF-α cytokines was activated, while in the Mock control group, the secretion of these cytokines can not be activated and there were significant differences; when hu8E5-2I-28Z was incubated with 293T-A1, AGS and BGC-823 cells with negative expression of CLD18A2, the secretion of IL-2, IFN-γ and TNF-α cytokines can not be activated, and in the Mock control group, the secretion of the above cytokines can not be activated either. The above experimental results indicate that cells with positive expression of CLD18A2 can effectively activate hu8E5-2I-28Z CAR T cells.

Example 12. In Vivo Killing Activity of CLD18A2 CAR-T Cells

Anti-tumor treatment experiments of untransfected T cells (Mock), hu8E5-28Z and hu8E5-2I-28Z T cells on subcutaneous xenografts of BGC-823-A2 cells were determined.

1) Inoculation of BGC-823-A2 subcutaneous xenografts: BGC-823-A2 cells collected in logarithmic growth phase and grown well were adjusted to a density of $2.5 \times 10^7$/mL using physiological saline, and a volume of the cell suspension (200 μL, $5 \times 10^6$/animal) was injected subcutaneously in the right side of the mouse. The day of tumor cell inoculation was recorded as day 0.

2) Experiment groups: On the $11^{th}$ day of tumor inoculation, the volume of BGC-823-A2 tumor was measured, and the NOD-SCID mice were randomly divided into 3 groups, 6 mice of each group. The groups were untransfected T cell group, hu8E5-28Z T cell, and hu8E5-2I-28Z T cell group, respectively.

3) Adoptive transfer of T cells: 100 mg/kg of cyclophosphamide was intraperitoneally injected when the tumor volume was 100-150 mm³ (Day 11), and $1 \times 10^7$ CART cells (Mock cells, hu8E5-28Z T cells or hu8E5-2I-28Z T cells) were infused through the tail vein 24 hours after the injection, and the untransfected T cell group (Mock group) was used as a control to observe the growth of subcutaneous xenografts.

Figure 15:
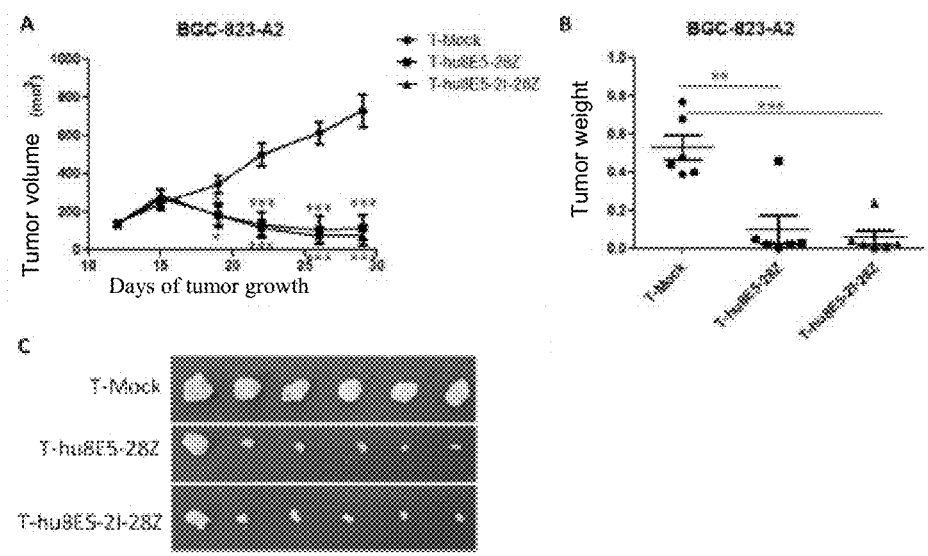
FIGS. 15A-15C are comparison graphs of the effect of CLDN18A2-CAR T on tumor volume over time in a subcutaneous xenograft model of gastric cancer BGC-823-A2 mice (FIG. 15A), a comparison graph of tumor weight (FIG. 15B) and a comparison graph of tumor photo (FIG. 15C).

The results of animal experiments are shown in FIG. 15. The results showed that on the $17^{th}$ day of treatment of hu8E5-28Z and hu8E5-2I-28Z CAR T cells, the tumor inhibition rates of BGC-823-A2 xenografts were 81.3% and 89.2%, respectively; and there were significant differences in the therapeutic effects on BGC-823-A2 xenografts between the hu8E5-28Z, hu8E5-2I-28Z treatment group and the Mock control group. After the $17^{th}$ day of treatment, the mice were sacrificed and the tumors were removed and weighed. The average tumor weight of the transplanted tumors of BGC-823-A2 in the hu8E5-28Z and hu8E5-2I-28Z treatment groups were 0.1 and 0.06 g, respectively, while the average weight of tumor in the Mock control group was 0.53 g, and there were significant differences between the CAR T cell treatment group and the Mock control group, and the P values were 0.0013 and <0.0001, respectively.

Example 13. Effect of CLD18A2 CAR-T Cells on Tumor Infiltration In Vivo

According to the animal model of BGC-823-A2 cell subcutaneous xenograft established in Example 12, 17 days after Mock, hu8E5-28Z, and hu8E5-2I-28Z cells were returned, tumor tissues were taken and CD3+ cells were detected by histochemistry.

Figure 16:
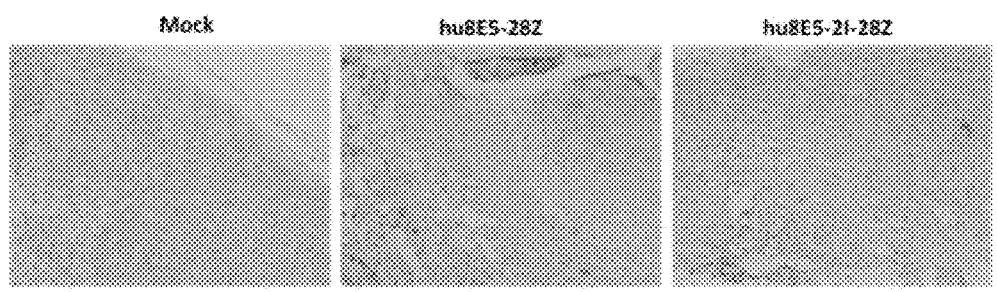
FIG. 16 shows the tumor infiltration of CLDN18A2-CAR T.

Results are shown in FIG. 16. Almost no T cell infiltration was observed around the tumor tissue in Mock T cell group, almost no T cell infiltration was observed around the tumor tissue in Mock T cell group; in hu8E5-28Z and hu8E5-2I-28Z cell groups, infiltration of CD3+ T cells can be observed at the edge of the tumor tissue; and more T cell infiltration can be observed at the edge of the tumor tissue in hu8E5-2I-28Z treatment group.

Example 14. Preparation of CAR-T Cells Co-Expressing IFN

According to the procedure of Examples 7-9, a plasmid of hu8E5-28Z-IFNb CAR expressing IFNb cytokine was constructed based on hu8E5-28Z, and hu8E5-2I-28Z-IFN CAR plasmid which can express IFNb cytokine was constructed based on hu8E5-2I-28Z CAR, which were packaged and infected with lentivirus, so that hu8E5-28Z-IFNb CAR T cells co-expressing IFNb (also labeled as hu8E5-28Z&IFNB) and hu8E5-2I-28Z-IFN CAR T cells co-expressing IFNb (also labeled as hu8E5-2I-28Z&IFNB) were obtained. hu8E5-28Z-IFNb CAR is encoded by the nucleotide sequence of SEQ ID NO:90; and hu8E5-2I-28Z-IFN CAR is encoded by the nucleotide sequence of SEQ ID NO:91.

Figure 17A:
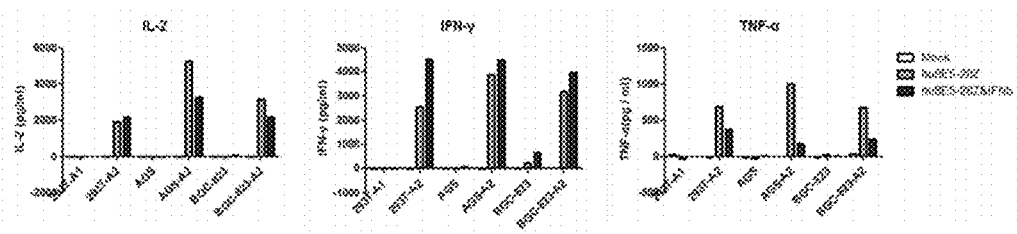
FIGS. 17A-17C.

According to the procedure of Example 11, in vitro induction of cytokine release assay was carried out. The results are shown in FIG. 17A, and the presence of IFN resulted in an increase in IFN-γ cytokine secretion when hu8E5-28Z CART cells were co-incubated with target cells.

Figure 17B:
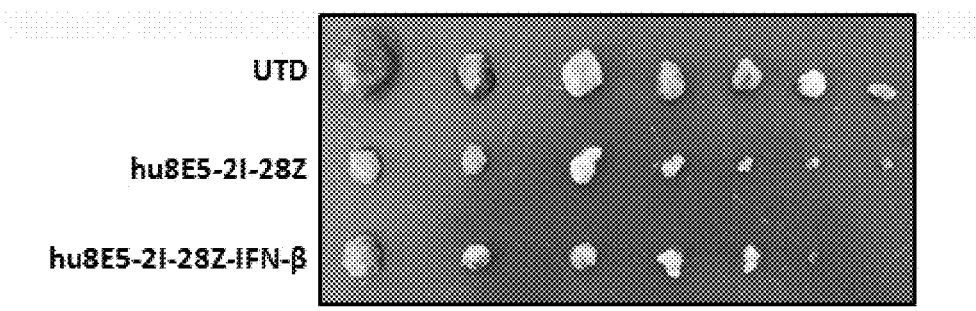

Anti-tumor treatment experiments of untransfected T cells (UTD), hu8E5-28Z T cells and hu8E5-2I-28Z-IFN T cells on subcutaneous xenografts of gastric cancer PDX model were observed. A gastric cancer PDX tumor of about 2×2×2 mm was subcutaneously inoculated in the right axilla of 6-8 weeks old female NOD/SCID mice, and the day of tumor cell inoculation was recorded as D0 day. On D15 day of tumor inoculation, NOD-SCID mice were randomly divided into 3 groups, 7 in each group, untransfected T cell group, hu8E5-28Z T cell group and hu8E5-2I-28Z-IFN T cell group. When the tumor volume was 30 mm³, 100 mg/kg of cyclophosphamide was intraperitoneally injected, and 1.0× $10^7$ CAR-T cells (hu8E5-28Z T cells or hu8E5-2I-28Z-IFN T cells) were infused through the tail vein 24 hours after the injection. At the same time, the untransfected T cell group was used as a control. The growth of subcutaneous xenografts of gastric cancer PDX were observed and measured. The results were shown in FIG. 17B, and in one of the 7 mice in the hu8E5-2I-28Z-IFN-treated group, the tumor completely regressed.

Figure 17C:
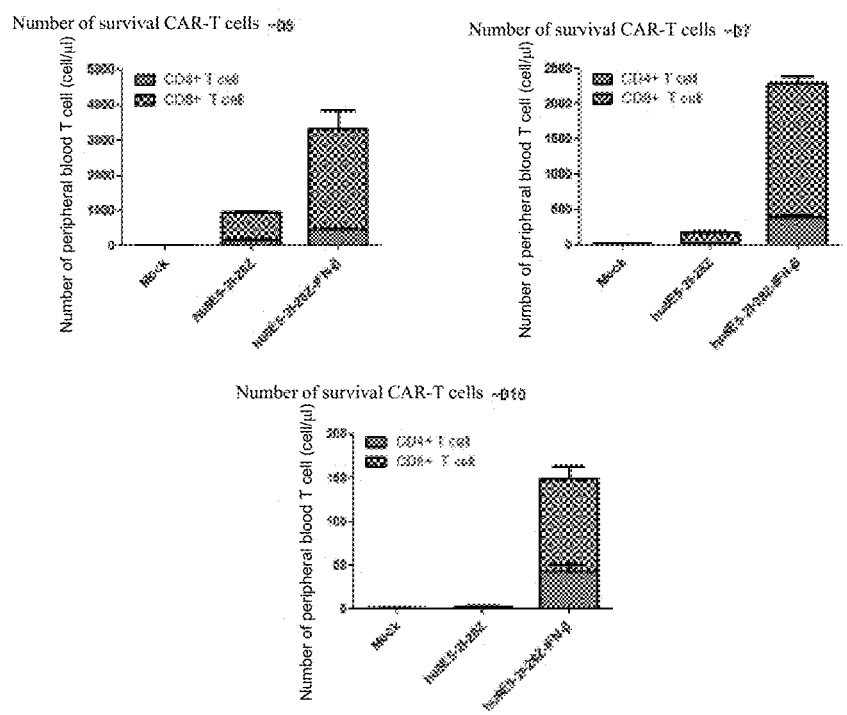

CAR-T cells was determined for in vivo survival using PDX model described above. Peripheral blood was collected from the saphenous vein of mice at D5, D7 and D10 days after CAR-T infusion, and CAR-T cells (blank T cells (Mock), hu8E5-28Z T cells or hu8E5-2I-28Z-IFN T cells) were detected for in vivo survival. The results were shown in FIG. 17C, and, the survival number of T cell in the hu8E5-2I-28Z-IFN T cell treated group was significantly higher than that of the hu8E5-28Z-28Z T cell treatment group.

Example 15. Construction of CAR-NK Cell

As shown in the plasmid maps shown in FIGS. 18A and 18B, using PRRLSIN-cPPT.EF-1α as a vector, lentiviral plasmids encoding the chimeric antigen receptors of humanized antibody hu8E5 were constructed, including PRRLSIN-cPPT.EF-1α-hu8E5-28BBZ and PRRLSIN-cPPT.EF-1α-hu8E5-2I-28Z. The hu8E5-28BBZ sequence consists of a CD8α signal peptide (SEQ ID NO:70), hu8E5-scFV, CD8 hinge (SEQ ID NO:72), a CD28 transmembrane region (SEQ ID NO:74) and an intracellular segment (SEQ ID NO:76), CD137 intracellular signaling domain segment (SEQ ID NO:82) and CD3ξ (SEQ ID NO:78); and hu8E5-2I-28Z sequence consists of CD8α signal peptide (SEQ ID NO:70), hu8E5-2I scFV, CD8 hinge (SEQ ID NO:72), CD28 transmembrane region (SEQ ID NO:74) and CD28 intracellular signaling domain (SEQ ID NO:76) and CD3ξ intracellular segment of CD3 (SEQ ID NO:78).

1. Preparation of CAR-Positive NK-92 Cell Line

1) Retronectin coated 24-well plates: 380 µl of 5 µg/ml retronectin solution (PBS) was added to each well, and incubated at 4° C. overnight. Cells were seeded in the 24-well plate coated with retronectin. The number of cells per well was 5×10$^5$, and the volume of the culture solution was 500 µl;

2) The concentrated lentivirus was added to NK92 cells at MOI=30, centrifuged at 32° C. for 90 min and transferred to a cell culture incubator;

3) Expansion culture: The infected cells were passaged every other day at a density of 5×10$^5$/mL, and recombinant human IL-2 was supplemented in the lymphocyte culture solution at a final concentration of 500 U/mL.

2. Expression of NK-92 Cell Chimeric Antigen Receptor (1) On the 7$^{th}$ day of culture of lentivirus-infected NK92 cells, 1×10$^6$ cells were taken, aliquoted into a 2 ml centrifuge tube;

(2) Control cells were added 50 µl of PE-SA (1:200 dilution) antibody and incubated on ice and resuspended as a control; cells in the test group+50 µl 1:50 diluted biotin-Goat anti human IgG, F(ab')2 antibody, incubated on ice for 45 min; washed twice with PBS (2% NBS); 50 µl of PE-SA (1:200 dilution) antibody was added and incubated on ice;

(3) 2 ml of PBS (2% NBS) was added for resuspending the cells, and the supernatant was discarded upon centrifugation at 4° C.; 500 µl of PBS (2% NBS) was added and transferred to a flow tube. The PE channel was detected by flow cytometry to determine the proportion of CAR positive NK92 cells. The results are shown in FIG. 19.

Cytotoxicity assay: Target cells: 10$^4$ of AGS, AGS-A2, BGC-823, BGC-823-A2 cells were inoculated into 96-well plates, respectively; Effector cells: NK92 and CAR NK92 cells were added at an effector-to-target ratio of 6:1, 3:1 or 1.5:1; 5 duplicate wells were set for each group, and the average of 5 replicate wells was taken. The detection time was 4h. Each experimental group and each control group are as follows:

Each experimental group: each target cell+above effector cells; Control group 1: maximum release of LDH from target cells; Control group 2: spontaneous release of LDH from target cells; and Control group 3: spontaneous release of LDH from effector cells.

Detection method: CytoTox 96 non-radioactive cytotoxicity test kit (Promega) was used, in particular, referring to instructions of CytoTox 96 Non-Radioactive Cytotoxicity Assay Kit. The calculation formula for cytotoxicity is:

Cytotoxicity %=(Experimental group−Control group 2−Control group 3)/(Control group 1−Control group 2)*100%

Figure 20:
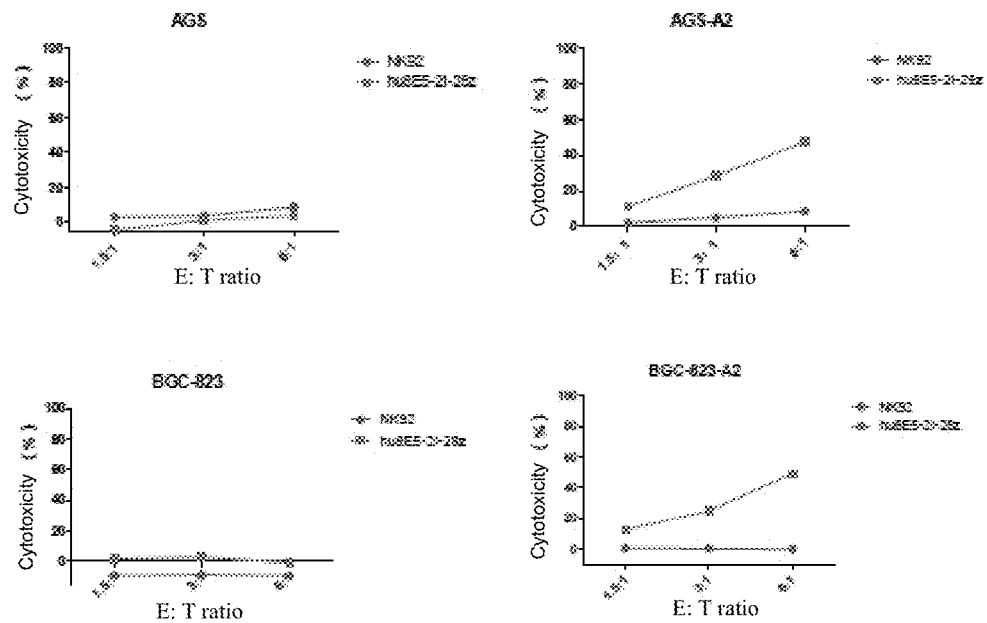
FIG. 20 is a graph showing the cytotoxicity of hu8E5-2I-28Z CAR-NK92.
Figure 21:
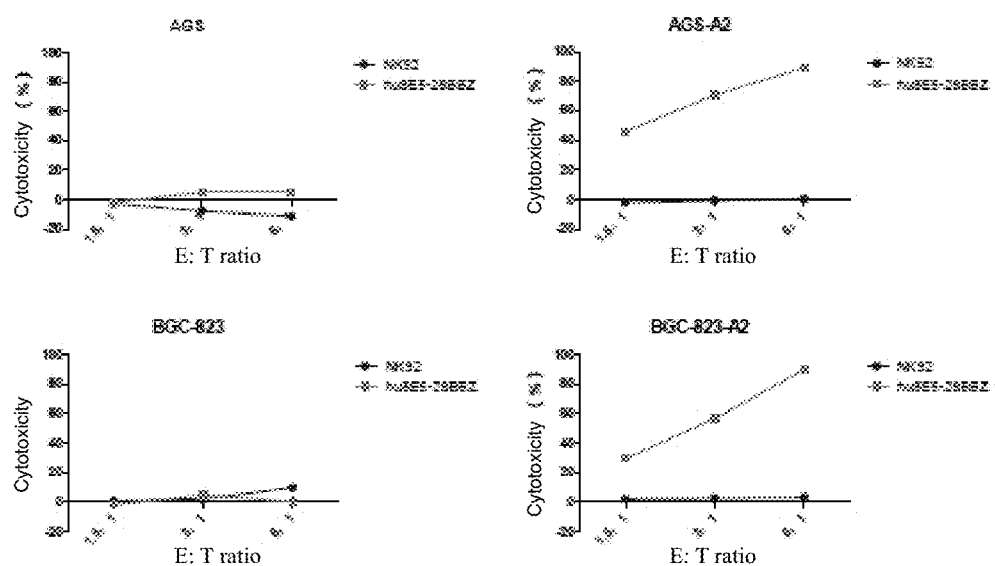
FIG. 21 is a graph showing the cytotoxicity of hu8E5-28BBZ CAR-NK92.

The results are shown in FIGS. 20 and 21, in which hu8E5-2I-28Z is hu8E5-2I-28Z CAR-NK92 cells and hu8E5-28BBZ is hu8E5-28BBZ CAR-NK92 cells. The results showed that hu8E5 CAR-NK92 cells had significant in vitro killing activities against cells overexpressing CLDN18A2 and almost no killing toxicities against CLDN18A2-negative cells.

TABLE 7

Sequences used herein

| SEQ ID: | Sequence |
|---|---|
| 1 | divmtqspssltvtagekvtmsckssqsllnsgnqknyltwyqq kpgqppklliywastresgvpdrftgsgsgtdftltissvqaed lavyycqndysypltfgagtklelkr |
| 2 | GACATTGTGATGACACAGTCTCCATCCTCCCTGACTGTGACAGC AGGAGAGAAGGTCACTATGAGCTGCAAGTCCAGTCAGAGTCTGT TAAACAGTGGAAATCAAAAGAACTACTTGACCTGGTACCAGCAG AAACCAGGGCAGCCTCCTAAACTGTTGATCTACTGGGCATCCAC TAGGGAATCTGGGGTCCCTGATCGCTTCACAGGCAGTGGATCTG GAACAGATTTCACTCTCACCATCAGCAGTGTGCAGGCTGAAGAC CTGGCAGTTTATTACTGTCAGAATGATTATAGTTATCCGCTCAC GTTCGGTGCTGGGACCAAGCTGGAGCTGAAACGG |
| 3 | qvqlqqsgaelarpgasvkmsckasgytftsytmhwvkqrpgqg lewigyinpssgytnynqkfkdkatltadkssstaymqlsslts edsavyycariyygnsfaywgqgttvtvss |
| 4 | CAGGTCCAGCTGCAGCAGTCTGGGGCTGAACTGGCAAGACCTGG GGCCTCAGTGAAGATGTCCTGCAAGGCTTCTGGCTACACCTTTA CTAGCTACACGATGCACTGGGTAAAACAGAGGCCTGGACAGGGT CTGGAATGGATTGGATACATTAATCCTAGCAGTGGTTATACTAA TTACAATCAGAAGTTCAAGGACAAGGCCACATTGACTGCAGACA AATCCTCCAGCACAGCCTACATGCAACTGAGCAGCCTGACATCT GAGGACTCTGCAGTCTATTACTGTGCCAAGAATCTACTATGGTAA CTCGTTTGCTTACTGGGGCCAAGGGACCACGGTCACCGTCTCCT CA |
| 5 | QIVLTQSPAIMSASPGEKVTMTCSASSSISYMHWYQQKPGTSPK RWIYDTSKLASGVPARFSGSGSGTSYSLTISSMEAEDAATYYCH QRSSYPYTFGGGTKLEIKR |
| 6 | CAAATTGTTCTCACCCAGTCTCCAGCAATCATGTCTGCATCTCC AGGGGAGAAGGTCACCATGACCTGCAGTGCCAGCTCAAGTATAA GTTACATGCACTGGTACCAGCAGAAGCCAGGCACCTCCCCCAAA AGATGGATTTATGACACATCCAAACTGGCTTCTGGAGTCCCTGC TCGCTTCAGTGGCAGTGGGTCTGGGACCTCTTATTCTCTCACAA TCAGCAGCATGGAGGCTGAAGATGCTGCCACTTATTACTGCCAT CAGCGGAGTAGTTACCCGTACACGTTCGGAGGGGGGACCAAGCT GGAAATAAAACGG |
| 7 | QVQLQQSGPELVKPGALVKISCKASGYTFTSYDINWVKQRPGQG LEWIGWIYPGDGSTKYNEKFKGKATLTADKSSSTAYMQLSSLTS ENSAVYFCARGGYRYDEAMDYWGQGTTVTVSS |
| 8 | CAGGTTCAGCTGCAGCAGTCTGGACCTGAGCTGGTGAAGCCTGG GGCTTTAGTGAAGATATCCTGCAAGGCTTCTGGTTACACCTTCA CAAGCTACGATATAAACTGGGTGAAGCAGAGGCCTGGACAGGGA CTTGAGTGGATTGGATGGATTTATCCTGGAGATGGTAGTACTAA GTACAATGAGAAATTCAAGGGCAAGGCCACACTGACTGCAGACA AATCCTCCAGCACAGCCTACATGCAGCTCAGCAGCCTGACTTCT GAGAACTCTGCAGTCTATTTCTGTGCAAGAGGGGGCTATAGGTA CGACGAGGCTATGGACTACTGGGGTCAAGGGACCACGGTCACCG TCTCCTCA |
| 9 | divmtqspsslsysagekvtmsckssqsllnsgnqknylawyqq kpgqppklliygastresgvpdrftgsgsgtdftltissvqaed lavyycqndhsypltfgagtklelkr |
| 10 | GACATTGTGATGACACAGTCTCCATCCTCCCTGAGTGTGTCAGC AGGAGAGAAGGTCACTATGAGCTGCAAGTCCAGTCAGAGTCTGT TAAACAGTGGAAATCAAAAGAACTACTTGGCCTGGTACCAGCAG AAACCAGGGCAGCCTCCTAAACTGTTGATCTACGGGGCATCCAC TAGGGAATCTGGGGTCCCTGATCGCTTCACAGGCAGTGGATCTG GAACCGATTTCACTCTTACCATCAGCAGTGTGCAGGCTGAAGAC CTGGCAGTTTATTACTGTCAGAATGATCATAGTTATCCGCTCAC GTTCGGTGCTGGGACCAAGCTGGAGCTGAAACGG |
| 11 | qiqlvqsgpelkkpgetvkisckasgytftnygmnwvkqapgkg lkwmgwintntgeptyaeefkgrfafsletsastaylqinnlkn edtatyfcarfsygnsfaywgqgttvtvss |

TABLE 7-continued

Sequences used herein

| SEQ ID: | Sequence |
|---|---|
| 12 | CAGATCCAGTTGGTGCAGTCTGGACCTGAGCTGAAGAAGCCTGG AGAGACAGTCAAGATCTCCTGCAAGGCTTCTGGGTATACCTTCA CAAACTATGGAATGAACTGGGTGAAGCAGGCTCCAGGAAAGGGT TTAAAGTGGATGGGCTGGATAAACACCAACACTGGAGAGCCAAC ATATGCTGAAGAGTTCAAGGGACGGTTTGCCTTCTCTTTGGAAA CCTCTGCCAGCACTGCCTATTTGCAGATCAACAACCTCAAAAAT GAGGACACGGCTACATATTTCTGTGCTAGATTCTCTTATGGTAA CTCCTTTGCTTACTGGGGCCAAGGGACCACGGTCACCGTCTCCT CA |
| 13 | divmtqspssltvtpgekvtmtckssqslfnsgnqknyltwyqq rpgqppkmliywastresgvpdrftgsgsgtdftltissvqaed lavfycpaysfpytfgggtkleikr |
| 14 | GACATTGTGATGACACAGTCTCCATCCTCCCTGACTGTGACACC AGGAGAGAAGGTCACTATGACCTGCAAGTCCAGTCAGAGTTTGT TTAATAGTGGAAATCAAAAGAACTACTTGACCTGGTACCAACAG AGACCTGGCCAGCCCCCTAAAATGTTGATCTACTGGGCATCCAC TAGGGAATCTGGGGTCCCTGATCGCTTCACAGGCAGTGGATCTG GAACAGATTTCACTCTCACCATCAGCAGTGTGCAGGCTGAAGAC CTGGCAGTTTTTTACTGTCAGAATGCTTATAGTTTTCCGTACAC GTTCGGAGGGGGGACCAAGCTGGAAATAAAACGG |
| 15 | dvqlqesgpdlvkpsqslsltctvtgysitsgynwhwirqfpgn kmewmgyihytgstnynpslrsrisitrdtsknqfflqlnsvtt ddtatyyctriyngnsfpywgqgtsvtvss |
| 16 | GATGTGCAACTTCAGGAGTCAGGACCTGACCTGGTGAAACCTTC TCAGTCACTTTCACTCACCTGCACTGTCACTGGCTACTCCATCA CCAGTGGTTATAACTGGCACTGGATCCGGCAGTTTCCAGGAAAC AAAATGGAATGGATGGGCTACATAACACTACACTGGTAGCACTAA TTACAACCCATCTCTCAGAAGTCGAATCTCTATCACTCGAGACA CATCCAAGAACCAGTTCTTCCTGCAGTTGAATTCTGTGACCACT GATGACACAGCCACATATTACTGTACAAGAATCTACAATGGTAA CTCTTTTCCTTACTGGGGCCAAGGAACCTCAGTCACCGTCTCCT CA |
| 17 | qvqlqqsgaelarpgasvkmsckasgytftsytmhwvkqrpgqg lewigyidpssgytnynqkfkdkatltadksssstaymqlsslts edsavyycariyygnsfaywgqgttvtvss |
| 18 | CAGGTCCAGCTGCAGCAGTCTGGGGCTGAACTGGCAAGACCTGG GGCCTCAGTGAAGATGTCCTGCAAGGCTTCTGGCTACACCTTTA CTAGCTACACGATGCACTGGGTAAAACAGAGGCCTGGACAGGGT CTGGAATGGATTGGATACATTGACCCTAGCAGTGGTTATACTAA TTACAATCAGAAGTTCAAGGACAAGGCCACATTGACTGCAGACA AATCCTCCAGCACAGCCTACATGCAACTGAGCAGCCTGACATCT GAGGACTCTGCAGTCTATTACTGTGCAAGAATCTACTATGGTAA CTCGTTTGCTTACTGGGGCCAAGGGACCACGGTCACCGTCTCCT CA |
| 19 | qvqlqqsgaelarpgasvkmsckasgytftsytmhwvkqrpgqg lewigyinpasgytnynqkfkdkatltadksssstaymqlssits edsavyycariyygnsfaywgqgttvtvss |
| 20 | CAGGTCCAGCTGCAGCAGTCTGGGGCTGAACTGGCAAGACCTGG GGCCTCAGTGAAGATGTCCTGCAAGGCTTCTGGCTACACCTTTA CTAGCTACACGATGCACTGGGTAAAACAGAGGCCTGGACAGGGT CTGGAATGGATTGGATACATTAATCCTGCCAGTGGTTATACTAA TTACAATCAGAAGTTCAAGGACAAGGCCACATTGACTGCAGACA AATCCTCCAGCACAGCCTACATGCAACTGAGCAGCCTGACATCT GAGGACTCTGCAGTCTATTACTGTGCAAGAATCTACTATGGTAA CTCGTTTGCTTACTGGGGCCAAGGGACCACGGTCACCGTCTCCT CA |
| 21 | divmtqspdslavslgeratinckssqsllnsgnqknyltwyqq kpgqppklliywastresgvpdrfsgsgsgtdftltisslqaed vavyycqndysypltfgggtkveikr |
| 22 | GACATCGTGATGACCCAGAGCCCCGACAGCCTGGCCGTGAGCCT GGGCGAGCGGGCCACCATCAACTGCAAGAGCAGCCAGAGCCTGC TGAACAGCGGCAACCAGAAGAACTACCTGACCTGGTACCAGCAG AAGCCCGGCCAGCCCCCCAAGCTGCTGATCTACTGGGCCAGCAC CCGGGAGAGCGGCGTGCCCGACCGGTTCAGCGGCAGCGGCAGCG GCACCGACTTCACCCTGACCATCAGCAGCCTGCAGGCCGAGGAC GTGGCCGTGTACTACTGCCAGAACGACTACAGCTACCCCCTGAC CTTCGGCGGCGGCACCAAGGTGGAGATCAAGCGG |
| 23 | qvqlvqsgaevkkpgasvkvsckasgytftsytmhwvrqapgqg lewmgyinpasgytnynqkfkdrvtmtrdtststaymelsslrs edtavyycariyygnsfaywgqgtivtvss |
| 24 | CAGGTGCAGCTGGTGCAGAGCGGCGCCGAGGTGAAGAAGCCCGG CGCCAGCGTGAAGGTGAGCTGCAAGGCCAGCGGCTACACCTTCA CCAGCTACACCATGCACTGGGTGCGGCAGGCCCCCGGCCAGGGC CTGGAGTGGATGGGCTACATCAACCCCGCCAGCGGCTACACCAA CTACAACCAGAAGTTCAAGGACCGGGTGACCATGACCCGGGACA CCAGCACCAGCACCGCCTACATGGAGCTGAGCAGCCTGCGGAGC GAGGACACCGCCGTGTACTACTGCGCCCGGATCTACTACGGCAA CAGCTTCGCCTACTGGGGCCAGGGCACCCTGGTGACCGTGAGCA GC |
| 25 | divmtqspdslayslgeratinckssqslfnsgnqknyltwyqq kpgqppklliywastresgvpdrfsgsgsgtdifitisslqaed vavyycqnaysfpytfgggtkleikr |
| 26 | GACATCGTGATGACCCAGAGCCCCGACAGCCTGGCCGTGAGCCT GGGCGAGCGGGCCACCATCAACTGCAAGAGCAGCCAGAGCCTGT TCAACAGCGGCAACCAGAAGAACTACCTGACCTGGTACCAGCAG AAGCCCGGCCAGCCCCCCAAGCTGCTGATCTACTGGGCCAGCAC CCGGGAGAGCGGCGTGCCCGACCGGTTCAGCGGCAGCGGCAGCG GCACCGACTTCACCCTGACCATCAGCAGCCTGCAGGCCGAGGAC GTGGCCGTGTACTACTGCCAGAACGACTACAGCTTCCCCCTACAC CTTCGGCGGCGGCACCAAGGTGGAGATCAAGCGG |
| 27 | qvqlqesgpglvkpsqtlsltctvsggsissgynwhwirqppgk glewigyihytgstnynpalrsrvtisvdtsknqfslklssvta adtavyycariyngnsfpywgqgttvtvss |
| 28 | CAGGTGCAGCTGCAGGAGAGCGGCCCCGGCCTGGTGAAGCCCAG CCAGACCCTGAGCCTGACCTGCACCGTGAGCGGCGGCAGCATCA GCAGCGGCTACAACTGGCACTGGATCCGGCAGCCCCCCGGCAAG GGCCTGGAGTGGATCGGCTACATCCACTACACCGGCAGCACCAA CTACAACCCCGCCCTGCGGAGCCGGGTGACCATCAGCGTGGACA CCAGCAAGAACCAGTTCAGCCTGAAGCTGAGCAGCGTGACCGCC GCCGACACCGCCGTGTACTACTGCGCCCGGATCTACAACGGCAA CAGCTTCCCCTACTGGGGCCAGGGCACCACCGTGACCGTGAGCA GC |
| 29 | QVQLQESGPGLIKPSQTLSLTCTVSGGSISSGYNWHWIRQPPGK GLEWIGYIHYTGSTNYNPALRSRVTISVDTSKNQFSLKLSSVTA ADTAIYYCARIYNGNSFPYWGQGTTVTVSS |
| 30 | CAGGTGCAGCTGCAGGAGAGCGGCCCCGGCCTGATCAAGCCCAG CCAGACCCTGAGCCTGACCTGCACCGTGAGCGGCGGCAGCATCA GCAGCGGCTACAACTGGCACTGGATCCGGCAGCCCCCCGGCAAG GGCCTGGAGTGGATCGGCTACATCCACTACACCGGCAGCACCAA CTACAACCCCGCCCTGCGGAGCCGGGTGACCATCAGCGTGGACA CCAGCAAGAACCAGTTCAGCCTGAAGCTGAGCAGCGTGACCGCC GCCGACACCGCCATCTACTACTGCGCCCGGATCTACAACGGCAA CAGCTTCCCCTACTGGGGCCAGGGCACCACCGTGACCGTGAGCA GC |
| 31 | SER TYR THR MET HIS |
| 32 | TYR ILE ASN PRO SER SER GLY TYR THR ASN TYR ASN GLN LYS PHE LYS ASP |
| 33 | ILE TYR TYR GLY ASN SER PHE ALA TYR |
| 34 | LYS SER SER GLN SER LEU LEU ASN SER GLY ASN GLN LYS ASN TYR LEU THR |
| 35 | TRP ALA SER THR ARG GLU SER |
| 36 | GLN ASN ASP TYR SER TYR PRO LEU THR |
| 37 | SYDIN |

TABLE 7-continued

Sequences used herein

| SEQ ID: | Sequence |
|---|---|
| 38 | WIYPGDGSTKYNEKFKG |
| 39 | GGYRYDEAMDY |
| 40 | SASSSISYMH |
| 41 | DTSKLAS |
| 42 | HQRSSYPYT |
| 43 | ASN TYR GLY MET ASN |
| 44 | TRP ILE ASN THR ASN THR GLY GLU PRO THR TYR ALA GLU GLU PHE LYS GLY |
| 45 | PHE SER TYR GLY ASN SER PHE ALA TYR |
| 46 | LYS SER SER GLN SER LEU LEU ASN SER GLY ASN GLN LYS ASN TYR LEU ALA |
| 47 | GLY ALA SER THR ARG GLU SER |
| 48 | GLN ASN ASP HIS SER TYR PRO LEU THR |
| 49 | SER GLY TYR ASN TRP HIS |
| 50 | TYR ILE HIS TYR THR GLY SER THR ASN TYR ASN PRO SER LEU ARG SER |
| 51 | ILE TYR ASN GLY ASN SER PHE PRO TYR |
| 52 | LYS SER SER GLN SER LEU PHE ASN SER GLY ASN GLN LYS ASN TYR LEU THR |
| 53 | TRP ALA SER THR ARG GLU SER |
| 54 | GLN ASN ALA TYR SER PHE PRO TYR THR |
| 55 | MAVTACQGLGFVVSLIGIAGIIAATCMDQWSTQDLYNNPVTAVF NYQGLWRSCVRESSGFTECRGYFTLLGLPAMLQAVRALMIVGIV LGAIGLLVSIFALKCIRIGSMEDSAKANMTLTSGIMFIVSGLCA IAGVSVFANMLVTNFWMSTANMYTGMGGMVQTVQTRYTFGAALF VGWVAGGLTLIGGVMMCIACRGLAPEETNYKAVSYHASGHSVAY KPGGFKASTGFGSNTKNKKIYDGGARTEDEVQSYPSKHDYV |
| 56 | atggccgtgactgcctgtcagggcttggggttcgtggtttcact gattgggattgcgggcatcattgctgccacctgcatggaccagt ggagcacccaagacttgtacaacaacccgtaacagctgttttc aactaccaggggctgtggcgctcctgtgtccgagagctctgg cttcaccgagtgccggggctacttcacccttcgggggctgccag ccatgctgcaggcagtgcgagccctgatgatcgtaggcatcgtc ctgggtgccattggcctcctggtatccatctagccctgaaatgc atccgcattggcagcatggaggactctgccaaagccaacatgac actgacctccgggatcatgttcattgtctcaggtcttgtgcaa ttgctggagtgtctgtgtttgccaacatgctggtgactaacttc tggatgtccacagctaacatgtacaccggcatgggtgggatggt gcagactgttcagaccaggtacacatttggtgcggctctgttcg tgggctgggtcgctggaggcctcacactaattggggtgtgatg atgtgcatcgcctgccggggcctggcaccagaagaaaccaacta caaagccgtttcttatcatgcctcaggccacagtgttgcctaca agcctggaggcttcaaggccagcactggctttgggtccaacacc aaaaacaagaagatatacgatggaggtgcccgcacagaggacga ggtacaatcttatccttccaagcacgactatgtgtaa |
| 57 | MSTTTCQVVAFLLSILGLAGCIAATGMDMWSTQDLYDNPVTSVF QYEGLWRSCVRQSSGFTECRPYFTILGLPAMLQAVRALMIVGIV LGAIGLLVSIFALKCIRIGSMEDSAKANMTLTSGIMFIVSGLCA IAGVSVFANMLVTNFWMSTANMYTGMGGMVQTVQTRYTFGAALF VGWVAGGLTLIGGVMMCIACRGLAPEETNYKAVSYHASGHSVAY KPGGFKASTGFGSNTKNKKIYDGGARTEDEVQSYPSKHDYV |
| 58 | atgtccaccaccacatgccaagtggtggcgttcctcctgtccat cctggggctggccggctgcatcgcggccaccgggatggacatgt ggagcacccaggacctgtacgacaacccctcacctccgtgttc cagtacgaagggctctggaggagctgcgtgaggcagagttcagg cttcaccgaatgcaggccctatttcaccatcctgggacttccag ccatgctgcaggcagtgcgagccctgatgatcgtaggcatcgtc ctgggtgccattggcctcctggtatccatctttgccctgaaatg catccgcattggcagcatggaggactctgccaaagccaacatga cactgacctccgggatcatgttcattgtctcaggtattgtgcaa ttgctggagtgtctgtgtttgccaacatgctggtgactaacttc tggatgtccacagctaacatgtacaccggcatgggtgggatggt gcagactgttcagaccaggtacacatttggtgcggctctgttcg tgggctgggtcgctggaggcctcacactaattggggtgtgatg atgtgcatcgcctgccggggcctggcaccagaagaaaccaacta caaagccgtttcttatcatgcctcaggccacagtgttgcctaca agcctggaggcttcaaggccagcactggctttgggtccaacacc aaaaacaagaagatatacgatggaggtgcccgcacagaggacga ggtacaatcttatccttccaagcacgactatgtgtaa |
| 59 | qvqlvqsgaevkkpgasvkvsckasgytftsytmhwvrqapgqg lewmgyinpasgytnynqkfkdrvtmtrdtststaymelssrls edtavyycariyygnsfaywgqgtlvtvssastkgpsvfplaps skstsggtaalgclvkdyfpepvtvswnsgaltsgvhtfpavlq ssglyslssvvtvpssslgtqtyicnvnhkpsntkvdkkvepks cdkthtcppcpapellggpsvflfppkpkdtlmisrtpevtcvv vdvshedpevkfnwyvdgvevhnakttkpreeqynstyrvvsvlt vlhqdwlngkeykckvsnkalpapiektiskakgqprepqvytl ppsrdeltknqvsltclvkgfypsdiavewesngqpennykttp pvldsdgsfflyskltvdksrwqqgnvfscsvmhealhnhytqk slslspgk |
| 60 | caggtgcagctggtgcagagcggcgccgaggtgaagaagcccgg cgccagcgtgaaggtgagctgcaaggccagcggctacaccttca ccagctacaccatgcactgggtgcggcaggcccccggccagggc ctggagtggatgggctacatcaaccccgccagcggctacaccaa ctacaaccagaagttcaaggaccgggtgaccatgacccgggaca ccagcaccagcacctacatggagctgagcagcctgcggagc gaggacaccgccgtgtactactgcgcccggatctactacggcaa cagcttcgcctactggggccagggcaccctggtgaccgtgagca gcgctagcaccaaggcccatcggtcttcccctggcacccctcc tccaagcaccctctggggcacagcgccctgggctgcctggt caaggactacttccccgaaccggtgacggtgtcgtggaactcag gcgccctgaccagcggcgtgcacaccttccgggctgtcctacag tcctcaggactctactccctcagcagcgtggtgaccgtgccctc cagcagcttgggcacccagacctacatctgcaacgtgaatcaca agcccagcaacaccaaggtggacaagaaagttgagcccaaatct tgtgacaaaactcacacatgcccaccgtgcccagcacctgaact cctggggggaccgtcagtcttcctcttccccccaaaacccaagg acaccctcatgatctcccggacccctgaggtcacatgcgtggtg gtggacgtgagccacgaagaccctgaggtcaagttcaactggta cgtggacggcgtggaggtgcataatgccaagacaaagccgcggg aggagcagtacaacagcacgtaccgtgtggtcagcgtcctcacc gtcctgcaccaggactggctgaatggcaaggagtacaagtgcaa ggtctccaacaaagccctcccagccccatcgagaaaaccatct ccaaagccaaagggcagccccgagaaccacaggtgtacaccctg cccccatcccgggatgagctgaccaagaaccaggtcagcctgac ctgcctggtcaaaggcttctatcccagcgacatcgccgtggagt gggagagcaatgggcagccggagaacaactacaagaccacgcct cccgtgctggactccgacggctccttcttcctctatagcaagct caccgtggacaagagcaggtggcagcaggggaacgtcttctcat gctccgtgatgcatgaggctctgcacaaccactacacgcagaag agcctctccctgtctccgggtaaa |
| 61 | divmtqspdslavslgeratinckssqsllnsgnqknyltwyqq kpgqppkllliywastresgvpdrfsgsgsgtdftltisslqaed vavyycqndysypltfggqtkveikrtvaapsvfifppsdeqlk sgtasvvcllnnfypreakvqwkvdnalqsgnsqesvteqdskd styslssstltlskadyekhkvyacevthqglsspvtksfnrgec |
| 62 | gacatcgtgatgacccagagccccgacagcctggccgtgagcct gggcgagcgggccaccatcaactgcaagagcagccagagcctgc tgaacagcggcaaccagaagaactacctgacctggtaccagcag aagcccggccagccccccaagctgctgatctactgggccagcac ccgggagagcggcgtgcccgaccggttcagcggcagcggcagcg gcaccgacttcacccttgaccatcagcagcctgcaggccgaggac gtggccgtgtactactgccagaacgactacagctaccccctgac cttcggcggcgggaccaaggtggagatcaagcggacggtggctg caccatctgtcttcatcttcccgccatctgatgagcagttgaaa tctggaactgcctctgttgtgtgcctgctgaataacttctatcc |

TABLE 7-continued

Sequences used herein

| SEQ ID: | Sequence |
|---|---|
|  | cagagaggccaaagtacagtggaaggtggataacgccctccaat cgggtaactcccaggagagtgtcacagagcaggacagcaaggac agcacctacagcctcagcagcacccctgacgctgagcaaagcaga ctacgagaaacacaaagtctacgcctgcgaagtcacccatcagg gcctgagctcgcccgtcacaaagagcttcaacaggggagagtgt |
| 63 | Qvqlqesgpglikpsqtlsltctvsggsissgynwhwirqppgk glewigyihytgstnynpalrsrvtisvdtsknqfslklssvta adtaiyycariyngnsfpywgqgttvtvssastkgpsvfplaps skstsggtaalgclvkdyfpepvtvswnsgaltsgvhtfpavlq ssglyslssvvtvpssslgtqtyicnvnhkpsntkvdkkvepks cdkthtcppcpapellggpsvflfppkpkdtlmisrtpevtcvv vdvshedpevkfnwyvdgvevhnakttkpreeqynstyrvvsylt vlhqdwlngkeykckvsnkalpapiektiskakgqprepqvytl ppsrdeltknqvsltclvkgfypsdiavewesngqpennykttp pvldsdgsfflysklvdksrwqqgnvfscsvmhealhnhytqk slslspgk |
| 64 | caggtgcagctgcaggagagcggccccggcctgatcaagcccag ccagaccctgagcctgacctgcaccgtgagcggcggcagcatca gcagcggctacaactggcactggatccgcagccccccggcaag ggcctggagtggatcggctacatccactacaccggcagcaccaa ctacaaccccgccctgcggagccgggtgaccatcagcgtggaca ccagcaagaaccagttcagcctgaagctgagcagcgtgaccgcc gccgacaccgccatctactactgcgcccggatctacaacggcaa cagcttccccactggggcagggcaccaccgtgaccgtgagca gcgctagcaccaaaggccatcggtcttcccctggcaccctcc tccaagagcacctctggggcacagcggccctgggctgcctggt caaggactacttccccgaaccggtgacggtgtcgtggaactgg gcgccctgaccagcggcgtgcacacctcccggctgtcctacag tcctcaggactctactcctcagcagcgtggtgaccgtgccctc cagcagcttgggcacccagacctacatctgcaacgtgaatcaca gcccagcaacaccaaggtggacaagaaagttgagcccaaatct tgtgacaaaactcacacatgcccaccgtgcccagcacctgaact cctggggggaccgtcagtcttcctcttccccccaaaacccaagg acaccctcatgatctcccggacccctgaggtcacatgcgtggtg gtggacgtgagccacgaagacccgaggtcaagttcaactggta cgtggacggcgtggaggtgcataatgccaagacaaagccgcgg aggagcagtacaacagcacgtaccgtgtggtcagcgtcctcacc gtcctgcaccaggactggctgaatggcaaggagtacaagtgcaa ggtctccaacaaagccctcccagcccccatcgagaaaaccatct ccaaagccaaagggcagccccgagaaccacaggtgtacaccctg cccccatcccgggatgagctgaccaagaaccaggtcagcctgac ctgcctggtcaaaggcttctatcccagcgacatcgccgtggagt gggagagcaatgggcagccggagaacaactacaagaccacgcct cccgtgctggactccgacggctccttcttcctctatagcaagct caccgtggacaagagcaggtggcagcaggggaacgtcttctcat gctccgtgatgcatgaggctctgcacaaccactacacgcagaag agcctctccctgtctccgggtaaa |
| 65 | divmtqspdslavslgeratinckssqslfnsgnqknyltwyqq kpgqppklliywastresgvpdrfsgsgsgtdftltisslqaed vavyycqnaysfpytfgggtkleikrtvaapsvfifppsdeqlk sgtasvvcllnnfypreakvqwkvdnalqsgnsqesvteqdskd styslsstltlskadyekhkvyacevthqglsspvtksfnrgec |
| 66 | gacatcgtgatgacccagagccccgacagcctggccgtgagcct gggcgagcgggccaccatcaactgcaagagcagccagagcctgt tcaacagcggcaaccagaagaactacctgacctggtaccagcag aagcccggccagccccccaagctgctgatctactgggccagcac ccgggagagcggcgtgcccgaccggttcagcggcagcggcagcg gcaccgacttcaccctgaccatcagcagcctgcaggccgaggac gtggccgtgtactactgccagaacgcctacagcttcccctacac cttcggcggcggcaccaagctggagatcaagcggacggtggctg caccatctgtcttcatcttcccgccatctgatgagcagttgaaa tctggaactgcctctgttgtgtgcctgctgaataacttctatcc cagagaggccaaagtacagtggaaggtggataacgccctccaat cgggtaactcccaggagagtgtcacagagcaggacagcaaggac agcacctacagcctcagcagcacccctgacgctgagcaaagcaga ctacgagaaacacaaagtctacgcctgcgaagtcacccatcagg gcctgagctcgcccgtcacaaagagcttcaacaggggagagtgt |
| 67 | qvqlqesgpglvkpsqtlsltctvsggsissgynwhwirqppgk glewigyihytgstnynpalrsrvtisvdtsknqfslklssvta adtaiyycariyngnsfpywgqgttvtvssastkgpsvfplaps skstsggtaalgclvkdyfpepvtvswnsgaltsgvhtfpavlq ssglyslssvvtvpssslgtqtyicnvnhkpsntkvdkkvepks cdkthtcppcpapellggpsvflfppkpkdtlmisrtpevtcvv vdvshedpevkfnwyvdgvevhnakttkpreeqynstyrvvsylt vlhqdwlngkeykckvsnkalpapiektiskakgqprepqvytl ppsrdeltknqvsltclvkgfypsdiavewesngqpennykttp pvldsdgsfflysklvdksrwqqgnvfscsvmhealhnhytqk slslspgk |
| 68 | caggtgcagctgcaggagagcggccccggcctgatcaagcccag ccagaccctgagcctgacctgcaccgtgagcggcggcagcatca gcagcggctacaactggcactggatccgcagccccccggcaag ggcctggagtggatcggctacatccactacaccggcagcaccaa ctacaaccccgccctgcggagccgggtgaccatcagcgtggaca ccagcaagaaccagttcagcctgaagctgagcagcgtgaccgcc gccgacaccgccatctactactgcgcccggatctacaacggcaa cagcttccccactggggcagggcaccaccgtgaccgtgagca gcgctagcaccaaaggccatcggtcttcccctggcaccctcc tccaagagcacctctggggcacagcggccctgggctgcctggt caaggactacttccccgaaccggtgacggtgtcgtggaactgg gcgccctgaccagcggcgtgcacacctcccggctgtcctacag tcctcaggactctactcctcagcagcgtggtgaccgtgccctc cagcagcttgggcacccagacctacatctgcaacgtgaatcaca gcccagcaacaccaaggtggacaagaaagttgagcccaaatct tgtgacaaaactcacacatgcccaccgtgcccagcacctgaact cctggggggaccgtcagtcttcctcttccccccaaaacccaagg acaccctcatgatctcccggacccctgaggtcacatgcgtggtg gtggacgtgagccacgaagacccgaggtcaagttcaactggta cgtggacggcgtggaggtgcataatgccaagacaaagccgcgg aggagcagtacaacagcacgtaccgtgtggtcagcgtcctcacc gtcctgcaccaggactggctgaatggcaaggagtacaagtgcaa ggtctccaacaaagccctcccagcccccatcgagaaaaccatct ccaaagccaaagggcagccccgagaaccacaggtgtacaccctg cccccatcccgggatgagctgaccaagaaccaggtcagcctgac ctgcctggtcaaaggcttctatcccagcgacatcgccgtggagt gggagagcaatgggcagccggagaacaactacaagaccacgcct cccgtgctggactccgacggctccttcttcctctatagcaagct caccgtggacaagagcaggtggcagcaggggaacgtcttctcat gctccgtgatgcatgaggctctgcacaaccactacacgcagaag agcctctccctgtctccgggtaaa |
| 69 | malpvtalllplallhaarp |
| 70 | atggccttaccagtgaccgccttgctcctgccgctggccttgct gctccacgccgccaggccg |
| 71 | Tttpaprpptpaptiasqplslrpeacrpaaggavhtrgldfac d |
| 72 | accacgacgccagcgccgcgaccaccaacaccggcgcccaccat cgcgtcgcagcccctgtccctgcgcccagaggcgtgccggcag cggcgggggcgcagtgcacacgagggggctggacttcgcctgt gat |
| 73 | Fwvlvvvggvlacysllvtvafiifwv |
| 74 | ttttgggtgctggtggtggttggtggagtcctggcttgctatag cttgctagtaacagtggcctttattattttctgggtg |
| 75 | Rskrsrllhsdymnmtprrrpgptrkhyqpyapprdfaayrs |
| 76 | aggagtaagaggagcaggctcctgcacagtgactacatgaacat gactccccgccgccccgggccaacccgcaagcattaccagccct atgccccaccacgcgacttcgcagcctatcgctcc |
| 77 | rvkfsrsadapayqqgqnqlynelnlgrreeydvldkrrgrdpe mggkpqrrknpqeglynelqkdkmaeayseigmkgerrrgkghd glyqglstatkdtydalhmqalppr |
| 78 | agagtgaagttcagcaggagcgcagacgccccgcgtaccagca gggccagaaccagctctataacgagctcaatctaggacgaagag aggagtacgatgttttggacaagagacgtggccgggaccctgag atgggggaaagccgcagaaggaagaaccctcaggaaggcct gtacaatgaactgcagaaagataagatggcggaggcctacagtg agattgggatgaaaggcgagcgccggagggcaagggcacgat |

TABLE 7-continued

Sequences used herein

| SEQ ID: | Sequence |
|---|---|
|  | ggcctttaccagggtctcagtacagccaccaaggacacctacga cgcccttcacatgcaggccctgccccctcgc |
| 79 | Iyiwaplagtcgvlllslvit |
| 80 | Atctacatctgggcgcccttggccgggacttgtggggtccttct cctgtcactggttatcacc |
| 81 | Krgrkkllyifkqpfmrpvqttqeedgcscrfpeeeeggcel |
| 82 | aaacggggcagaaagaaactcctgtatatattcaaacaaccatt tatgagaccagtacaaactactcaagaggaagatggctgtagct gccgatttccagaagaagaagaaggaggatgtgaactg |
| 83 | YIDPSSGYTNYNQKFKD |
| 84 | YINPASGYTNYNQKFKD |
| 85 | yihytgstnynpalrs |
| 86 | Divmtqspssltvtagekvtmscksssqsllnsgnqknyltwyqq kpgqppkllliywastresgvpdrftgsgsgtdftltissvqaed lavyycqndysypltfgagtklelkrtvaapsvfifppsdeqlk sgtasvvcllnnfypreakvqwkvdnalqsgnsqesvteqdskd styslsstltlskadyekhkvyacevthqglsspvtksfnrgec |
| 87 | Qiqlvqsgpelkkpgetvkisckasgytftnygmnwvkqapgkg lkwmgwintntgeptyaeefkgrfafsletsastayIqinnlkn edtatyfcarlgfgnamdywgqgtsvtvssastkgpsvfplaps skststggtaalgclvkdyfpepvtvswnsgaltsgvhtfpavlq ssglyslssvvtvpssslgtqtyicnvnhkpsntkvdkkvepks cdkthtcppcpapellggpsvflfppkpkdtlmisrtpevtcvv vdvshedpevkfnwyvdgvevhnaktkpreeqynstyrvvsvlt vlhqdwlngkeykckvsnkalpapiektiskakgqprepqvytl ppsrdeltknqvsltclvkgfypsdiavewesngqpennykttp pvldsdgsfflyskltvdksrwqqgnvfscsvmhealhnhytqk slslspgk |
| 88 | Divmtqspssltvtagekvtmscksssqsllnsgnqknyltwyqq kpgqppkllliywastresgvpdrftgsgsgtdftltissvqaed lavyycqndysypftfgsgtklelkrtvaapsvfifppsdeqlk sgtasvvcllnnfypreakvqwkvdnalqsgnsqesvteqdskd styslsstltlskadyekhkvyacevthqglsspvtksfnrgec |
| 89 | Qvqlqqpgaelvrpgasvklsckasgytftsywinwvkqrpgqg lewigniypsdsytynyqkfkdkatltvdkssstaymqlsspts edsavyyctrswrgnsfdywgqgttltvssastkgpsvfplaps skststggtaalgclvkdyfpepvtvswnsgaltsgvhtfpavlq ssglyslssvvtvpssslgtqtyicnvnhkpsntkvdkkvepks cdkthtcppcpapellggpsvflfppkpkdtlmisrtpevtcvv vdvshedpevkfnwyvdgvevhnaktkpreeqynstyrvvsvlt vlhqdwlngkeykckvsnkalpapiektiskakgqprepqvytl ppsrdeltknqvsltclvkgfypsdiavewesngqpennykttp pvldsdgsfflyskltvdksrwqqgnvfscsvmhealhnhytqk slslspgk |
| 90 | atggcctaccagtgaccgccttgctcctgccgctggccttgct gctccacgccgccaggccgcaggtgcagctgcaggagagcggcc ccggcctggtgaagccagccagaccctgagcgtgacctgcacc gtgagcggcggcagcatcagcagcggctacaactggcactggat ccggcagcccccggcaagggcctggagtggatcggctacatcc actacaccggcagcaccaactacaaccccgcctcgcggagccgg gtgaccatcagcgtggacaccagcaagaaccagttcagcctgaa gctgagcagcgtgaccgccgccgacaccgccgtgtactactgcg cccggatctacaacggcaacagcttcccctactggggccaggc accaccgtgaccgtgagcagcgctagcaccaagggtccatcggt cttccccctggcgccctgctccaggagcacctccgagagcaca gccgccctgggctgcctggtcaaggactacttccccgaaccggt gacggtgtcgtggaactcaggcgccctgaccagcggcgtgcaca ccttcccggctgtcctacagtcctcaggactctactccctcagc agcgtggtgaccgtgccctccagcagcttgggcacccagaccta catctgcaacgtgaatcacaagcccagcaacaccaaggtggaca agaaagttgagcccaaatcttgtgacaaaactcacacatgcccac cgtgcccagcacctgaactcctggggggaccgtcagtcttcctc ttccccccaaaacccaaggacaccctcatgatctcccggacccc tgaggtcacatgcgtggtggtggacgtgagccacgaagaccctg aggtcaagttcaactggtacgtggacggcgtggaggtgcataat gccaagacaaagccgcgggaggagcagtacaacagcacgtacc gtgtggtcagcgtcctcaccgtcctgcaccaggactggctgaat ggcaaggagtacaagtgcaaggtctccaacaaagccctcccagc ccccatcgagaaaaccatctccaaagccaaagggcagccccgag aaccacaggtgtacaccctgcccccatcccgggaggagatgacc aagaaccaggtcagcctgacctgcctggtcaaaggcttctatcc cagcgacatcgccgtggagtgggagagcaatgggcagccggaga acaactacaagaccacgcctcccgtgctggactccgacggctcc ttcttcctctatagcaagctcaccgtggacaagagcaggtggca gcaggggaacgtcttctcatgctccgtgatgcatgaggctctgc acaaccactacacgcagaagagcctctccctgtctcccgggaaa |
| 91 | atggcttaccagtgaccgccttgctcctgccgctggccttgct gctccacgccgccaggccgcaggtgcagctgcaggagagcggcc ccggcctgatcaagccagccagaccctgagcgtgacctgcacc gtgagcggcggcagcatcagcagcggctacaactggcactggat ccggcagcccccggcaagggcctggagtggatcggctacatcc actacaccggcagcaccaactacaaccccgcctcgcggagccgg gtgaccatcagcgtggacaccagcaagaaccagttcagcctgaa gctgagcagcgtgaccgccgccgacaccgccatctactactgcg cccggatctacaacggcaacagcttcccctactggggccaggc accaccgtgaccgtgagcagcgcgtggttcaggcggagg tggttctggcggtggcggatcggacatcgtgatgacccagagcc ccgacagcctggcgtgagcctgggcgagcggccaccatcaac tgcaagagcagcagagcctgttcaacagcggcaaccagaagaa ctacctgacctggtaccagcagaagccccagcccccaagc tgctgatctactgggcgagcacccgggagagcgtgcccgac cggttcagcggcagcggcagcggcaccgacttcacccctgaccat cagcagcctgcaggccgaggacgtggccgtgtactactgcaga caacgcctacagcttcccctacaccttcggcggcggcaccaacg gagatcaagcggaccacgacgccagcgccgcgaccaccaacacc ggcgccaccatcgcgtcgcagcccctgtccctgcgcccagagg cgtgccggccagcggcggggggcgcagtgcacacgaggggctg gacttcgcctgtgatttagggtgctggtggtggttggtggagtc ctggcttgctatagcttgctagtaacagtggcctttattatttt |

TABLE 7-continued

Sequences used herein

| SEQ ID: | Sequence |
|---|---|
| | ctgggtgaggagtaagaggagcaggctcctgcacagtgactaca |
| | tgaacatgactccccgccgccccgggccaacccgcaagcattac |
| | cagccctatgccccaccacgcgacttcgcagcctatcgctccag |
| | agtgaagttcagcaggagagcgacgccccgcgtaccagcagg |
| | gccagaaccagctctataacgagctcaatctaggacgaagagag |
| | gagtacgatgtttggacaagagacgtggccgggaccctgagat |
| | ggggggaaagccgcagagaaggaagaaccctcaggaaggcctgt |
| | acaatgaactgcagaaagataagatggcggaggcctacagtgag |
| | attgggatgaaaggcgagcgccggaggggcaaggggcacgatgg |
| | cctttaccagggtctcagtacagccaccaaggacacctacgacg |
| | cccttcacatgcaggccctgcccctcgctaggtcgacaatcaa |
| | cctctggattacaaaatttgtgaaagattgactggtattcttaa |
| | ctatgttgctccattacgctatgtggatacgctgctttaatgcc |
| | tttgtatcatgctattgcttcccgtatggctttcattttctcct |
| | ccttgtataaatcctggttgctgtctctttatgaggagttgtgg |
| | cccgttgtcaggcaacgtggcgtggtgtgcactgtgtttgctga |
| | cgcaaccccactggttgggggcattgccaccacctgtcagctcc |
| | tttccgggactttcgctttccccctccctattgccacggcggaa |
| | ctcatcgccgcctgccttgcccgctgctggacaggggctcggct |
| | gttgggcactgacaattccgtggtgttgtcggggaagctgacgt |
| | cctttccaggctgctcgcctgtgttgccacctggattctgcgc |
| | gggacttcctctgctacgtcccttcggccctcaatccagcgga |
| | ccttccttcccgcggcctgctgccggctctgcggcctcttccgc |
| | gtcttcgccttcgccctcagacgactcggatctctcccttgggcc |
| | gcctccccgcctggaattcgctagctcgagctcacacaaaaaa |
| | ccaacacacagatgtaatgaaaataaagatattttattgcggcc |
| | gctttagtttcggaggtaacctgtaagtctgttaatgaagtaaa |
| | agttccttaggatttccactctgactatggtccaggcacagtga |
| | ctgtactccttggcctcaggtaatgcagaatcctcccataata |
| | tcttttcaggtgcagactgctcatgagttaccctggtgaaatc |
| | ttctttctccagttttttcttccaggactgtcttcagatggttta |
| | tctgatgatagacattagccaggaggttctcaacaatagtctca |
| | ttccagccagtgctagtgaatcttgtctgaaaatagcaaagat |
| | gttctggagcatctcatagatggtcaatgcggcgtcctccttct |
| | ggaactgctgcagctgcttaatctcctcagggatgtcaaagttc |
| | atcctgtccttgaggcagtattcaagcctcccattcaattgcca |
| | caggagcttctgacactgaaaattgctgcttcttttgtaggaatc |
| | caagcaagttgtagctcatggaaagagctgtagtggagaagcac |
| | aacaggagagcaatttggaggagacacttgttggtcatggtgtg |
| | gaccggagcgctaggtcatatgcaggagttgaggttactgtga |
| | gtagtgattaaagagagtgataggggaactcttgaacaagagatg |
| | caatttatactgttaattctggaaaaatattatgggggtgtcaa |
| | aatgtccccggcaattgacgccttctgtatgaaacagttttttc |
| | ctccacgccttctgtatgaaacagttttttcctccacgccttctg |
| | tatgaaacagttttttcctccgtcgaggacaattgacgccttctg |
| | tatgaaacagttttttcctccacgccttctgtatgaaacagtttt |
| | tcctccacgccttctgtatgaaacagttttttcctcc |
| 92 | MTNKCLLQIALLLCFSTTALSMSYNLLGFLQRSSNFQCQKLLWQ |
| | LNGRLEYCLKDRMNFDIPEEIKQLQQFQKEDAALTIYEMLQNIF |
| | AIFRQDSSSTGWNETIVENLLANVYHQINHLKTVLEEKLEKEDF |
| | TRGKLMSSLHLKRYYGRILHYLKAKEYSHCAWTIVRVEILRNFY |
| | FINRLTGYLRN |
| 93 | GGGGSGGGGSGGGGS |
| 94 | Acgccttctgtatgaaacagttttttcctccacgccttctgtatg |
| | aaacagtattcctccacgccttctgtatgaaacagtattcctcc |
| | gtcgaggacaattgacgccttctgtatgaaacagttttttcctcc |
| | acgccttctgtatgaaacagtattcctccacgccttctgtatga |
| | aacagttttttcctcc |

---

The invention claimed is:

1. An antibody or antigen binding unit thereof that specifically binds to claudin 18A2, wherein,
   (a) HCDR1 is SEQ ID NO:31, HCDR2 is SEQ ID NO:32, HCDR3 is SEQ ID NO:33, LCDR1 is SEQ ID NO:34, LCDR2 is SEQ ID NO:35, and LCDR3 is SEQ ID NO:36;
   (b) HCDR1 is SEQ ID NO:37, HCDR2 is SEQ ID NO:38, HCDR3 is SEQ ID NO:39, LCDR1 is SEQ ID NO: 40, LCDR2 is SEQ ID NO: 41, and LCDR3 is SEQ ID NO:42;
   (c) HCDR1 is SEQ ID NO:43, HCDR2 is SEQ ID NO:44, HCDR3 is SEQ ID NO:45, LCDR1 is SEQ ID NO:46, LCDR2 is SEQ ID NO:47, and LCDR3 is SEQ ID NO:48;
   (d) HCDR1 is SEQ ID NO:49, HCDR2 is SEQ ID NO:50, HCDR3 is SEQ ID NO:51, LCDR1 is SEQ ID NO:52, LCDR2 is SEQ ID NO:53, and LCDR3 is SEQ ID NO:54;
   (e) HCDR1 is SEQ ID NO:31, HCDR2 is SEQ ID NO:83, HCDR3 is SEQ ID NO:33, LCDR1 is SEQ ID NO:34, LCDR2 is SEQ ID NO:35, and LCDR3 is SEQ ID NO:36;
   (f) HCDR1 is SEQ ID NO:31, HCDR2 is SEQ ID NO:84, HCDR3 is SEQ ID NO:33, LCDR1 is SEQ ID NO:34, LCDR2 is SEQ ID NO:35, and LCDR3 is SEQ ID NO: 36; or
   (g) HCDR1 is SEQ ID NO:49, HCDR2 is SEQ ID NO:85, HCDR3 is SEQ ID NO:51, LCDR1 is SEQ ID NO:52, LCDR2 is SEQ ID NO:53, and LCDR3 is SEQ ID NO: 54.

2. The antibody or antigen binding unit of claim 1, comprising a heavy chain variable region (VH) and a light chain variable region (VL), wherein
   VH comprises an amino acid sequence of SEQ ID NO:3, SEQ ID NO:7, SEQ ID NO:11, SEQ ID NO:15, SEQ ID NO:17, SEQ ID NO:19, SEQ ID NO:23, SEQ ID NO:27 or SEQ ID NO:29; and
   VL comprises an amino acid sequence of SEQ ID NO:1, SEQ ID NO:5, SEQ ID NO:9, SEQ ID NO:13, SEQ ID NO:21 or SEQ ID NO:25.

3. The antibody or antigen binding unit of claim 2, wherein:
   (a) VH comprises an amino acid sequence of SEQ ID NO:3 and VL comprises an amino acid sequence of SEQ ID NO:1;

(b) VH comprises an amino acid sequence of SEQ ID NO:7 and VL comprises an amino acid sequence of SEQ ID NO:5;
(c) VH comprises an amino acid sequence of SEQ ID NO:11 and VL comprises an amino acid sequence of SEQ ID NO:9;
(d) VH comprises an amino acid sequence of SEQ ID NO:15 and VL comprises an amino acid sequence of SEQ ID NO:13;
(e) VH comprises an amino acid sequence of SEQ ID NO:17 and VL comprises an amino acid sequence of SEQ ID NO:1;
(f) VH comprises an amino acid sequence of SEQ ID NO:19 and VL comprises an amino acid sequence of SEQ ID NO:1;
(g) VH comprises an amino acid sequence of SEQ ID NO:23 and VL comprises an amino acid sequence of SEQ ID NO:21;
(h) VH comprises an amino acid sequence of SEQ ID NO:27 and VL comprises an amino acid sequence of SEQ ID NO:25; or
(i) VH comprises an amino acid sequence of SEQ ID NO:29 and VL comprises an amino acid sequence of SEQ ID NO:25.

4. The antibody or antigen binding unit of claim 1, which is a humanized antibody, a chimeric antibody, a fully humanized antibody, a monoclonal antibody, a single chain antibody, a multivalent antibody, a chimeric antigen receptor, an scFv, an Fv, a Fab, or a F(ab')$_2$.

5. The antibody of claim 1, having
(a) a heavy chain comprising an amino acid sequence of SEQ ID NO:63 and a light chain comprising an amino acid sequence of SEQ ID NO:65;
(b) a heavy chain comprising an amino acid sequence of SEQ ID NO:59 and a light chain comprising an amino acid sequence of SEQ ID NO:61; or
(c) a heavy chain comprising an amino acid sequence of SEQ ID NO:67 and a light chain comprising an amino acid sequence of SEQ ID NO:65.

6. A pharmaceutical composition comprising the antibody or antigen binding unit of claim 1, and a pharmaceutically acceptable carrier.

7. A nucleic acid encoding the antibody or antigen binding fragment of claim 1.

8. An expression vector comprising the nucleic acid of claim 7.

9. A host cell comprising the expression vector of claim 8.

10. A method for producing an antibody or antigen binding unit that specifically binds to claudin 18A2, comprising culturing the host cell of claim 9 under suitable conditions, and obtaining the product expressed by the host cell.

11. A method for preparing an anti-claudin 18A2 targeting drug, an anti-claudin 18A2 antibody-drug conjugate, a multifunctional anti-claudin 18A2 antibody, a reagent for diagnosing a tumor expressing claudin 18A2, or an anti claudin 18A2 chimeric antigen receptor modified immune cell, wherein the method comprises providing the antibody or antigen binding unit of claim 1 and incorporating said antibody or antigen binding unit into the claudin 18A2 targeting drug, the anti-claudin 18A2 antibody-drug conjugate, the multifunctional anti-claudin 18A2 antibody, the reagent for diagnosing a tumor expressing claudin 18A2, or the anti claudin 18A2 chimeric antigen receptor modified immune cell.

12. A chimeric antigen receptor comprising the following sequentially linked components: the antibody or antigen binding unit of claim 1, a transmembrane region, and an intracellular signal region.

13. The chimeric antigen receptor of claim 12, wherein the intracellular signal region is selected from: an intracellular signal region sequence of CD3ζ, FcεRIγ, CD27, CD28, CD137, CD134, MyD88, CD40, and combinations thereof; and/or the transmembrane region comprises a transmembrane region of CD8 or CD28.

14. A nucleic acid encoding the chimeric antigen receptor of claim 12.

15. An expression vector comprising the nucleic acid of claim 14.

16. A virus comprising the vector of claim 15.

17. A chimeric antigen receptor-modified immune cell having the chimeric antigen receptor of claim 12 expressed on the surface.

18. The chimeric antigen receptor-modified immune cell of claim 17, wherein the immune cell is selected from a T lymphocyte, a NK cell, and a NKT lymphocyte.

19. The chimeric antigen receptor-modified immune cell of claim 18, further comprising:
(a) an encoding sequence for an exogenous cytokine;
(b) another expressed chimeric antigen receptor which does not contain CD3ζ but contains an intracellular signal domain of CD28, an intracellular signal domain of CD137, or a combination of the both;
(c) an expressed chemokine receptor;
(d) an expressed siRNA which can reduce expression of PD-1;
(e) an expressed protein which can block PD-L1;
(f) a knock-out of endogenous PD-1 in the immune cell by gene editing techniques;
(g) an expressed safety switch; or
(h) an expressed Type I interferon.

20. A multifunctional immunoconjugate comprising:
an antibody or antigen binding unit of claim 1; and
a functional molecule linked thereto, wherein the functional molecule is selected from a molecule targeting a surface marker on a tumor, a tumor-inhibiting molecule, a molecule targeting a surface marker of an immune cell, and a detectable label.

21. The multifunctional immunoconjugate of claim 20, which is bifunctional and wherein the function molecule is a molecule targeting-a surface marker of an immune cell that is a T cell.

22. A nucleic acid encoding the multifunctional immunoconjugate of claim 20.

23. A kit comprising:
a container, and
the antibody or antigen binding unit of claim 1.

24. The composition of claim 6, further comprising a Type I interferon.

25. A method for inducing the death of a cell comprising a claudin 18A2 peptide, comprising contacting the cell with the antibody or antigen binding unit of claim 1.

26. A method for treating a tumor in an individual in need thereof, comprising administering to the individual an effective amount of the antibody or antigen binding unit of claim 1.

27. The method of claim 26, wherein the tumor is a solid tumor.

28. The method of claim 26, wherein the tumor is associated with gastric cancer, esophageal cancer, intestinal cancer, pancreatic cancer, nephroblastoma, lung cancer, ovarian cancer, colon cancer, rectal cancer, liver cancer, head and neck cancer, chronic myelogenous leukemia, or gallbladder cancer.

29. The method of claim 26, further comprising administering to the individual an additional therapeutic agent selected from epirubicin, oxaliplatin, and 5-fluorouracil.

* * * * *